US006541209B1

(12) United States Patent
Behan et al.

(10) Patent No.: US 6,541,209 B1
(45) Date of Patent: Apr. 1, 2003

(54) NON-ENDOGENOUS, CONSTITUTIVELY ACTIVATED HUMAN SEROTONIN RECEPTORS AND SMALL MOLECULE MODULATORS THEREOF

(75) Inventors: Dominic P. Behan, San Diego; Derek T. Chalmers, Solana Beach; Chen W. Liaw; Joseph F. Russo, both of San Diego; William J. Thomsen, Del Mar, all of CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/292,072

(22) Filed: Apr. 14, 1999

Related U.S. Application Data

(63) Continuation-in-part of application No. 09/060,188, filed on Apr. 14, 1998, which is a continuation-in-part of application No. 08/839,449, filed on Apr. 14, 1997, now abandoned.
(60) Provisional application No. 60/123,000, filed on Mar. 5, 1999, provisional application No. 60/112,909, filed on Dec. 18, 1998, and provisional application No. 60/090,783, filed on Jun. 26, 1998.

(51) Int. Cl.[7] .......................... G01N 33/50; C12N 15/12; C12N 15/63
(52) U.S. Cl. ...................... 435/7.1; 435/69.1; 435/325; 435/172.3; 435/252.3; 536/24.3; 536/23.1; 530/350
(58) Field of Search .................. 435/7.1, 69.1, 435/325, 172.3, 252.3; 536/24.3, 23.1; 530/300, 350

(56) References Cited

U.S. PATENT DOCUMENTS

| 4,985,352 A | 1/1991 | Julius et al. ................. 435/6 |
| 5,661,024 A | 8/1997 | Kao et al. ................ 435/240.2 |

FOREIGN PATENT DOCUMENTS

| CA | 2135253 | 5/1996 |
| WO | WO 96/23783 | 8/1996 |

OTHER PUBLICATIONS

Barluenga, J. et al., "A New and Specific Method for the Monomethylation of Primary Amines," *J. Chem. Soc. Chem. Commun.*, 1984, 20, 1334–1335.
Batey, R.A. et al., "An Efficient New Protocol for the Formation of Unsymmetrical Tri– and Tetrasubstituted Ureas," *Tetra. Lett.*, 1998, 39, 6267–6270.

Bernatowicz, M. et al., "A Comparison of Acid Labile Linkage Agents for the Synthesis of Peptide C–Terminal Amides," *Tetra. Lett.*, 1989, 30(35), 4645–4648.
Carter, H.E. et al., "Carbonbenzoxy Chloride and Derivatives," *Org. Syn. Coll.*, 1955, vol. 3, 167–169.
Casey, C. et al., "Constitutively Active Mutant $5HT_{2A}$ Serotonin Receptors: Inverse Agonist Activity of Classical $5HT_{2A}$ Antagonists," *Society for Neuroscience Abstracts*, 1996, 22(3), Abstract No. 699.10.
Gutsche, C.D. et al., "2–Phenylcycloheptanone," *Org. Syn. Coll.*, 1963, vol. 4, 780–783.
Herrick–Davis, K. et al., "Activating Mutations of the Serotonin $5-HT_{2C}$ Receptor," *J. Neurochem.*, 1997, 69(3), 1138–1144.
Herrick–Davis, K. et al., "Constitutively Active 5HT2C Serotonin Receptor Created by Site–Directed Mutagenesis," *Society for Neuroscience Abstracts*, 1996, 22(3), Abstract No. 699.18.
Marchini, P. et al., "Sodium Borohydride–Carboxylic Acid Systems. Useful Reagents for the Alkylation of Amines," *J. Org. Chem.*, 1975, 40(23), 3453–3456.
Sahgal, A. (ed.), "Practical behavioral neurosceience: problems, pitfalls and suggestions," in *Behavioral Neuroscience: A Practical Approach*, IRL Press, New York, 1993, vol. 1–18.
Sheehan, J.C. et al., "1–Ethyl–3–(3–Dimethylamiono)Propylcarbodiimide Hydrochloride and Methiodide," *Org. Syn. Coll.*, 1973, vol. 5, 555–558.
Soresnon et al., "Characterization of the $5–HT_2$ Receptor Antagonist MDL 100907 as a Putative Atypical Antipsychotic: Behavioral, Electrophysiological and Neurochemical Studies," *J. Pharacol. Exp. Ther.*, 1993, 266(2), 684–691.
White, E., "Deamination of Amines. 2–Phenylethyl Benzoate Via the Nitrosoamide Decomposition," *Org. Syn. Coll.*, 1973, vol. 5, 336–339.

*Primary Examiner*—Yvonne Eyler
*Assistant Examiner*—Nirmal S. Basi
(74) *Attorney, Agent, or Firm*—Woodcock Washburn Mackiewicz Norris LLP; Ann A. Nguyen; Richard P. Burgoon, Jr.

(57) ABSTRACT

Disclosed herein are non-endogenous, constitutively activated forms of the human $5-HT_{2A}$ and human $5-HT_{2C}$ receptors and uses of such receptors to screen candidate compounds. Further disclosed herein are candidate compounds identified by the screening method which act at the $5HT_{2A}$ receptors. Yet further disclosed is a new class of compounds which act at the $5HT_{2A}$ receptors.

1 Claim, 17 Drawing Sheets

FIG. 3A

ATGGATATTCTTTGTGAAGAAAATACTTCTTTGAGCTCAACTACGAACTCCCTAATGCAATTA

AATGATGACAACAGGCTCTACAGTAATGACTTTAACTCCGGAGAAGCTAACACTTCTGATGCA

TTTAACTGGACAGTCGACTCTGAAAATCGAACCAACCTTTCCTGTGAAGGGTGCCTCTCACCG

TCGTGTCTCTCCTTACTTCATCTCCAGGAAAAAAACTGGTCTGCTTTACTGACAGCCGTAGTGA

TTATTCTAACTATTGCTGGAAACATACTCGTCATCATGGCAGTGTCCCTAGAGAAAAAGCTGC

AGAATGCCACCAACTATTTCCTGATGTCACTTGCCATAGCTGATATGCTGCTGGGTTTCCTTGT

CATGCCCGTGTCCATGTTAACCATCCTGTATGGGTACCGGTGGCCTCTGCCGAGCAAGCTTTGT

GCAGTCTGGATTTACCTGGACGTGCTCTTCTCCACGGCCTCCATCATGCACCTCTGCGCCATCT

CGCTGGACCGCTACGTCGCCATCCAGAATCCCATCCACCACAGCCGCTTCAACTCCAGAACTA

AGGCATTTCTGAAAATCATTGCTGTTTGGACCATATCAGTAGGTATATCCATGCCAATACCAG

TCTTTGGGCTACAGGACGATTCGAAGGTCTTTAAGGAGGGGAGTTGCTTACTCGCCGATGATA

ACTTTGTCCTGATCGGCTCTTTTGTGTCATTTTTCATTCCCTTAACCATCATGGTGATCACCTAC

TTTCTAACTATCAAGTCACTCCAGAAAGAAGCTACTTTGTGTGTAAGTGATCTTGGCACACGG

GCCAAATTAGCTTCTTTCAGCTTCCTCCCTCAGAGTTCTTTGTCTTCAGAAAAGCTCTTCCAGC

GGTCGATCCATAGGGAGCCAGGGTCCTACACAGGCAGGAGGACTATGCAGTCCATCAGCAAT

GAGCAAAAGGCATGCAAGGTGCTGGGCATCGTCTTCTTCCTGTTTGTGGTGATGTGGTGCCCT

TTCTTCATCACAAACATCATGGCCGTCATCTGCAAAGAGTCCTGCAATGAGGATGTCATTGGG

GCCCTGCTCAATGTGTTTGTTTGGATCGGTTATCTCTCTTCAGCAGTCAACCCACTAGTCTACA

CACTGTTCAACAAGACCTATAGGTCAGCCTTTTCACGGTATATTCAGTGTCAGTACAAGGAAA

ACAAAAAACCATTGCAGTTAATTTTAGTGAACACAATACCGGCTTTGGCCTACAAGTCTAGCC

AACTTCAAATGGGACAAAAAAGAATTCAAAGCAAGATGCCAAGACAACAGATAATGACTGC

TCAATGGTTGCTCTAGGAAAGCAGTATTCTGAAGAGGCTTCTAAAGACAATAGCGACGGAGT

GAATGAAAAGGTGAGCTGTGTGTGA

FIG. 3B

MDILCEENTSLSSTTNSLMQLNDDNRLYSNDFNSGEANTSDAFNWTVDSENRTNLSCEGCLSPSCL

SLLHLQEKNWSALLTAVVIILTIAGNILVIMAVSLEKKLQNATNYFLMSLAIADMLLGFLVMPVSM

LTILYGYRWPLPSKLCAVWIYLDVLFSTASIMHLCAISLDRYVAIQNPIHHSRFNSRTKAFLKIIAVW

TISVGISMPIPVFGLQDDSKVFKEGSCLLADDNFVLIGSFVSFFIPLTIMVITYFLTIKSLQKEATLCVS

DLGTRAKLASFSFLPQSSLSSEKLFQRSIHREPGSYTGRRTMQSISNEQKACKVLGIVFFLFVVMWC

PFFITNIMAVICKESCNEDVIGALLNVFVWIGYLSSAVNPLVYTLFNKTYRSAFSRYIQCQYKENKK

PLQLILVNTIPALAYKSSQLQMGQKKNSKQDAKTTDNDCSMVALGKQYSEEASKDNSDGVNEKV

SCV

FIG. 4B

MVNLRNAVHSFLVHLIGLLVWQCDISVSPVAAIVTDIFNTSDGGRFKFPDGVQNWPALSIVIIIIMTIGGN

ILVIMAVSMEKKLHNATNYFLMSLAIADMLVGLLVMPLSLLAILYDYVWPLPRYLCPVWISLDVLFSTASI

MHLCAISLDRYVAIRNPIEHSRFNSRTKAIMKIAIVWAISIGVSVPIPVIGLRDEEKVFVNNTTCVLNDPN

FVLIGSFVAFFIPLTIMVITYCLTIYVLRRQALMLLHGHTEEPPGLSLDFLKCCKRNTAEEENSANPNQDQ

NARRRKKKERRPRGTMQAINNERKASKVLGIVFFVFLIMWCPFFITNILSVLCEKSCNQKLMEKLLNVFVW

IGYVCSGINPLVYTLFNKIYRRAFSNYLRCNYKVEKKPPVRQIPRVAATALSGRELNVNIYRHTNEPVIEK

ASDNEPGIEMQVENLELPVNPSSVVSERISSV

FIG. 4A

ATGGTGAACCTGAGGAATGCGGTGCATTCATTCCTTGTGCACCTAATTGGCCTATTGGTTTGGC

AATGTGATATTTCTGTGAGCCCAGTAGCAGCTATAGTAACTGACATTTTCAATACCTCCGATG

GTGGACGCTTCAAATTCCCAGACGGGGTACAAAACTGGCCAGCACTTTCAATCGTCATCATAA

TAATCATGACAATAGGTGGCAACATCCTTGTGATCATGGCAGTAAGCATGGAAAAGAAACTG

CACAATGCCACCAATTACTTCTTAATGTCCCTAGCCATTGCTGATATGCTAGTGGGACTACTTG

TCATGCCCTGTCTCTCCTGGCAATCCTTTATGATTATGTCTGGCCACTACCTAGATATTTGTG

CCCCGTCTGGATTTCTTTAGATGTTTTATTTTCAACAGCGTCCATCATGCACCTCTGCGCTATAT

CGCTGGATCGGTATGTAGCAATACGTAATCCTATTGAGCATAGCCGTTTCAATTCGCGGACTA

AGGCCATCATGAAGATTGCTATTGTTTGGGCAATTTCTATAGGTGTATCAGTTCCTATCCCTGT

GATTGGACTGAGGGACGAAGAAAAGGTGTTCGTGAACAACACGACGTGCGTGCTCAACGACC

CAAATTTCGTTCTTATTGGGTCCTTCGTAGCTTTCTTCATACCGCTGACGATTATGGTGATTAC

GTATTGCCTGACCATCTACGTTCTGCGCCGACAAGCTTTGATGTTACTGCACGGCCACACCGA

GGAACCGCCTGGACTAAGTCTGGATTTCCTGAAGTGCTGCAAGAGGAATACGGCCGAGGAAG

AGAACTCTGCAAACCCTAACCAAGACCAGAACGCACGCCGAAGAAAGAAGAAGGAGAGACG

TCCTAGGGGCACCATGCAGGCTATCAACAATGAAAGAAAAGCTTCGAAAGTCCTTGGGATTG

TTTTCTTTGTGTTTCTGATCATGTGGTGCCCATTTTTCATTACCAATATTCTGTCTGTTCTTTGTG

AGAAGTCCTGTAACCAAAAGCTCATGGAAAAGCTTCTGAATGTTGTTTGTTTGGATTGGCTAG

TTTGTTCAGGAATCAATCCTCTGGTGTATACTCTGTTCAACAAAATTTACCGAAGGGCATTCTC

CAACTATTTGCGTTGCAATTATAAGGTAGAGAAAAAGCCTCCTGTCAGGCAGATTCCAAGAGT

TGCCGCCACTGCTTTGTCTGGGAGGGAGCTTAATGTTAACATTTATCGGCATACCAATGAACC

GGTGATCGAGAAAGCCAGTGACAATGAGCCCGGTATAGAGATGCAAGTTGAGAATTTAGAGT

TACCAGTAAATCCCTCCAGTGTGGTTAGCGAAAGGATTAGCAGTGTGTGA

FIG. 5A

ATGGTGAACCTGAGGAATGCGGTGCATTCATTCCTTGTGCACCTAATTGGCCTATTGGTTTGGCAAT

GTGATATTTCTGTGAGCCCAGTAGCAGCTATAGTAACTGACATTTTCAATACCTCCGATGGTGGACG

CTTCAAATTCCCAGACGGGGTACAAAACTGGCCAGCACTTTCAATCGTCATCATAATAATCATGAC

AATAGGTCGCAACATCCTTGTGATCATGGCAGTAAGCATGGAAAAGAAACTGCACAATGCCACCA

ATTACTTCTTAATGTCCCTAGCCATTGCTGATATGCTAGTGGGACTACTTGTCATGCCCCTGTCTCTC

CTGGCAATCCTTTATGATTATGTCTGGCCATCAACTAGATATTTGTGCCCGTCTGGATTTCTTTAGA

TGTTTTATTTTCAACAGCGTCCATCATGCACCTCTGCGCTATATCGCTGGATCGGTATGTAGCAATA

CGTAATTCTATTGAGCATAGCCGTTTCAATTCGCGGACTAAGGCCATCATGAAGATTGCTATTGTTT

GGGCAATTTCTATAGGTGTATCAGTTCCTATCCCTGTGATTGGACTGAGGGACGAAGAAAAGGTGT

TCGTGAACAACACGACGTGCGTGCTCAACGACCCAAATTTGCTTCTTATTGGGTCCTTCGTAGCTTT

CTTCATACCGCTGACGATTATGGTGATTACGTATTGCCTGACCATCTACGTTCTGCGCCGACAAGCT

TTGATGTTACTGCACGGCCACACCGAGGAACCGCCTGGACTAAGTCTGTATTTCCTGAACTGCTGC

AAGAGGAATACGGCCGAGGAAGAGAACTCTGCAAACCCTAACCAAGACCAGAACGCACGCCGAA

GAAAGAAGAAGGAGAGACGTCCTAGGGGCACCATGCAGGCTATCAACAATGAAAGAAAAGCTAA

GAAAGTCCTTGGGATTGTTTTCTTTGTGTTTCTGATCATGTGGTGCCCATTTTTCATTACCAATATTC

TGTCTGTTCTTTGTGAGAAGTCCTGTAACCAAAAGCTCATGGAAAAGCTCTGAATGTGTTTGTTTG

GATTGGCTATGTTTGTTCAGGATTCAATCCTCTGGTGTATACTCTGTTCAACAAAATTTACCGAAGG

GCATTCTCCAACTATTTGCGTTGCAATTATAAGGTAGAGAAAAAGCCCTCCTGTCAGGCAGATTCCA

AGAGTTGCCGCCACTGCTTTGTCTGGGAGGGAGCTTATTGTTAACATTTATCGGCATACCAATGAA

CCGGTGATCGAGAAAGCCAGTGACAATGAGCCCGGTATAGAGATGCAAGTTGAGAATTTAGAGTT

ACCAGTAAATCCCTCCAGTGTGGTTAGCGAAAGGATTAGCAGTGTGTGA

FIG. 5B

MVNLRNAVHSFLVHLIGLLVWQCDISVSPVAAIVTDIFNTSDGGRFKFPDGVQNWPALSIVIIIIMTI
GGNILVIMAVSMEKKLHNATNYFLMSLAIADMLVGLLVMPLSLLAILYDYVWPLPRYLCPVWISL
DVLFSTASIMHLCAISLDRYVAIRNPIEHSRFNSRTKAIMKIAIVWAISIGVSVPIPVIGLRDEEKVFV
NNTTCVLNDPNFVLIGSFVAFFIPLTIMVITYCLTIYVLRRQALMLLHGHTEEPPGLSDFLKCCKRN
TAEEENSANPNQDQNARRRKKKERRPRGTMQAINNERKAKKVLGIVFFVFLIMWCPFFITNILSVL
CEKSCNQKLMEKLLNVFVWIGYVCSGINPLVYTLFNKIYRRAFSNYLRCNYKVEKKPPVRQIPRV
AATALSGRENLNVNIYRHTNEPVIEKASDNEPGIEMQVENLELPVNPSSVVSERISSV

FIG. 6B

MDILCEENTSLSSTTNSLMQLNDDNRLYSNDFNSGEANTSDAFNWTVDSENRTNLSCEGCLSPSCL
SLLHLQEKNWSALLTAVVIILLTIAGNILVIMAVSLEKKLQNATNYFLMSLAIADMLLGFLVMPVSM
LTILYGYRWPLPSKLCAVWIYLDVLFSTASIMHLCAISLDRYVAIQNPIHHSRFNSRTKAFLKIIAVW
TISVGISMPIPVFGLQDDSKVFKEGSCLLADDNFVLIGSFVSFFIPLTIMVITYFLTIKVLRRQALMLL
HGHTEEPPGLSLDFLKCCKRNTAEEENSANPNQDQNARRRKKKERRPRGTMQAINNERKAS
KVLGIVFFLFVVMWCPFFITNIMAVICKESCNEDVIGALLNVFVWIGYLSSAVNPLVYTLFNKIYR
RAFSNYLRCNYKVEKKPPVRQIPRVAATALSGRELNVNIYRHTNEPVIEKASDNEPGIEMQVE
NLELPVNPSSVVSERISSV

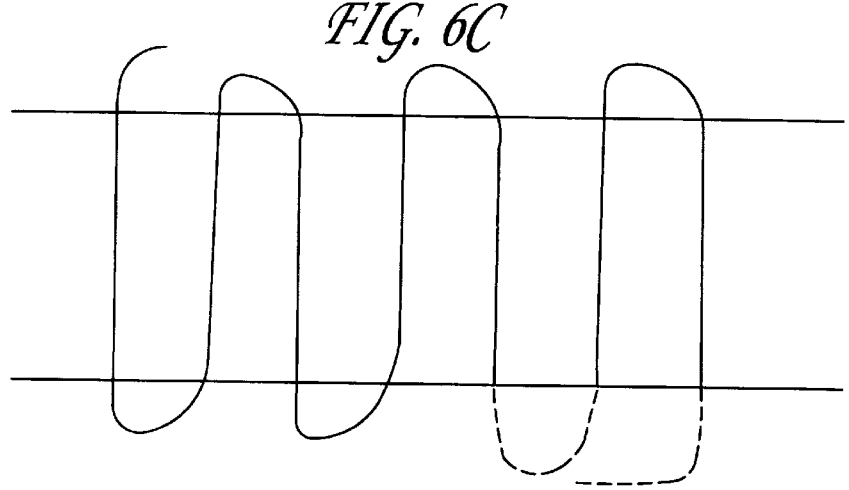

ATGGATATTCTTTGTGAAGAAAATACTTCTTTGAGCTCAACTACGAACTCCCTAATGCAATTA

AATGATGACAACAGGCTCTACAGTAATGACTTTAACTCCGGAGAAGCTAACACTTCTGATGCA

TTTAACTGGACAGTCGACTCTGAAAATCGAACCAACCTTTCCTGTGAAGGGTGCCTCTCACCG

TCGTGTCTCTCCTTACTTCATCTCAGGAAAAAAACTGGTCTGCTTTACTGACAGCCGTAGTGA

TTATTCTAACTATTGCTGGAAACATACTCGTCATCATGGCAGTGTCCCTAGAGAAAAAGCTGC

AGAATGCCACCAACTATTTCCTGATGTCACTTGCCATAGCTGATATGCTGCTGGGTTTCCTTGT

CATGCCCGTGTCCATGTTAACCATCCTGTATGGGTACCGGTGGCCTCTGCCGAGCAAGCTTTGT

GCAGTCTGGATTTACCTGGACGTGCTCTTCTCCACGGCCTCCATCATGCACCTCTGCGCCATCT

CGCTGGACCGCTACGTCGCCATCCAGAATCCCATCCACCACAGCCGCTTCAACTCCAGAACTA

AGGCATTTCTGAAAATCATTGCTGTTTGGACCATATCAGTAGGTATATCCATGCCAATACCAG

TCTTTGGGCTACAGGACGATTCGAAGGTCTTTAAGGAGGGGAGTTGCTTACTCGCCGATGATA

ACTTTGTCTGATCGGCTCTTTTGTGTCATTTTTCATTCCCTTAACCATCATGGTGATCACCTAC

TTTCTAACTATCAAGGTTCTGCGCCCGACAAGCTTTGATGTTACTGCACGGCCACACCGAG

GAACCGCCTGGACTAAGTCTGGATTTCCTGAAGTGCTGCAAGAGGAATACGGCCGAGGA

AGAGAACTCTGCAAACCCTAACCAAGACCAGAACGCACGCCGAAGAAAGAAGAAGGAG

AGACGTCCTAGGGGCACCATGCAGGCTATCAACAATGAAAGAAAAGCTTCGAAGGTACT

GGGCATCGTCTTCTTCCTGTTTGTGGTGATGTGGTGCCCTTTCTTCATCACAAACATCATGGCC

GTCATCTGCAAAGAGTCCTGCAATGAGGATGTCATTGGGGCCCTGCTCAATGTGTTTGTTTGG

ATCGGTTATCTCTCTTCAGCAGTCAACCCACTAGTCTATACTCTGTTCAACAAAATTTACCGA

AGGGCATTCTCCAACTATTTGCGTTGCAATTATAAGGTAGAGAAAAAGCCTCCTGTCAG

GCAGATTCCAAGAGTTGCCGCCACTGCTTTGTCTGGGAGGGAGCTTAATGTTAACATTT

ATCGGCATACCAATGAACCGGTGATCGAGAAAGCCAGTGACAATGAGCCCGGTATAGAG

ATGCAAGTTGAGAATTTAGAGTTACAGTAAATCCCTCCAGTGTGGTTAGCGAAAGGAT

TAGCAGTGTGTGA

FIG. 7A

ATGGATATTCTTTGTGAAGAAAATACTTCTTTGAGCTCAACTACGAACTCCCTAATGCAATTA

AATGATGACAACAGGCTCTACAGTAATGACTTTAACTCCGGAGAAGCTAACACTTCTGATGCA

TTTAACTGGACAGTCGACTCTGAAAATCGAACCAACCTTTCCTGTGAAGGGTGCCTCTCACCG

TCGTGTCTCTCCTTACTTCATCTCCAGGAAAAAAACTGGTCTGCTTTACTGACAGCCGTAGTGA

TTATTCTAACTATTGCTGGAAACATACTCGTCATCATGGCAGTGTCCCTAGAGAAAAGCTGC

AGAATGCCACCAACTATTTCCTGATGTCACTTGCCATAGCTGATATGCTGCTGGGTTTCCTTGT

CATGCCCGTGTCCATGTTAACCATCCTGTATGGGTACCGGTGGCCTCTGCCGAGCAAGCTTTGT

GCAGTCTGGATTTACCTGGACGTGCTCTTCTCCACGGCCTCCATCATGCACCTCTGCGCCATCT

CGCTGGACCGCTACGTCGCCATCCAGAATCCCATCCACCACAGCCGCTTCAACTCCAGAACTA

AGGCATTTCTGAAAATCATTGCTGTTTGGACCATATCAGTAGGTATATCCATGCCAATACCAG

TCTTTGGGCTACAGGACGATTCGAAGGTCTTTAAGGAGGGGAGTTGCTTACTCGCCGATGATA

ACTTTGTCCTGATCGGCTCTTTTGTGTCATTTTTCATTCCCCTGACGATTATGGTGATTACGT

ATTGCCTGACCATCTACGTTCTGCGCCGACAAGCTTTGATGTTACTGCACGGCCACACC

GAGGAACCGCCTGGACTAAGTCTGGATTTCCTGAAGTGCTGCAAGAGGAATACGGCCGA

GGAAGAGAACTCTGCAAACCCTAACCAAGACCAGAACGCACGCCGAAGAAAGAAGAAG

GAGAGACGTCCTAGGGGCACCATGCAGGCTATCAACAATGAAAGAAAAGCTAAGAAAGT

CCTTGGGATTGTTTTCTTTGTGTTTCTGATCATGTGGTGCCCTTTCTTCATCACAAACATCA

TGGCCGTCATCTGCAAAGAGTCCTGCAATGAGGATGTCATTGGGGCCCTGCTCAATGTGTTTG

TTTGGATCGGTTATCTCTCTTCAGCAGTCAACCCACTAGTCTATACTCTGTTCAACAAAATTT

ACCGAAGGGCATTCTCCAACTATTTGCGTTGCAATTATAAGGTAGAGAAAAAGCCTCCT

GTCAGGCAGATTCCAAGAGTTGCCGCCACTGCTTTGTCTGGGAGGGAGCTTAATGTTAA

CATTTATCGGCATACCAATGAACCGGTGATCGAGAAAGCCAGTGACAATGAGCCCGGTA

TAGAGATGCAAGTTGAGAATTTAGAGTTACCAGTAAATCCCTCCAGTGTGGTTAGCGAA

AGGATTAGCAGTGTGTGA

FIG. 7B

MDILCEENTSLSSTTNSLMQLNDDNRLYSNDFNSGEANTSDAFNWTVDSENRTNLSCEGCLSPSCL
SLLHLQEKNWSALLTAVVIILTIAGNILVIMAVSLEKKLQNATNYFLMSLAIADMLLGFLVMPVSM
LTILYGYRWPLPSKLCAVWIYLDVLFSTASIMHLCAISLDRYVAIQNPIHHRSFNSRTKAFLKIIAVW
TISVGISMPIPVFGLQDDSKVFKEGSCLLADDNFVLIGSFVSFFIPLTIMVTTYCLTIYVLRRQALML
LHGHTEEPPGLSLDFLKCCKRNTAEEENSANPNQDQNARRRKKKERRPRGTMQAINNERKA
KKVLGIVFFVFLIMWCPFFITNIMAVICKESCNEDVIGALLNVFVWIGYLSSAVNPLVYTLFNKIY
RRAFSNYLRCNYKVEKKPPVRQIPRVAATALSGRELNVNIYRHTNEPVIEKASDNEPGIEMQV
ENLELPVNPSSVVSERISSV

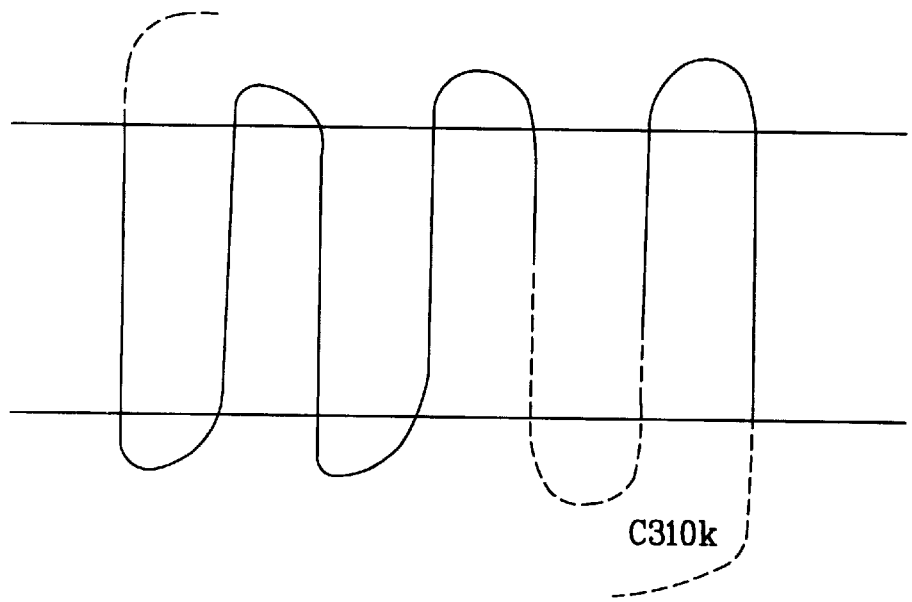

FIG. 7C

*Xho I (1312) to Sca I (3049) is identical to pRc/RSV Xho I (3045) to 4782.
*Sca I (3049) to 4070 is identical to pCDM7 Amp ScaI (2524) to 3545.
*multiple cloning site includes Hind III to Sac I of pBluescript II.
*110 to 1312 is identical to pCMD7 Amp 76 to 1278.
*Sac I and Spe I in MCS are not unique.

NON-ENDOGENOUS, CONSTITUTIVELY ACTIVATED HUMAN SEROTONIN RECEPTORS AND SMALL MOLECULE MODULATORS THEREOF

This application is a continuation-in-part of U.S. application Ser. No. 09/060,188, filed Apr. 14, 1998 (owned by Arena Pharmaceuticals, Inc.), which is a continuation-in-part of Ser. No. 08/839,449 filed Apr. 14, 1997 now abandoned and claims priority to U.S. Provisional Application No. 60/090,783, filed Jun. 26, 1998 (owned by Arena Pharmaceuticals, Inc.), now abandoned, U.S. Provisional Application No. 60/112,909, filed Dec. 18, 1998, now abandoned and U.S. Provisional Application No. 60/123,000, filed Mar. 5, 1999, now abandoned.

FIELD OF THE INVENTION

The present invention relates to non-endogenous, constitutively active serotonin receptors and small molecule modulators thereof.

BACKGROUND OF THE INVENTION

I. G protein-coupled receptors

G protein-coupled receptors share a common structural motif All these receptors have seven sequences of between 22 to 24 hydrophobic amino acids that form seven alpha helices, each of which spans the membrane. The transmembrane helices are joined by strands of amino acids having a larger loop between the fourth and fifth transmembrane helix on the extracellular side of the membrane. Another larger loop, composed primarily of hydrophilic amino acids, joins transmembrane helices five and six on the intracellular side of the membrane. The carboxy terminus of the receptor lies intracellularly with the amino terminus in the extracellular space. It is thought that the loop joining helices five and six, as well as, the carboxy terminus, interact with the G protein. Currently, Gq, Gs, Gi, and Go are G proteins that have been identified. The general structure of G protein-coupled receptors is shown in FIG. 1.

Under physiological conditions, G protein-coupled receptors exist in the cell membrane in equilibrium between two different states or conformations: an "inactive" state and an "active" state. As shown schematically in FIG. 2, a receptor in an inactive state is unable to link to the intracellular transduction pathway to produce a biological response. Changing the receptor conformation to the active state allows linkage to the transduction pathway and produces a biological response.

A receptor may be stabilized in an active state by an endogenous ligand or an exogenous agonist ligand. Recent discoveries such as, including but not exclusively limited to, modifications to the amino acid sequence of the receptor provide means other than ligands to stabilize the active state conformation. These means effectively stabilize the receptor in an active state by simulating the effect of a ligand binding to the receptor. Stabilization by such ligand-independent means is termed "constitutive receptor activation."

II. Serotonin receptors

Receptors for serotonin (5-hydroxytryptamine, 5-HT) are an important class of G protein-coupled receptors. Serotonin is thought to play a role in processes related to learning and memory, sleep, thermoregulation, mood, motor activity, pain, sexual and aggressive behaviors, appetite, neurodegenerative regulation, and biological rhythms. Not surprisingly, serotonin is linked to pathophysiological conditions such as anxiety, depression, obsessive-compulsive disorders, schizophrenia, suicide, autism, migraine, emesis, alcoholism and neurodegenerative disorders.

Serotonin receptors are divided into seven subfamilies, referred to as 5-HT1 through 5-HT7, inclusive. These subfamilies are further divided into subtypes. For example, the 5-HT2 subfamily is divided into three receptor subtypes: 5-HT2A, 5-HT2B, and 5-HT2C. The human 5-HT2C receptor was first isolated and cloned in 1987, and the human 5-HT2A receptor was first isolated and cloned in 1990. These two receptors are thought to be the site of action of hallucinogenic drugs. Additionally, antagonists to the 5-HT2A and 5-HT2C receptors are believed to be useful in treating depression, anxiety, psychosis and eating disorders.

U.S. Pat. No. 4,985,352, describes the isolation, characterization, and expression of a functional cDNA clone encoding the entire human 5-HT1C receptor (now known as the 5HT2C receptor). U.S. Pat. No. 5,661,0124 describes the isolation, characterization, and expression of a functional cDNA clone encoding the entire human 5-HT2A receptor.

Mutations of the endogenous forms of the rat 5-HT2A and rat 5-HT2C receptors have been reported to lead to constitutive activation of these receptors (5-HT2A: Casey, C. et al. (1996) *Society for Neuroscience Abstracts*, 22:699.10, hereinafter "Casey"; 5-HT2C: Herrick-Davis, K., and Teitler, M. (1996) *Society for Neuroscience Abstracts*, 22:699.18, hereinafter "Herrick-Davis 1"; and Herrick-Davis, K. et al. (1997) *J.Neurochemistry* 69(3): 1138, hereinafter "Herrick-Davis-2"). Casey describes a mutation of the cysteine residue at position 322 of the rat 5-HT2A receptor to lysine (C322K), glutamine (C322Q) and argimine (C322R) which reportedly led to constitutive activation. Herrick-Davis 1 and Herrick-Davis 2 describe mutations of the serine residue at position 312 of the rat 5-HT2C receptor to phenylalanine (S312F) and lysine (S312K), which reportedly led to constitutive activation.

SUMMARY OF THE INVENTION

The present invention relates to non-endogenous, constitutively activated forms of the human 5-HT2A and human 5-HT2C receptors and various uses of such receptors. Further disclosed are small molecule modulators of these receptors. Most preferably, these modulators have inverse agonist characteristics at the receptor.

More specifically, the present invention discloses nucleic acid molecules and the proteins for three non-endogenous, constitutively activated human serotonin receptors, referred to herein as, AP-1, AP-3, and AP4. The AP-1 receptor is a constitutively active form of the human 5-HT2C receptor created by an S310K point mutation. The AP-3 receptor is a constitutively active form of the human 5-HT2A receptor whereby the intracellular loop 3 (IC3) portion and the cytoplasmic-tail portion of the endogenous human 5-HT2A receptor have been replaced with the IC3 portion and the cytoplasmic-tail portion of the human 5-HT2C receptor. The AP-4 receptor is a constitutively active form of the human 5-HT2A receptor whereby (1) the region of the intracellular third loop between the proline of the transmembrane 5 region (TM5) and the proline of TM6 of the endogenous human 5-HT2A receptor has been replaced with the corresponding region of the human 5-HT2C receptor (including a S310K point mutation); and (2) the cytoplasmic-tail portion of the endogenous human 5-HT2A receptor has been replaced with the cytoplasmic-tail portion of the endogenous human 5-HT2C receptor.

The invention also provides assays that may be used to directly identify candidate compounds as agonists, partial agonists or inverse agonists to non-endogenous, constitutively activated human serotonin receptors; such candidate compounds can then be utilized in pharmaceutical composition(s) for treatment of diseases and disorders which are related to the human 5-HT2A and/or human 5-HT2C receptors.

These and other aspects of the invention disclosed herein will be set forth in greater detail as the patent disclosure proceeds.

BRIEF DESCRIPTION OF THE DRAWINGS

In the following figures, bold typeface indicates the location of the mutation in the non-endogenous, constitutively activated receptor relative to the corresponding endogenous receptor.

FIG. 3a provides the nucleic acid sequence of the endogenous human 5-HT2A receptor (SEQ.ID.NO: 24).

FIG. 3b provides the corresponding amino acid sequence of the endogenous human 5-HT2A receptor (SEQ.ID.NO: 25).

FIG. 4a provides the nucleic acid sequence of the endogenous human 5-HT2C receptor (SEQ.ID.NO: 26).

FIG. 4b provides the corresponding amino acid sequence of the endogenous human 5-HT2C receptor (SEQ.ID.NO: 27).

FIG. 5a provides the nucleic acid sequence of a constitutively active form of the human 5-HT2C receptor ("AP-1 cDNA"—SEQ.ID.NO: 28).

FIG. 5b provides the corresponding amino acid sequence of the AP-1 cDNA ("AP-1"—SEQ.ID.NO: 29).

FIG. 6a provides the nucleic acid sequence of a constitutively active form of the human 5-HT2A receptor whereby the IC3 portion and the cytoplasmic-tail portion of the endogenous 5-HT2A receptor have been replaced with the IC3 portion and the cytoplasmic-tail portion of the human 5-HT2C receptor ("AP-3 cDNA"—SEQ.ID.NO: 30).

FIG. 6b provides the corresponding amino acid sequence of the AP-3 cDNA ("AP-3"—SEQ.ID.NO: 31).

FIG. 6c provides a schematic representation of AP-3, where the dashed-lines represent the portion obtained from the human 5-HT2C receptor.

FIG. 7a provides the nucleic acid sequence of a constitutively active form of the human 5-HT2A receptor whereby (1) the region of the between the proline of TM5 and the proline of TM6 of the endogenous human 5-HT2A receptor has been replaced with the corresponding region of the human 5-HT2C receptor (including a S310K point mutation); and (2) the cytoplasmic-tail portion of the endogenous 5-HT2A receptor has been replaced with the cytoplasmic-tail portion of the endogenous human 5-HT2C receptor ("AP-4 cDNA"—SEQ.ID.NO:32).

FIG. 7b provides corresponding amino acid sequence of the AP-4 cDNA ("AP-4"—SEQ.ID.NO: 33).

FIG. 7c provides a schematic representation of the mutated 5-HT2A receptor of FIG. 7b where the dashed-lines represent the portion obtained from the human 5-HT2C receptor.

DEFINITIONS

Figure 1:
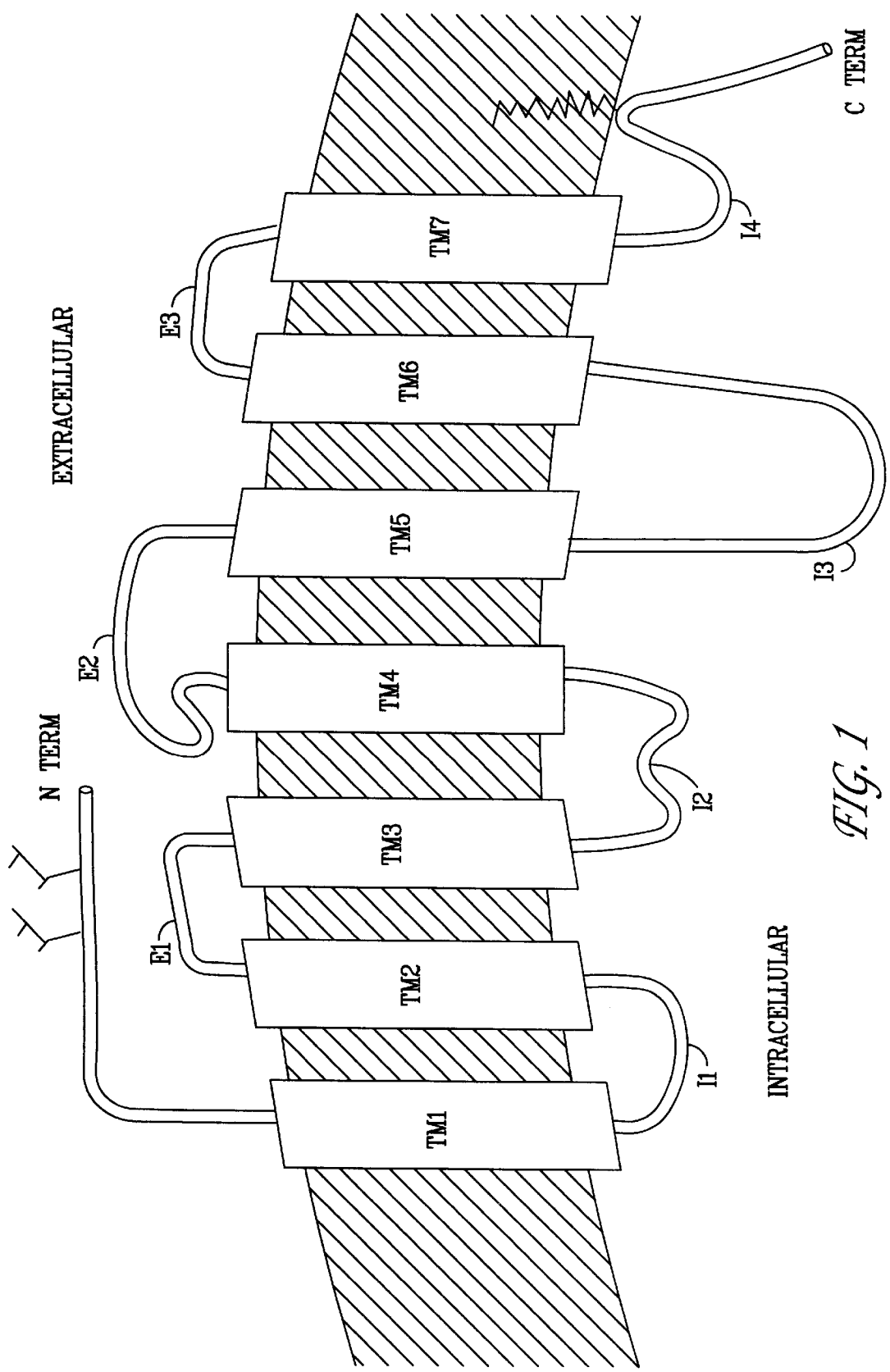
FIG. 1 shows a generalized structure of a G protein-coupled receptor with the numbers assigned to the transmembrane helices, the intracellular loops, and the extracellular loops.
Figure 2:
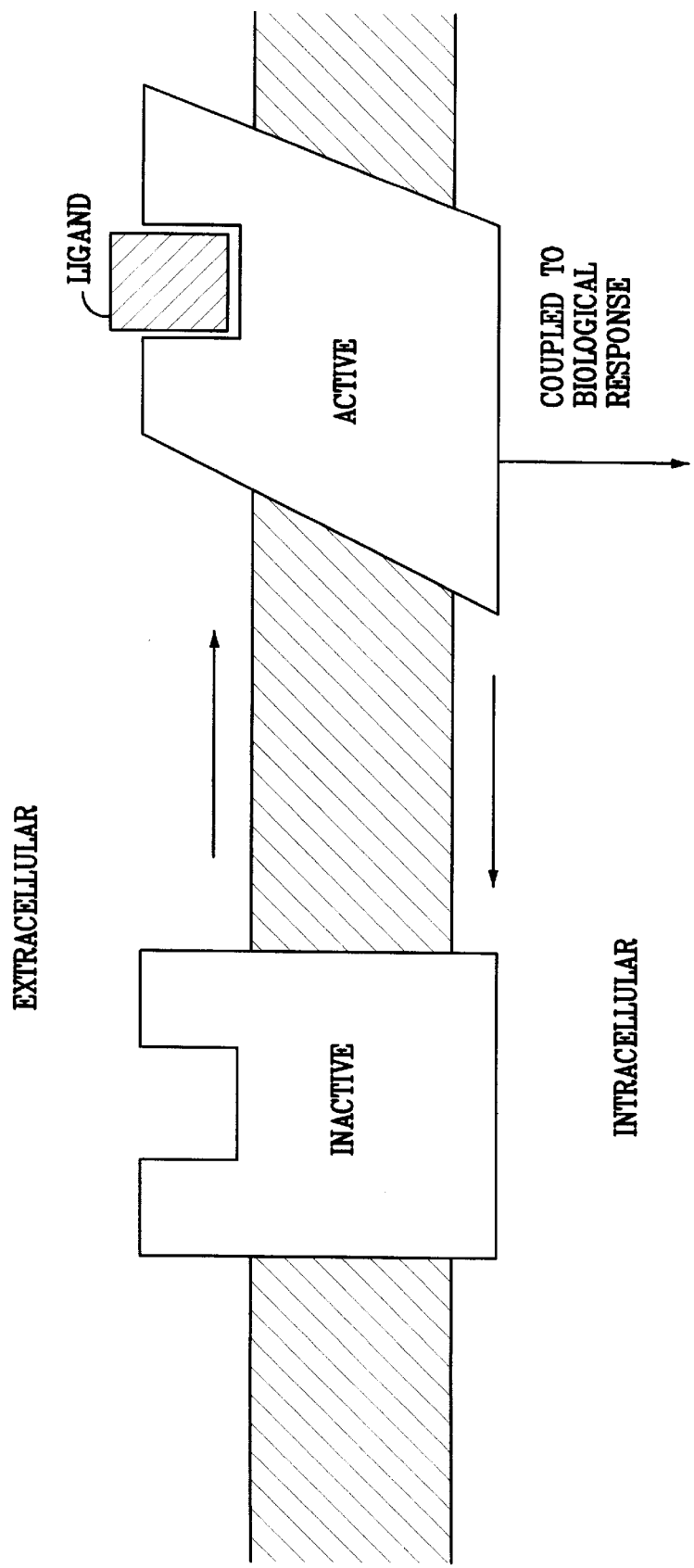
FIG. 2 schematically shows the active and inactive states for a typical G protein-coupled receptor and the linkage of the active state to the second messenger transduction pathway.

The scientific literature that has evolved around receptors has adopted a number of terms to refer to ligands having various effects on receptors. For clarity and consistency, the following definitions will be used throughout this patent document. To the extent that these definitions conflict with other definitions for these terms, the following definitions shall control.

AGONISTS shall mean moieties that activate the intracellular response when they bind to the receptor, or enhance GTP binding to membranes.

AMINO ACID ABBREVIATIONS used herein are set out in Table 1:

TABLE 1

| ALANINE | ALA | A |
| ARGININE | ARG | R |
| ASPARAGINE | ASN | N |
| ASPARTIC ACID | ASP | D |

TABLE 1-continued

| CYSTEINE | CYS | C |
|---|---|---|
| GLUTAMIC ACID | GLU | E |
| GLUTAMINE | GLN | Q |
| GLYCINE | GLY | G |
| HISTIDINE | HIS | H |
| ISOLEUCINE | ILE | I |
| LEUCINE | LEU | L |
| LYSINE | LYS | K |
| METHIONINE | MET | M |
| PHENYLALANINE | PHE | F |
| PROLINE | PRO | P |
| SERINE | SER | S |
| THREONINE | THR | T |
| TRYPTOPHAN | TRP | W |
| TYROSINE | TYR | Y |
| VALINE | VAL | V |

PARTIAL AGONISTS shall mean moieties which activate the intracellular response when they bind to the receptor to a lesser degree/extent than do agonists, or enhance GTP binding to membranes to a lesser degree/extent than do agonists.

ANTAGONIST shall mean moieties that competitively bind to the receptor at the same site as the agonists but which do not activate the intracellular response initiated by the active form of the receptor, and can thereby inhibit the intracellular responses by agonists or partial agonists. ANTAGONISTS do not diminish the baseline intracellular response in the absence of an agonist or partial agonist.

CANDIDATE COMPOUND shall mean a molecule (for example, and not limitation, a chemical compound) which is amenable to a screening technique.

COMPOUND EFFICACY shall mean a measurement of the ability of a compound to inhibit or stimulate receptor functionality, as opposed to receptor binding affinity.

CONSTITUTIVELY ACTIVATED RECEPTOR shall mean a receptor subject to constitutive receptor activation.

CONSTITUTIVE RECEPTOR ACTIVATION shall mean stabilization of a receptor in the active state by means other than binding of the receptor with its endogenous ligand or a chemical equivalent thereof.

CONTACT or CONTACTING shall mean bringing at least two moieties together, whether in an in vitro system or an in vivo system.

ENDOGENOUS shall mean a material that a mammal naturally produces. ENDOGENOUS in reference to, for example and not limitation, the term "receptor" shall mean that which is naturally produced by a mammal (for example, and not limitation, a human) or a virus.

In contrast, the term NON-ENDOGENOUS in this context shall mean that which is not naturally produced by a mammal (for example, and not limitation, a human) or a virus. For example, and not limitation, a receptor which is not constitutively active in its endogenous form, but when manipulated becomes constitutively active, is most preferably referred to herein as a "non-endogenous, constitutively activated receptor." Both terms can be utilized to describe both "in vivo" and "in vitro" systems. For example, and not a limitation, in a screening approach, the endogenous or non-endogenous receptor may be in reference to an in vitro screening system. As a further example and not limitation, where the genome of a mammal has been manipulated to include a non-endogenous constitutively activated receptor, screening of a candidate compound by means of an in vivo system is viable.

INHIBIT or INHIBITING, in relationship to the term "response" shall mean that a response is decreased or prevented in the presence of a compound as opposed to in the absence of the compound.

INVERSE AGONISTS shall mean moieties that bind the endogenous form of the receptor or to the constitutively activated form of the receptor, and which inhibit the baseline intracellular response initiated by the active form of the receptor below the normal base level of activity which is observed in the absence of agonists or partial agonists, or decrease GTP binding to membranes. Preferably, the baseline intracellular response is inhibited in the presence of the inverse agonist by at least 30%, more preferably by at least 50%, and most preferably by at least 75%, as compared with the baseline response in the absence of the inverse agonist.

LIGAND shall mean an endogenous, naturally occurring molecule specific for an endogenous, naturally occurring receptor.

PHARMACEUTICAL COMPOSITION shall mean a composition comprising at least one active ingredient, whereby the composition is amenable to investigation for a specified, efficacious outcome in a mammal (for example, and not limitation, a human). Those of ordinary skill in the art will understand and appreciate the techniques appropriate for determining whether an active ingredient has a desired efficacious outcome based upon the needs of the artisan.

STIMULATE or STIMULATING, in relationship to the term "response" shall mean that a response is increased in the presence of a compound as opposed to in the absence of the compound.

DETAILED DESCRIPTION

I. Particularly preferred mutations

For convenience, the sequence information regarding the non-endogenous, constitutively active human 5-HT2A and 5-HT2C receptors are referred to by identifiers as set forth in Table 2:

TABLE 2

| IDENTIFIER | RECEPTOR | SEQ. ID. NO: | FIGURE |
|---|---|---|---|
| AP-1 cDNA | 5-HT2C | 28 | 5a |
| AP-1 | 5-HT2C | 29 | 5b |
| AP-3 cDNA | 5-HT2A | 30 | 6a |
| AP-3 | 5-HT2A | 31 | 6b |
| AP-4 cDNA | 5-HT2A | 32 | 7a |
| AP-4 | 5-HT2A | 33 | 7b |

As will be discussed in greater detail below, a mutation analogous to that reported by Casey (C322K) was utilized in the human 5-HT2A receptor and is referred to herein as AP-2. However, AP-2 did not lead to sufficient constitutive activation to allow for utilization in screening techniques.

II. Introduction

While it is sometimes possible to make predictions as to the effect of nucleic acid manipulation from one species to another, this is not always the case. The results reported by Casey suggest that a point mutation in the rat 5-HT2A receptor evidences constitutive activation of the mutated receptor. Casey reports that the C322K mutation was approximately four fold more active than the native rat 5-HT2A receptor. However, for purposes of a most preferred use, i.e., screening of candidate compounds, this corresponding mutation in the human 5-HT2A receptor had little discernable effect in evidencing constitutive activation of the human receptor. This, of course, creates the reasonable conclusion that the information reported in Herrick-Davis 1 or Hernick-Davis 2 is of limited predictive value relative to the manipulation of the human 5-HT2C receptor. Consequently, the ability to make reasonable predictions about the effects of mutations to the rat 5-HT receptors vis-a-vis the corresponding human receptors is not possible. Nonetheless, this unfortunate lack of reasonable predictability provides the opportunity for others to discover mutations to the human 5-HT receptors that provide evidence of constitutive activation.

Therefore, the present invention is based upon the desire of defining mutated sequences of the human serotonin receptors 5-HT2A and 5-HT2C whereby such mutated versions of the expressed receptor are constitutively active. These constitutively active receptors allow for, inter alia, screening candidate compounds.

What has been discovered and disclosed herein is that substantial activation of the human 5-HT2A receptor can be obtained by "domain swapping," i.e., by switching the third intracellular domain of the 5-HT2A receptor with the third intracellular domain of the 5-HT2C receptor. Additionally, swapping the cytoplasmic tail of the two receptors further increases the IP3 response. Furthermore, mutation of the serine at position 310 to lysine (S310K) of the human 5-HT2C receptor leads to constitutive activation.

What follows is a most preferred approach to identification of candidate compounds; those in the art will readily appreciate that the particular order of screening approaches, and/or whether or not to utilize certain of these approaches, is a matter of choice. Thus, the order presented below, set for presentational efficiency and for indication of the most preferred approach utilized in screening candidate compounds, is not intended, nor is to be construed, as a limitation on the disclosure, or any claims to follow.

III. Generic G Protein-Coupled Receptor screening assay techniques

When a G protein receptor becomes constitutively active, it binds to a G protein (Gq, Gs, Gi, Go) and stimulates the binding of GTP to the G protein. The G protein then acts as a GTPase and slowly hydrolyzes the GTP to GDP, whereby the receptor, under normal conditions, becomes deactivated. However, constitutively activated receptors continue to exchange GDP to GTP. A non-hydrolyzable analog of GTP, [$^{35}$S]GTPγS, can be used to monitor enhanced binding to membranes which express constitutively activated receptors. It is reported that [$^{35}$S]GTPγS can be used to monitor G protein coupling to membranes in the absence and presence of ligand. An example of this monitoring, among other examples well-known and available to those in the art, was reported by Traynor and Nahorski in 1995. The preferred use of this assay system is for initial screening of candidate compounds because the system is generically applicable to all G protein-coupled receptors regardless of the particular G protein that interacts with the intracellular domain of the receptor.

IV. Confirmation of G Protein-Coupled Receptor site screening assay techniques

Once candidate compounds are identified using the "generic" G protein-coupled receptor assay (i.e. an assay to select compounds that are agonists, partial agonists, or inverse agonists), further screening to confirm that the compounds have interacted at the receptor site is preferred. For example, a compound identified by the "generic" assay may not bind to the receptor, but may instead merely "uncouple" the G protein from the intracellular domain. Thus, by further screening those candidate compounds, which have been identified using a "generic" assay in an agonist and/or antagonist competitive binding assay, further refinement in the selection process is provided.

Lysergic acid diethylamide (LSD) is a well-known agonist of the 5-HT2A and 5-HT2C receptors, while mesulergine is a well-known antagonist to the 5-HT2C receptor. Accordingly, in most preferred embodiments, an agonist (LSD) and/or antagonist (mesulergine) competitive binding assay(s) is used to further screen those compounds selected from the "generic" assay for confirmation of serotonin receptor binding.

V. Specified G Protein assay techniques

The art-accepted physiologically mediated pathway for the human 5-HT2A and 5-HT2C receptors is via Gq. Intracellular accumulation of IP3 can be used to confirm constitutive activation of these types of Gq coupled receptors (see Herrick-Davis-1). As a result, "IP3 accumulation" assays can be used to further screen those compounds selected from an agonist and/or antagonist competitive binding assay.

VI. Pharmaceutical compositions

Candidate compounds selected for further development can be formulated into pharmaceutical compositions using techniques well known to those in the art. Suitable pharmaceutically-acceptable carriers are available to those in the art; for example, see Remington's Pharmaceutical Sciences, 16$^{th}$ Edition, 1980, Mack Publishing Co., (Oslo et al., eds.)

EXAMPLES

The following examples are presented for purposes of elucidation, and not limitation, of the present invention. While specific nucleic acid and amino acid sequences are disclosed herein, those of ordinary skill in the art are credited with the ability to make minor modifications to these sequences while achieving the same or substantially similar results reported below. It is intended that equivalent, non-endogenous, constitutively activated human serotonin receptor sequences having eighty-five percent (85%) homology, more preferably having ninety percent (90%) homology, and most preferably having ninety-five percent (95%) homology to the disclosed and claimed sequences all fall within the scope of any claims appended hereto.

Example 1

GENERATION OF NON-ENDOGENOUS, CONSTITUTIVELY ACTIVATED HUMAN SEROTONiN RECEPTORS 5HT2C AND 5-HT2A

A. Construction of constitutively active 5-HT2C receptor cDNA

1. Endogenous Human 5-HT2C

The cDNA encoding endogenous human 5-HT2C receptor was obtained from human brain poly-A$^+$ RNA by RT-PCR. The 5' and 3' primers were derived from the 5' and 3' untranslated regions and contained the following sequences:

5'-GACCTCGAGGTTGCTTAAGACTGAAGCA-3' (SEQ.ID.NO:1)
5'-ATTTCTAGACATATGTAGCTTGTACCGT-3' (SEQ.ID.NO:2)

PCR was performed using either TaqPlus™ precision polymerase (Stratagene) or rTth™ polymerase (Perkin Elmer) with the buffer systems provided by the manufacturers, 0.25 μM of each primer, and 0.2 mM of each of the four (4) nucleotides. The cycle condition was 30 cycles of 94° C. for 1 minute, 57° C. for 1 minute and 72° C. for 2 minutes. The 1.5 kb PCR fragment was digested with Xho I and Xba I and subcloned into the Sal I-Xba I site of pBluescript.

The derived cDNA clones were fully sequenced and found to correspond to published sequences.

2. AP-1 cDNA

The cDNA containing a S310K mutation (AP-1 cDNA) in the third intracellular loop of the human 5-HT2C receptor was constructed by replacing the Sty I restriction fragment containing amino acid 310 with synthetic double stranded oligonucleotides encoding the desired mutation. The sense strand sequence utilized had the following sequence:

5'-CTAGGGGCACCATGCAGGCTATCAACAATGAA-AGAAAAGCTAAGAAAGTC-3' (SEQ. ID.NO: 3)

and the antisense strand sequence utilized had the following sequence:

5'-CAAGGACTTTCTTAGCTTTTCTTTCATTGTTGA-TAGCCTGCATGGTGCCC-3' (SEQ. ID. NO: 4).

B. Construction of constitutively active 5-HT2A receptor cDNA

1. Endogenous Human 5-HT2A

The cDNA encoding endogenous human 5-HT2A receptor was obtained by RT-PCR using human brain poly-A$^+$ RNA; a 5' primer from the 5' untranslated region with a Xho I restriction site:

5'-GACCTCGAGTCCTTCTACACCTCATC-3' (SEQ.ID.NO:5)

and a 3' primer from the 3' untranslated region containing an Xba I site:

5'-TGCTCTAGATTCCAGATAGGTGAAAACTTG-3' (SEQ.ID.NO:6).

PCR was performed using either TaqPlus™ precision polymerase (Stratagene) or rTth™ polymerase (Perkin Elmer) with the buffer systems provided by the manufacturers, 0.25 μM of each primer, and 0.2 mM of each of the four (4) nucleotides. The cycle condition was 30 cycles of 94° C. for 1 minute, 57° C. for 1 minute and 72° C. for 2 minutes. The 1.5 kb PCR fragment was digested with Xba I and subcloned into the Eco RV-Xba I site of pBluescript.

The resulting cDNA clones were fully sequenced and found to encode two amino acid changes from the published sequences. The first change is a T25N mutation in the N-terminal extracellular domain and the second change is an H452Y mutation. These mutations are likely to represent sequence polymorphisms rather than PCR errors since the cDNA clones having the same two mutations were derived from two independent PCR procedures using Taq polymerase from two different commercial sources (TaqPius™ Stratagene and rTth™ Perkin Elmer).

2. Human 5-TH2A (C322K; AP-2)

The cDNA containing the point mutation C322K in the third intracellular loop was constructed by using the Sph I restriction enzyme site, which encompasses amino acid 322. For the PCR procedure, a primer containing the C322K mutation:

5'-CAAAGAAAGTACTGGGCATCGTCTTCTTCCT-3' (SEQ.ID.NO:7)

was used along with the primer from the 3' untranslated region set forth above as SEQ.ID.NO:6. The resulting PCR fragment was then used to replace the 3' end of the wild type 5-HT2A cDNA by the T4 polymerase blunted Sph I site. PCR was performed using pfu polymerase (Stratagene) with the buffer system provided by the manufacturer and 10% DMSO, 0.25 mM of each primer, 0.5 mM of each of the 4 nucleotides. The cycle conditions were 25 cycles of 94° C. for 1 minute, 60° C. for 1 minute and 72° C. for 1 minute.

3. AP-3 cDNA

The human 5-HT2A cDNA with intracellular loop 3 (IC3) or IC3 and cytoplasmic tail replaced by the corresponding human 5-HT2C cDNA was constructed using PCR-based mutagenesis.

(a) Replacement of IC3 Loop

The IC3 loop of human 5-HT2A cDNA was first replaced with the corresponding human 5-HT2C cDNA. Two separate PCR procedures were performed to generate the two fragments, Fragment A and Fragment B, that fuse the 5-HT2C IC3 loop to the transmembrane 6 (TM6) of 5-HT2A. The 237 bp PCR fragment, Fragment A, containing 5-HT2C IC3 and the initial 13 bp of 5-HT2A TM6 was amplified by using the following primers:

5'-CCGCTCGAGTACTGCGCCGACAAGCTTFGAT-3' (SEQ.ID.NO:8)

5'-CGATGCCCAGCACTTCAAGCTTTTCTTTCATT-GTTG3'(SEQ.ID.NO:9)

The template used was human 5-HT2C cDNA.

The 529 bp PCR fragment, Fragment B, containing the C-terminal 13 bp of IC3 from 5-HT2C and the C-terminal of 5-HT2A starting at beginning of TM6, was amplified by using the following primers:

5'-AAAAGCTTCGAAAGTGCTGGGCATCGTCTTCT-TCCT-3'(SEQ.ID.NO: 10)

5'-TGCTCTAGATTCCAGATAGGTGAAAACTTG-3' (SEQ.ID.NO: 11)

The template used was human 5-HT2A cDNA.

Second round PCR was performed using Fragment A and Fragment B as co-templates with SEQ.ID.NO:8 and SEQ.ID.NO:11 (it is noted that the sequences for SEQ.ID.NOS.: 6 and 11 are the same) as primers. The resulting 740 bp PCR fragment, Fragment C, contained the IC3 loop of human 5-HT2C fused to TM6 through the end of the cytoplasmic tail of human 5-HT2A. PCR was performed using pfu™ polymerase (Stratagene) with the buffer system provided by the manufacturer, and 10% DMSO, 0.25 mM of each primer, and 0.5 mM of each of the four (4) nucleotides. The cycle conditions were 25 cycles of 94° C. for 1 minute, 57° C. (1st round PCR) or 60° C. (2nd round PCR) for 1 minute, and 72° C. for 1 minute (1st round PCR) or 90 seconds. (2nd round PCR).

To generate a PCR fragment containing a fusion junction between the human 5-HT2A TM5 and the IC3 loop of 5-HT2C, four (4) primers were used. The two external primers, derived from human 5-HT2A, had the following sequences:

5'-CGTGTCTCTCCTTACTTCA-3'(SEQ.ID.NO: 12)

The other primer used was SEQ.ID.NO.6 (see note above regarding SEQ.ID.NOS. 6 and 11). The first internal primer utilized was an antisense strand containing the initial 13 bp of IC3 of 5-HT2C followed by the terminal 23 bp derived from TM5 of 5-HT2A:

5'-TCGGCGCAGTACTTTGATAGTTAGAAAGTAG-GTGAT-3'(SEQ.ID.NO:13)

The second internal primer was a sense strand containing the terminal 14 bp derived from TM5 of 5-HT2A followed by the initial 24 bp derived from IC3 of 5-HT2C:

5'-TTCTAACTATCAAAGTACTGCGCCGACAAGCTT-TGATG-3' (SEQ.ID.NO: 14).

PCR was performed using endogenous human 5-HT2A and a co-template, Fragment C, in a 50 ml reaction volume containing 1× pfu buffer, 10% DMSO, 0.5 mM of each of the four (4) nucleotides, 0.25 mM of each external primer (SEQ.ID.NOS. 11 and 12), 0.06 mM of each internal primer (SEQ.ID.NOS. 13 and 14) and 1.9 units of pfu polymerase (Stratagene). The cycle conditions were 25 cycles of 94° C. for 1 minute, 52° C. for 1 minute and 72° C. for 2 minutes and 10 seconds. The 1.3 kb PCR product was then gel purified and digested with Pst I and Eco RI. The resulting 1 kb PstI-Eco RI fragment was used to replace the corresponding fragment in the endogenous human 5-HT2A sequence to generate the mutant 5-HT2A sequence encoding the IC3 loop of 5-HT2C.

(b) Replacement of the cytoplasmic tail

To replace the cytoplasmic tail of 5-HT2A with that of 5-HT2C, PCR was performed using a sense primer containing the C-terminal 22 bp of TM7 of endogenous human 5-HT2A followed by the initial 21 bp of the cytoplasmic tail of endogenous human 5-HT2C:

5'-TTCAGCAGTCAACCCACTAGTCTATACTCTGT-TCAACAAAATT-3' (SEQ.ID.NO: 15)

The antisense primer was derived from the 3' untranslated region of endogenous human 5-HT2C:

5'-ATTTCTAGACATATGTAGCTTGTACCGT-3' (SEQ.ID.NO:16).

The resulting PCR fragment, Fragment D, contained the last 22 bp of endogenous human 5-HT2A TM7 fused to the cytoplasmic tail of endogenous human 5-HT2C. Second round PCR was performed using Fragment D and the co-template was endogenous human 5-HT2A that was previously digested with Acc I to avoid undesired amplification. The antisense primer used was SEQ.ID.NO: 16 (the sequences for SEQ.ID.NOS. 16 and 2 are the same) and the sense primer used was derived from endogenous human 5-HT2A:

5'-ATCACCTACTTTCTAACTA-3'(SEQ.ID.NO:17).

PCR conditions were as set forth in Example 1 B3.(a) for the first round PCR, except that the annealing temperature was 48° C. and the extension time was 90 seconds. The resulting 710 bp PCR product was digested with Apa I and Xba I and used to replace the corresponding Apa I-Xba I fragment of either (a) endogenous human 5-HT2A, or (b) 5-HT2A with 2C IC3 to generate (a) endogenous human 5-HT2A with endogenous human 5-HT2C cytoplasmic tail and (b) AP-3, respectively.

4. AP-4 cDNA

This mutant was created by replacement of the region of endogenous human 5-HT2A from amino acid 247, the middle of TM5 right after $Pro^{246}$, to amino acid 337, the middle of TM6 just before $Pro^{338}$, by the corresponding region of AP-1 cDNA. For convenience, the junction in TM5 is referred to as the "2A-2C junction," and the junction in TM6 is referred to as the "2C-2A junction."

Three PCR fragments containing the desired hybrid junctions were generated. The 5' fragment of 561 bp containing the 2A-2C junction in TM5 was generated by PCR using endogenous human 5-HT2A as template, SEQ.ID.NO:12 as the sense primer, and the antisense primer was derived from 13 bp of 5-HT2C followed by 20 bp of 5-HT2A sequence:

5'-CCATAATCGTCAGGGGAATGAAAAATGACA-CAA-3'(SEQ.ID.NO: 18)

The middle fragment of the 323 bp contains endogenous human 5-HT2C sequence derived from the middle of TM5 to the middle of TM6, flanked by 13 bp of 5-HT2A sequences from the 2A-2C junction and the 2C-2A junction. This middle fragment was generated by using AP-1 cDNA as a template, a sense primer containing 13 bp of 5-HT2A followed by 20 bp of 5-HT2C sequences across the 2A-2C junction and having the sequence:

5'-ATTTTTCATTCCCCTGACGATTATGGTGATTAC-3'(SEQ.ID.NO:19);

and an antisense primer containing 13 bp of 5-HT2A followed by 20 bp of 5-HT2C sequences across the 2C-2A junction and having the sequence:

5'-TGATGAAGAAAGGGCACCACATGATCAGAA-ACA-3'(SEQ.ID.NO:20).

The 3' fragment of 487 bp containing the 2C-2A junction was generated by PCR using endogenous human 5-HT2A as a template and a sense primer having the following sequence from the 2C-2A junction:

5'-GATCATGTGGTGCCCTTTCTTCATCACAAACAT-3'(SEQ.ID.NO:2 1)

and the antisense primer was SEQ.ID.NO:6 see note above regarding SEQ.ID.NOS. 6 and 11).

Two second round PCR reactions were performed separately to link the 5' and middle fragment (5'M PCR) and the middle and 3' fragment (M3' PCR). The 5'M PCR co-template used was the 5' and middle PCR fragment as described above, the sense primer was SEQ.ID.NO:12 and the antisense primer was SEQ.ID.NO:20. The 5'M PCR procedure resulted in an 857 bp PCR fragment.

The M3' PCR used the middle and M3' PCR fragment described above as the co-template, SEQ.ID.NO: 19 as the sense primer and SEQ.ID.NO:6 (see note above regarding SEQ.ID.NOS. 6 and 11) as the antisense primer, and generated a 784 bp amplification product. The final round of PCR was performed using the 857 bp and 784 bp fragments from the second round PCR as the co-template, and SEQ.ID.NO:12 and SEQ.ID.NO: 6 (see note above regarding SEQ.ID.NOS. 6 and 11) as the sense and the antisense primer, respectively. The 1.32 kb amplification product from the final round of PCR was digested with Pst I and Eco RI. Then resulting 1 kb Pst I-Eco RI fragment was used to replace the corresponding fragment of the endogenous human 5-HT2A to generate mutant 5-HT2A with 5-HT2C: C310K/IC3. The Apa I-Xba fragment of AP3 was used to replace the corresponding fragment in mutant 5-HT2A with 5-HT2C: C31OK/IC3 to generate AP4.

Example 2

RECEPTOR EXPRESSION

A. pCMV

Figure 8:
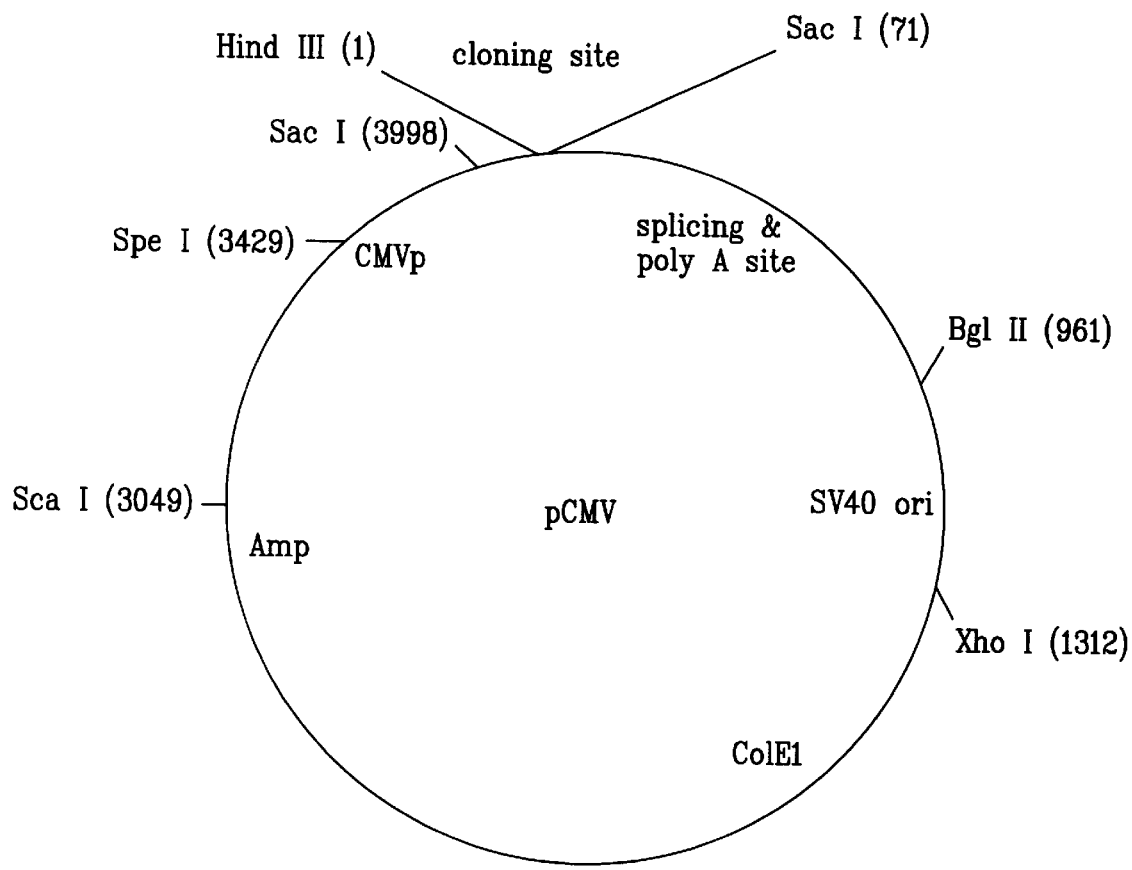
FIG. 8 is a representation of the preferred vector, pCMV, used herein.

Although a variety of expression vectors are available to those in the art, for purposes of utilization for both the endogenous and non-endogenous receptors discussed herein, it is most preferred that the vector utilized be pCMV. This vector was deposited with the American Type Culture Collection (ATCC) on Oct. 13, 1998 (10801 University Blvd., Manassas, Va. 20110-2209 USA) under the provisions of the Budapest Treaty for the International Recognition of the Deposit of Microorganisms for the Purpose of Patent Procedure. The DNA was tested by the ATCC and determined to be viable. The ATCC has assigned the following deposit number to pCMV: ATCC #203351. See FIG. 8.

B. Transfection procedure

For the generic assay ([$^{35}$S]GTPγS; Example 3) and the antagonist binding assay (mesulergine; Example 4), transfection of COS-7 or 293T cells was accomplished using the following protocol.

On day one, 5×10$^6$ COS-7 cells or 1×10$^7$ 293T cells per 150 mm plate were plated out. On day two, two reaction tubes were prepared (the proportions to follow for each tube are per plate): tube A was prepared by mixing 20 µg DNA (e.g., pCMV vector; pCMV vector AP-1 cDNA, etc.) in 1.2 ml serum free DMEM (Irvine Scientific, Irvine, Calif.); tube B was prepared by mixing 120 µl lipofectamine (Gibco BRL) in 1.2 ml serum free DMEM. Tubes A and B were then admixed by inversions (several times), followed by incubation at room temperature for 30–45 min. The admixture is referred to as the "transfection mixture". Plated COS-7 cells were washed with 1× PBS, followed by addition of 10 nm serum free DMEM. 2.4 ml of the transfection mixture was then added to the cells, followed by incubation for 4hrs at 37° C./5% $CO_2$. The transfection mixture was then removed by aspiration, followed by the addition of 25 ml of DMEM/ 10% Fetal Bovine Serum. Cells were then incubated at 37° C./5% $CO_2$. After 72 hr incubation, cells were then harvested and utilized for analysis.

Example 3

GTP MEMBRANE BINDING SCINTILLATION PROXIMITY ASSAY

The advantages of using [$^{35}$S]GTPγS binding to measure constitutive activation are that: (a) [$^{35}$S]GTPγS binding is generically applicable to all G protein-coupled receptors; and (b) [$^{35}$S]GTPγS binding is proximal at the membrane surface, thereby making it less likely to pick-up molecules which affect the intracellular cascade. The assay utilizes the ability of G protein-coupled receptors to stimulate [$^{35}$S] GTPγS binding to membranes expressing the relevant receptors. Therefore, the assay may be used to directly screen compounds at the disclosed serotonin receptors.

Figure 9:
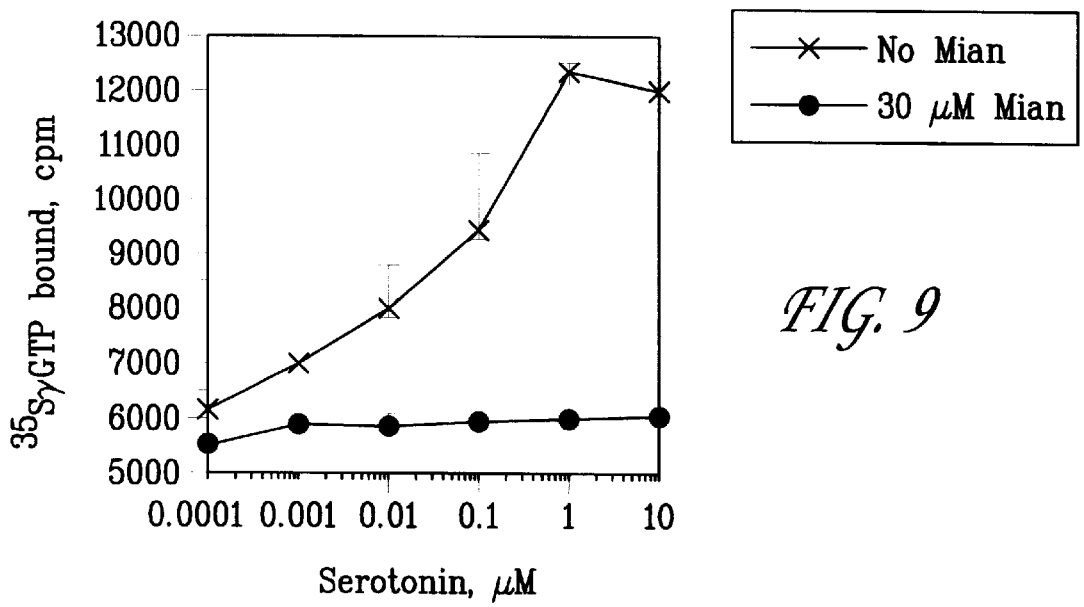
FIG. 9 is a diagram illustrating (1) enhanced [$^{35}$S]GTPγS binding to membranes prepared from COS cells expressing the endogenous human 5-HT2C receptor in response to serotonin, and (2) inhibition by mianserin using wheatgerm agglutinin scintillation proximity beads. The concentration of [$^{35}$S]GTPγS was held constant at 0.3 nM, and the concentration of GDP was held at 1 µM. The concentration of the membrane protein was 12.5 µg.

FIG. 9 demonstrates the utility of a scintillation proximity assay to monitor the binding of [$^{35}$S]GTPγS to membranes expressing the endogenous human 5-HT2C receptor expressed in COS cells. In brief, the assay was incubated in 20 mM HEPES, pH 7.4, binding buffer with 0.3 nM [$^{35}$] GTPγS and 12.5 μg membrane protein and 1 μM GDP for 30 minutes. Wheatgerm agglutinin beads (25 μl; Amersham) were then added and the mixture was incubated for another 30 minutes at room temperature. The tubes were then centrifuged at 1500 ×g for 5 minutes at room temperature and then counted in a scintillation counter. As shown in FIG. 9, serotonin, which as the endogenous ligand activates the 5-HT2C receptor, stimulated [$^{35}$S]GTPγS binding to the membranes in a concentration dependant manner. The stimulated binding was completely inhibited by 30 μM mianserin, a compound considered as a classical 5-HT2C antagonist, but also known as a 5-HT2C inverse agonist.

Although this assay measures agonist-induced binding of [$^{35}$S]GTPγS to membranes and can be routinely used to measure constitutive activity of receptors, the present cost of wheatgerm agglutinin beads may be prohibitive. A less costly but equally applicable alternative also meets the needs of large-scale screening. Flash plates and Wallac™ scintistrips may be used to format a high throughput [$^{35}$S]GTPγS binding assay. This technique allows one to monitor the tritiated ligand binding to the receptor while simultaneously monitoring the efficacy via [$^{35}$S]GTPγS binding. This is possible because the Wallac™ beta counter can switch energy windows to analyze both tritium and $^{35}$S-labeled probes.

Also, this assay may be used for detecting of other types of membrane activation events that result in receptor activation. For example, the assay may be used to monitor $^{32}$P phosphorylation of a variety of receptors (including G protein-coupled and tyrosine kinase receptors). When the membranes are centrifuged to the bottom of the well, the bound [$^{35}$S]GTPγS or the $^{32}$P-phosphorylated receptor will activate the scintillant coated on the wells. Use of Scinti® strips (Wallac™) demonstrate this principle. Additionally, this assay may be used for measuring ligand binding to receptors using radiolabeled ligands. In a similar manner, the radiolabeled bound ligand is centrifuged to the bottom of the well and activates the scintillant The [$^{35}$S]GTPγS assay results parallel the results obtained in traditional second messenger assays of receptors.

Figure 10:
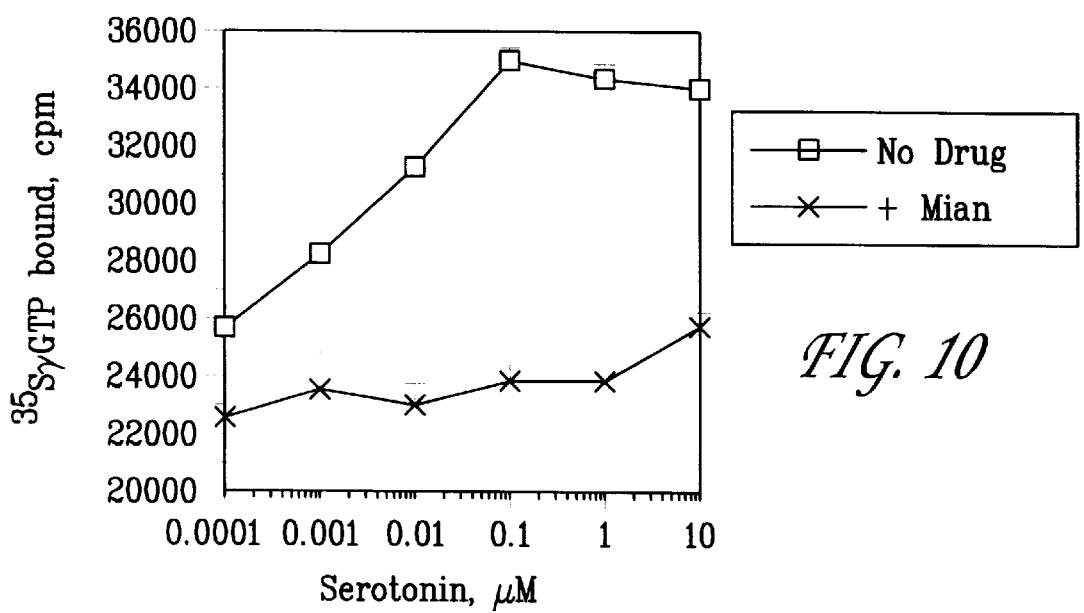
FIG. 10 is a diagram showing serotonin stimulation of [$^{35}$S]GlPγS binding to membranes expressing AP-1 receptors in 293T cells and the inhibition by 30 µM mianserin on Wallac™ scintistrips.

As shown in FIG. 10, serotonin stimulates the binding of [$^{35}$S]GTPγS to the endogenous human 5-HT2C receptor, while mianserin inhibits this response. Furthermore, mianserin acts as a partial inverse agonist by inhibiting the basal constitutive binding of [$^{35}$S]GTPγS to membranes expressing the endogenous human 5-HT2C receptor. As expected, there is no agonist response in the absence of GDP since there is no GDP present to exchange for [$^{35}$S]GTPγS. Not only does this assay system demonstrate the response of the native 5-HT2C receptor, but it also measures the constitutive activation of other receptors.

Figure 11A:
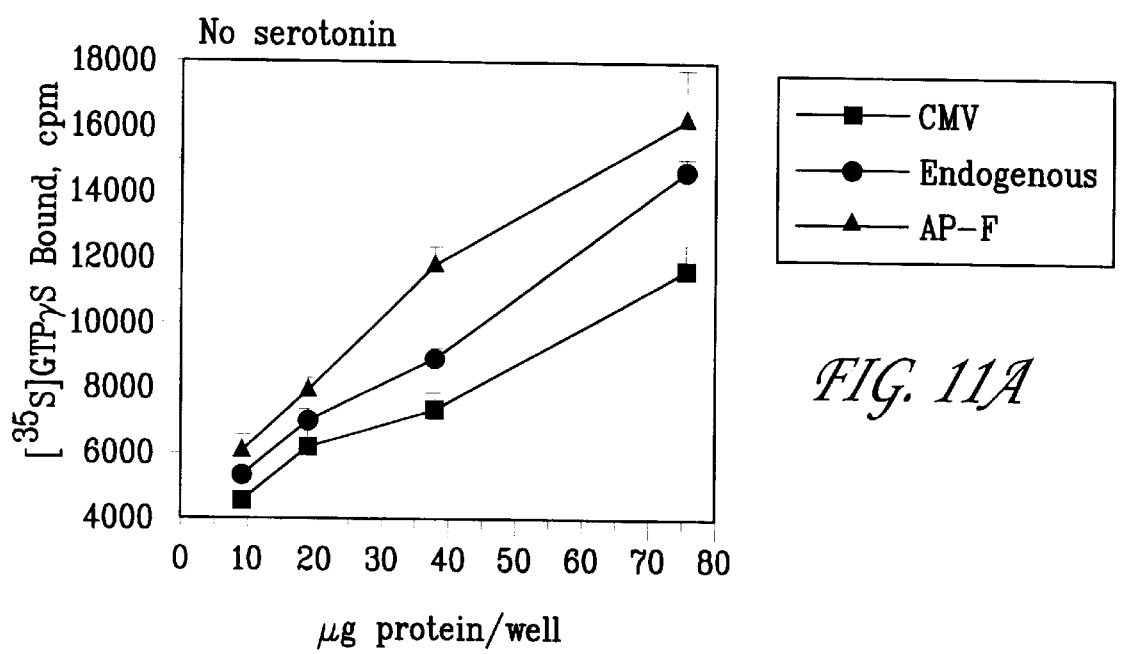
FIG. 11 is a diagram showing the effects of protein concentration on [$^{35}$S]GTPγS binding in membranes prepared from 293T cells transfected with the endogenous human 5-HT2C receptors and AP-1 receptors compared to cells transfected with the control vector (pCMV) alone in the absence (A) and presence (B) of 10 µM serotonin. The radiolableled concentration of [$^{35}$S]GTPγS was held constant at 0.3 nM, and the GDP concentration was held constant at 1 µM. The assay was performed on 96-well format on Wallac™ scintistrips.
Figure 11B:
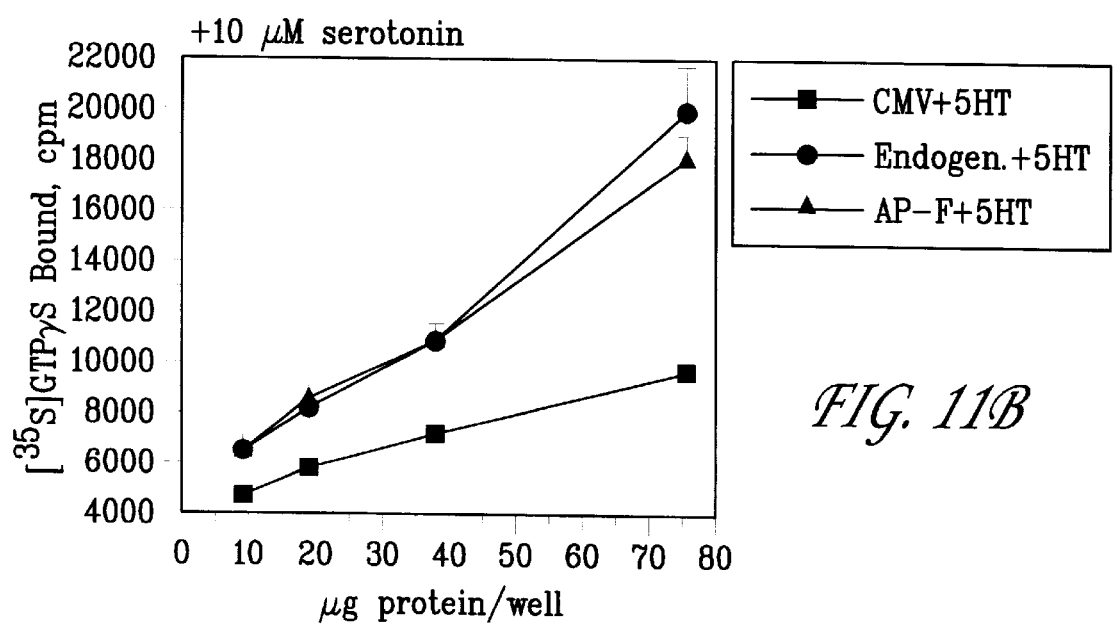

FIG. 11A and FIG. 11B demonstrate the enhanced binding of [$^{35}$S]GTPγS to membranes prepared from 293T cells expressing the control vector alone, the native human 5-HT2C receptor or the AP-1 receptor. The total protein concentration used in the assay affects the total amount of [$^{35}$S]GTPγS binding for each receptor. The c.p.m. Differential between the CMV transfected and the constitutively active mutant receptor increased from approximately 1000 c.p.m at 10 μg/well to approximately 6–8000 c.p.m. at 75 μg/well protein concentration, as shown in FIG. 11.

The AP-1 receptor showed the highest level of constitutive activation followed by the wild type receptor, which also showed enhanced [$^{35}$S]GTPγS binding above basal. This is consistent with the ability of the endogenous human 5-HT2C receptor to accumulate intracellular IP3 in the absence of 5HT stimulation (Example 5) and is also consistent with published data claiming that the endogenous human 5-HT2C receptor has a high natural basal activity. Therefore, the AP-1 receptor demonstrates that constitutive activity may be measured by proximal [$^{35}$S]GTPγS binding events at the membrane interface.

Example 4

SEROTONIN RECEPTOR AGONIST/ANTAGONIST COMPETITIVE BINDING ASSAY

Membranes were prepared from transfected COS-7 cells (see Example 2) by homogenization in 20 mM HEPES and 10 mM EDTA, pH 7.4 and centrifuged at 49,000×g for 15 min. The pellet was resuspended in 20 mM HEPES and 0.1 mM EDTA, pH 7.4, homogenized for 10 sec. using polytron homogenizer (Brinkman) at 5000 rpm and centrifuged at 49,000×g for 15 min. The final pellet was resuspended in 20 mM HEPES and 10 mM $MgCl_2$, pH 7.4, homogenized for 10 sec. using polytron homogenizer (Brinkman) at 5000 rpm.

Assays were performed in triplicate 200 μl volumes in 96 well plates. Assay buffer (20 mM HEPES and 10 mM $MgCl_2$, pH 7.4) was used to dilute membranes, $^3$H-LSD, $^3$H-mesulergine, serotonin (used to define non-specific for LSD binding) and mianserin (used to define non-specific for mesulergine binding). Final assay concentrations consisted of 1 nM $^3$H-LSD or 1 nM $^3$H-mesulergine, 50 μg membrane protein and 100 μm serotonin or mianserin. LSD assays were incubated for 1 hr at 37° C., while mesulergine assays were incubated for 1 hr at room temperature. Assays were terminated by rapid filtration onto Wallac Filtermat Type B with ice cold binding buffer using Skatron cell harvester. The radioactivity was determined in a Wallac 1205 BetaPlate counter.

Example 5

INTRACELLULAR IP3 ACCUMULATION ASSAY

For the IP3 accumulation assay, a transfection protocol different from the protocol set forth in Example 2 was utilized. In the following example, the protocols used for days 1–3 were slightly different for the data generated for FIGS. 12 and 14 and for FIGS. 13 and 15; the protocol for day 4 was the same for all conditions.

A. COS-7 and 293 Cells

On day one, COS-7 cells or 293 cells were plated onto 24 well plates, usually 1×10$^5$ cells/well or 2×10$^5$ cells/well, respectively. On day two, the cells were transfected by first mixing 0.25 μg DNA (see Example 2) in 50 μl serum-free DMEM/well and then 2 μl lipofectamine in 50 μl serum-free DMEM/well. The solutions ("transfection media") were gently mixed and incubated for 15–30 minutes at room temperature. The cells were washed with 0.5 ml PBS and then 400 µl of serum free media was mixed with the transfection media and added to the cells. The cells were then incubated for 3–4 hours at 37° C./5%$CO_2$. Then the transfection media was removed and replaced with 1 ml/well of regular growth media. On day 3, the media was removed and the cells were washed with 0.5 ml PBS. Then 0.5 ml inositol-free/serum-free media (GIBCO BRL) was added to each well with 0.25 µCi of $^3$H-myo-inositol/well and the cells were incubated for 16–18 hours overnight at 37° C./5%$CO_2$. Protocol A.

B. 293 Cells

On day one, 1×10$^7$ 293 cells per 150 mm plate were plated out. On day two, two reaction tubes were prepared (the proportions to follow for each tube are per plate): tube A was prepared by mixing 20 µg DNA (e.g., pCMV vector; pCMV vector AP-1 cDNA, etc.) in 1.2 ml serum free DMEM (Irvine Scientific, Irvine, Calif.); tube B was prepared by mixing 120 µl lipofectamine (Gibco BRL) in 1.2 ml serum free DMEM. Tubes A and B were then admixed by inversions (several times), followed by incubation at room temperature for 30–45 min. The admixture is referred to as the "transfection mixture". Plated 293 cells were washed with 1XPBS, followed by addition of 10 ml serum free DMEM. 2.4 ml of the transfection mixture was then added to the cells, followed by incubation for 4 hrs at 37° C./5% $CO_2$. On day 3, cells were trypsinized and counted, followed by plating of 1×10$^6$ cells/well (poly D-lysine treated 12-well plates). Cells were permitted to adhere to the wells, followed by one wash with 1xPBS. Thereafter, 0.5 µCi $^3$H-inositol in 1 ml inositol-free DMEM was added per well. Protocol B.

On day 4, the cells were washed with 0.5 ml PBS and then 0.45 ml of assay medium was added containing inositol-free/serum free media, 10 µM pargyline, 10 mM lithium chloride, or 0.4 ml of assay medium and 50 µl of 10× ketanserin (ket) to a final concentration of 10 µM. The cells were then incubated for 30 minutes at 37° C. Then the cells were washed with 0.5 ml PBS and 200 ul of fresh/icecold stop solution (1M KOH; 18 mM Na-borate; 3.8 mM EDTA) was added/well. The solution was kept on ice for 5–10 minutes or until the cells were lysed and then neutralized by 200 µl of fresh/ice cold neutralization sol. (7.5% HCL). The lysate was then transferred into 1.5 ml micro-centrifuge tubes and 1 ml of chloroform/methanol (1:2) was added/tube. The solution was vortexed for 15 seconds and the upper phase was applied to a Biorad AG1-X8 anion exchange resin (100–200 mesh). The resin was washed with water and 0.9 ml of the upper phase was loaded onto the column. The column was washed with 10 mls of 5 mM myoinositol and 10 ml of 5 mM Na-borate/60 mM Na-formate. The inositol trisphosphates were eluted into scintillation vials containing 10 ml of scintillation cocktail with 2 ml of 0.1 M formic acid/ 1 M ammonium formate. The columns were regenerated by washing with 10 ml of 0.1 M formic acid/3M ammonium formate and rinsed twice with dd $H_2O$ and stored at room temperature in water. Results are discussed below.

Figure 12:
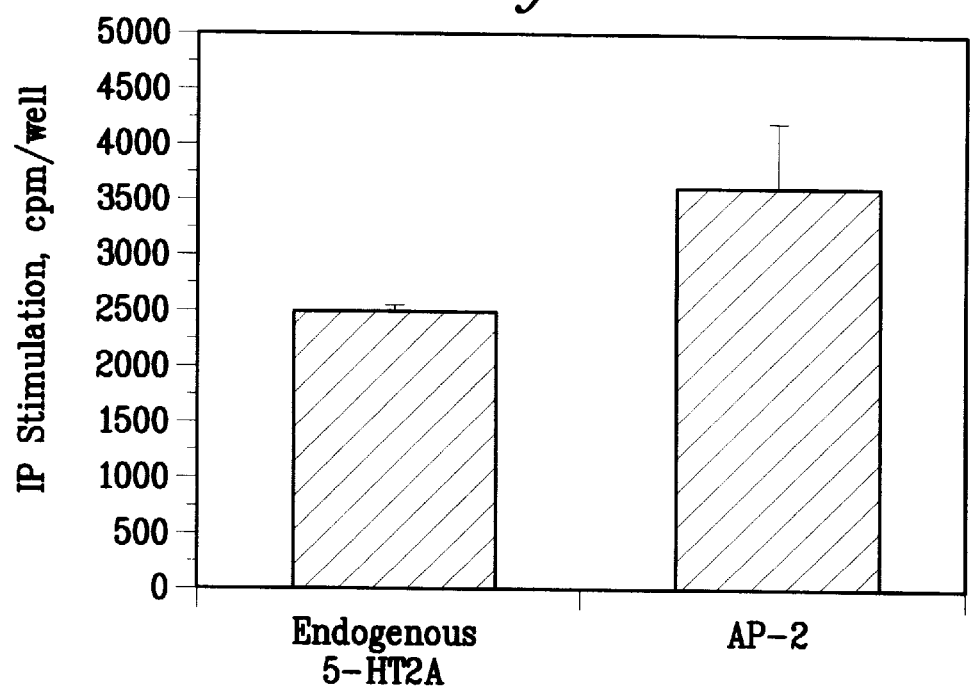
FIG. 12 provides bar-graph comparisons of inositol trisphosphate ("IP3") production between the endogenous human 5HT2A receptor and AP-2, a mutated form of the receptor.

FIG. 12 is an illustration of IP3 production from the human 5-HT2A receptor which was mutated using the same point mutation as set forth in Casey, which rendered the rat receptor constitutively active. The results represented in FIG. 12, support the position that when the point mutation shown to activate the rat receptor is introduced into the human receptor, little activation of the receptor is obtained that would allow for appropriate screening of candidate compounds, with the response being only moderately above that of the endogenous human 5-HT2A receptor. Generally, a response of at least 2× above that of the endogenous response is preferred.

Figure 13:
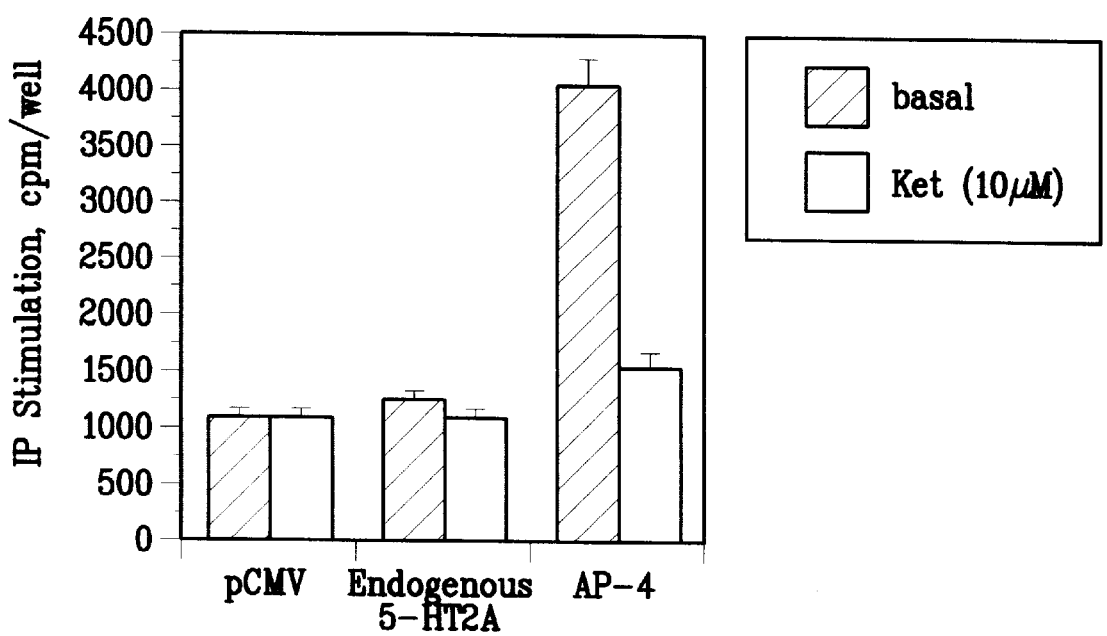
FIG. 13 provides bar-graph comparisons of inositol trisphosphate ("IP3") production between the endogenous human 5HT2A receptor and AP-4, a mutated form of the receptor.

FIG. 13 provides an illustration comparing IP3 production from endogenous 5-HT2A receptor and the AP4 mutation. The results illustrated in FIG. 13 support the position that when the novel mutation disclosed herein is utilized, a robust response of constitutive IP3 accumulation is obtained (e.g., over 2× that of the endogenous receptor).

Figure 14:
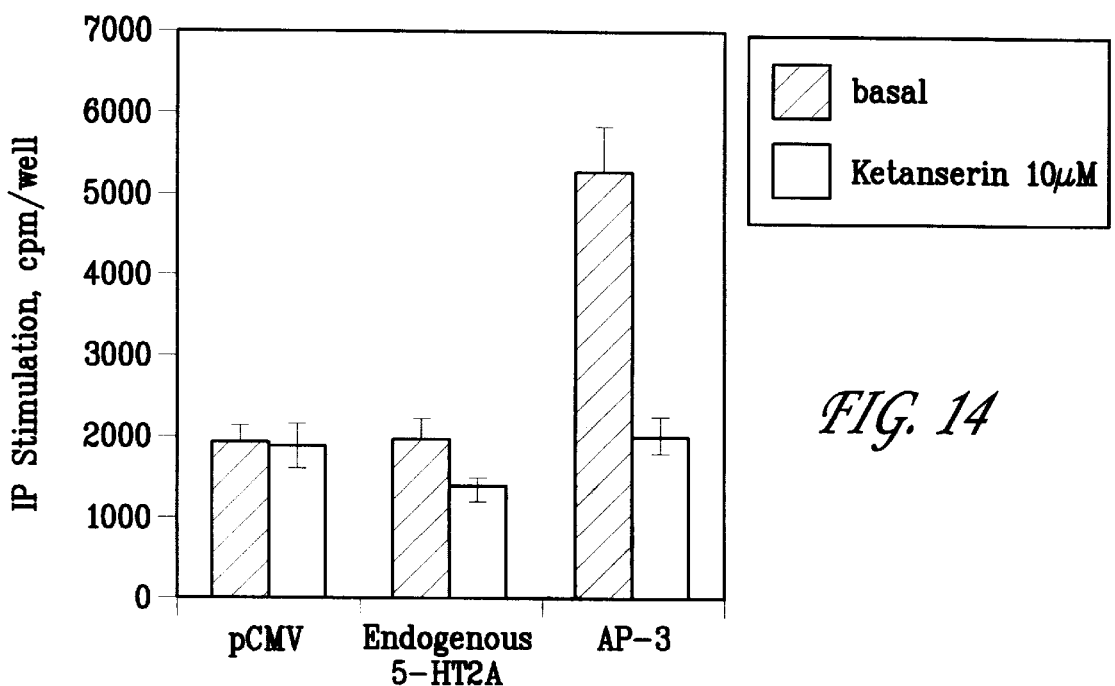
FIG. 14 provides bar graph comparisons of IP3 production between the endogenous human 5-H72A receptor and AP-3, a mutated form of the receptor.

FIG. 14 provides an illustration of IP3 production from AP3. The results illustrated in FIG. 14 support the position that when the novel mutation disclosed herein is utilized, a robust response of constitutive IP3 accumulation is obtained.

Figure 15:
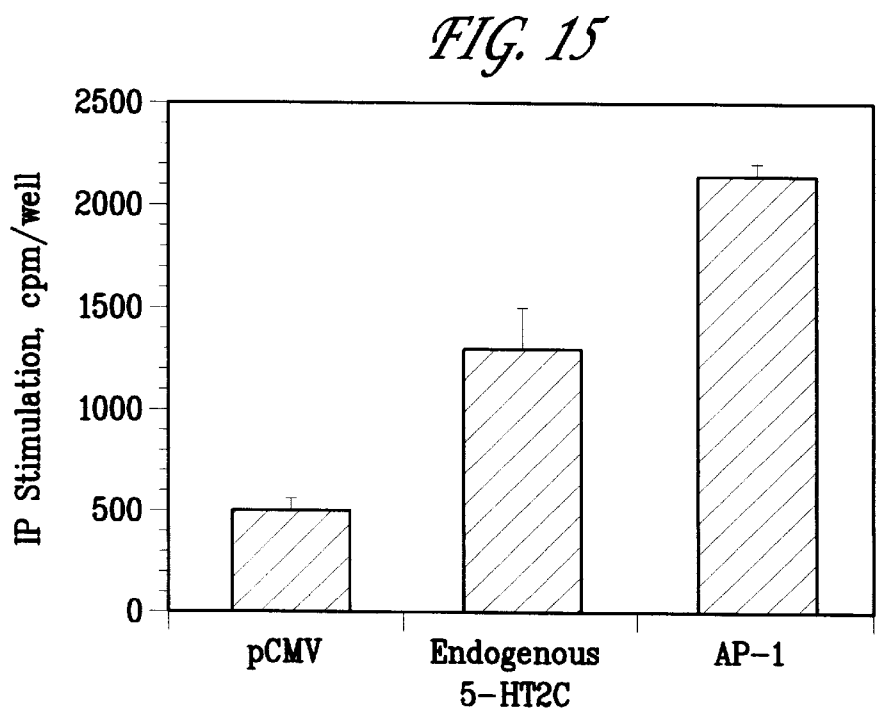
FIG. 15 provides bar-graph comparisons of IP3 production between the endogenous human 5-HT2C receptor and AP-1.

FIG. 15 provides bar-graph comparisons of IP3 accumulation between endogenous human 5-HT2C receptor and AP-1. Note that the endogenous receptor has a high degree of natural constitutive activity relative to the control CMV transfected cells (i.e., the endogenous receptor appears to be constitutively activated).

Example 6

SCREENING OF COMPOUNDS KNOWN TO HAVE 5-HT2C ANTAGONIST ACTIVITY AGAINST NON-ENDOGENOUS, CONSTITUTIVELY ACTIVATED HUMAN SEROTONIN RECEPTOR: AP-1

A final concentration of 12.5 µg membranes prepared from COS7 cells (see Example 2) transiently expressing constitutively active mutant human 5HT2C receptor AP-1 were incubated with binding buffer (20 mM HEPES, pH 7.4, 100 mM NaCl, 20 mM $MgCl_2.6H_2O$, 0.2% saponin, and 0.2 mM ascobate), GDP(1 µM) and compound in a 96-well plate format for a period of 60 minutes at ambient room temperature. Plates were then centrifuged at 4,000 rpm for 15 minutes followed by aspiration of the reaction mixture and counting for 1 minute in a Wallac™ MicroBeta plate scintillation counter. A series of compounds known to possess reported 5HT2C antagonist activity were determined to be active in the [35S]GTPγS binding assay using AP-1. $IC_{50}$ determinations were made for these commercially available compounds (RBI, Natick, Mass.). Results are summarized in Table 3. For each determination, eight concentrations of test compounds were tested in triplicate. The negative control in these experiments consisted of AP-1 receptor without test compound addition, and the positive control consisted of 12.5 µg/well of COS7 cell membranes expressing the CMV promoter without expressed AP-1 receptor.

TABLE 3

| Test Compound | Known Pharmacology | $IC_{50}$ (nM) in GTP-γ-[$^{35}$S] Assay |
|---|---|---|
| Metergoline | 5HT2/1C antagonist | 32.0 |
| Mesulergine | 5HT2/1C antagonist | 21.2 |
| Methysergide | 5HT2/1C antagonist | 6.1 |
| Methiothepin | 5HT1 antagonist | 20.4 |
| Normethylclozapin | 5HT2/1C antagonist | 21.4 |
| Fluoxetine | 5HT reuptake inhibitor | 114.0 |
| Ritanserin | 5HT2/1C antagonist | 19.4 |

The $IC_{50}$ results confirm that the seven tested compounds showed antagonist activity at the AP-1 receptor.

Example 7

SCREENING OF CANDIDATE COMPOUNDS AGAINST NON-ENDOGENOUS, CONSTITUTIVELY ACTIVATED HUMAN SEROTONIN RECEPTORS:AP-1

Approximately 5,500 candidate compounds (Tripos, Inc., St. Louis, Mo.) were screened using the assay protocol of Example 3 (with AP-1 mutant receptor) for identification as inverse agonists against the receptor; for this assay, an arbitrary cut-off of at least 50% inhibition was established for identification of inverse agonists. Approximately 120 of these compounds evidenced at least 50% inhibition of [$^{35}$S]GTPγS binding at 10 μM candidate compound (data not shown).

Example 8

SCREENING OF SELECTED COMPOUNDS TO CONFIRM RECEPTOR BINDING: AP-1

The candidate compounds identified from Example 7 were then screened using the assay protocol of Example 4 (mesulergine), using the AP-1 mutant receptor. IC$_{50}$ (nM) values were determined; five of the nearly 120 compounds of Example 7 were determined to have potent binding affinity for the receptor. Results are summarized in Table 4.

TABLE 4

| Candidate Compound | IC$_{50}$ (nM) in Mesulergine Assay |
| --- | --- |
| 102461 | 205.0 |
| 102788 | 46.5 |
| 100341 | 209.0 |
| 100431 | 147.0 |
| 103487 | 1,810.0 |

Example 9a

GENERAL SCREENING PARADIGM: SELECTION OF PRE-CLINICAL CANDIDATE LEADS

The "primary" screen designed to directly identify human 5HT$_{2A}$/5HT$_{2C}$ receptor inverse agonists consisted of a membrane-based GTPγS binding assay utilizing membranes prepared from COS7 cells transiently transfected with AP-1 human receptor. Candidate compounds (10 μM final assay concentration) directly identified as inhibiting receptor-mediated increases in GTPγS binding by greater than 50–75% (arbitrary cut-off value) were considered active "hits". Primary assay hits were then re-tested in the same assay to reconfirm their inverse agonist activity. If primary assay hits were reconfirmed active (50% or greater inhibition), and therefore directly identified as, e.g., an inverse agonist, one of two approaches were available: (a) socalled "directed libraries" could be created, i.e., additional candidate compounds were synthesized based upon the structures of the reconfirmed hits (geared towards, e.g., improvement in the characteristics of the compounds) whereby the directed library compounds were then evaluated for the ability to compete for radioligand binding to both mutant 5HT2C (AP-1) and endogenous 5HT2A receptors, or (b) the reconfirmed hits were then evaluated for the ability to compete for radioligand binding to both mutant 5HT2C (AP-1) and endogenous 5HT2A receptors. Thus, when approach (a) was used, because these directed library candidate compounds were based upon the structures of compounds that were directly identified from the membrane-based GTPγS binding assay, the directed library compounds were not re-tested in the membrane-based GTPγS binding assay but rather were then confirmed via the radioligand binding analysis. The radioligand binding analysis tests were initially performed at 10 μM test compound in triplicate and if the compound inhibited radiolabeled binding by 50% or more, the analysis was followed by eight concentration competition curves to determine Ki values. The last step in secondary assay evaluation was to determine if test compounds were capable of inhibiting AP-3 receptor-mediated accumulation of inositol phosphates (e.g., IP$_3$). This final assay confirms that the directly identified compounds retained inverse agonist properties.

Example 9b

CONSTITUTIVELY ACTIVATED HUMAN 5HT2C RECEPTOR (AP-1) MEDIATED FACILITATION OF GTPγS BINDING TO COS7 MEMBRANES

This protocol is substantially the same as set forth above in Example 6.

Primary screening assays measuring GTPγS binding to membranes prepared from COS7 cells transiently transfected with human mutated 5HT2C receptor (AP-1) were used to directly identify inverse agonists in screening libraries (Tripos, Inc.). Candidate compound screens were performed in a total assay volume of 200 μl using scintillant-coated Wallac Scintistrip™ plates. The primary assay was comprised of the following chemicals (at indicated final assay concentrations): 20 mM HEPES, pH 7.4, 100 mM NaCl, 20 mM MgCl$_2$, 0.2% saponin, 0.2 mM ascorbic acid, 1 μM GDP, 0.3 nM GTPγ$^{35}$S, and 12.5 μg of the above defined membranes. Incubations were performed for 60 minutes at ambient room temperature. The binding assay incubation was terminated by centrifugation of assay plates at 4,000 rpm for 15 minutes, followed by rapid aspiration of the reaction mixture and counting in a Wallac MicroBeta™ scintillation counter.

Primary screening of candidate compounds initially involved testing of 72 test compounds per assay plate (96-well plates were utilized), at a final assay concentration of 10 μM candidate compound, in single replicates. A total of sixteen wells of each plate were dedicated for an eight concentration clozapine (a confirmed 5HT2C/2A inverse agonist) dose response curve (duplicate determinations at each concentration). Finally, a total of five assay wells of each plate were dedicated to define the negative control (AP-1 receptor expressing membranes without addition of candidate compounds) and three wells from each plate to define the positive control (membranes without AP-1 receptor).

Reconfirmation experiments involve re-testing candidate compounds in the same assay described above, except that candidate compounds were evaluated in triplicate, thus allowing evaluation of 24 compounds per 96-well assay plate. Similar to the primary assay plates, an eight concentration clozapine dose response curve (duplicate determinations at each concentration) and the same negative and positive control wells were also included within each 96-well plate.

Example 9c(1)

COMPETITION STUDIES MUTATED HUMAN 5HT2C RECEPTOR (AP-1)

Radioligand binding competition experiments were performed in a total assay volume of 200 μl using standard 96-well microtiter plates. The final assay ingredients consisted of assay buffer (20 mM HEPES and 10 nM MgCl$_2$), 1 nM [$^3$H]mesulergine, and 50 μg of membranes (COS7 with AP-1 as defined above). Nonspecific [$^3$H]mesulergine binding was defined in the presence of 100 μM mianserin. Incubations were performed for 1 hour at 37° C. Receptor bound radioligand was resolved from free radioligand by rapid filtration of the assay mixture over a Wallac Filtermat™ Type B filter, followed by washing with ice-cold assay buffer using a Skatron™ cell harvester. Radioactivity was counted using a Wallac 1205 BetaPlate™ counter. Each assay plate contained five negative control wells (membranes expressing receptor and no candidate compound addition) and three positive control wells (each containing 100 μM mianserin). For one concentration tests, candidate compounds were diluted into assay buffer and screened at a final concentration of 10 μM, in triplicate. For $IC_{50}$ determinations, candidate compounds were diluted in assay buffer and eight different concentrations were evaluated, in triplicate. A total of 16 wells were designated for an eight concentration mianserin dose response curve evaluation for both assays.

Example 9c(2)

COMPETITION STUDIES WILD TYPE HUMAN 5HT2A RECEPTOR

Radioligand binding competition experiments were performed in a total assay volume of 200 μl using standard 96-well microtiter plates. The final assay ingredients comprised assay buffer (20 mM HEPES and 10 mM $MgCl_2$), 1 nM [$^3$H]SD, and 50 μg of the above-defined membranes (COS7 with AP-1). Nonspecific [$^3$H]LSD binding was defined in the presence of 100 μM serotonin. Incubations were performed for 1 hour at 37° C. Receptor bound radioligand was resolved from free radioligand by rapid filtration of the assay mixture over a Wallac Filtermat™ Type B filter, followed by washing with ice-cold assay buffer using a Skatron™ cell harvester. Radioactivity was counted using a Wallac 1205 BetaPlate™ counter. Each assay plate contained five negative control wells (membranes expressing receptor and no candidate compound addition) and three positive control wells (containing 100 μM mianserin). For one concentration tests, candidate compounds were diluted into assay buffer and screened at a final concentration of 10 μM in triplicate. For $IC_{50}$ determinations, candidate compounds were diluted in assay buffer and eight different concentrations were evaluated in triplicate. A total of 16 wells were designated for an eight concentration serotonin dose response curve evaluation for both assays.

Example 9d

RECEPTOR-MEDIATED INOSITOL PHOSPHATE ACCUMULATION

Candidate compound identified in the assays of Examples 9a–9c were then evaluated for inositol phosphate accumulation, following the protocol of Example 5 (COS7 cells expressing human mutated 5HT2A receptor, AP-3), modified as follows: tube A was prepared by mixing 16 μg DNA (e.g., pCMV vector; pCMV vector AP-1 cDNA, etc.) in 1.0 ml serum free DMEM (Irvine Scientific, Irvine, Calif.); tube B was prepared by mixing 60 μl lipofectamine (Gibco BRL) in 1.0 ml serum free DMEM. Tubes A and B were then admixed by inversions (several times), followed by incubation at room temperature for 30 min. The admixture is referred to as the "transfection mixture". Plated 293 cells were washed with 10 ml Serum Free DMEM, followed by addition of 11 ml Serum Free DMEM. 2.0 ml of the transfection mixture was then added to the cells, followed by incubation for 5 hrs at 37° C./5% $CO_2$. On day 3, cells were trypsinized and counted, followed by plating of $1 \times 10^6$ cells/well (12-well plates). Cells were permitted to adhere to the wells for 3 hrs., followed by one wash with 1×PBS. Thereafter, 0.5 μCi $^3$H-inositol in 1 ml inositol-free DMEM was added per well.

On day 4, the cells were washed with 1.5 ml PBS and then 0.9 ml of assay medium was added containing inositol-free/serum free media, 10 μM pargyline, 10 mM lithium chloride, for 5 min in 37° C./5% $CO_2$ followed by 100 μl addition of candidate compound diluted in the same material. The cells were then incubated for 120 minutes at 37° C. Then the cells were washed with 1.5 ml PBS and 200 μl of fresh/icecold stop solution (1 M KOH; 18 mM Na-borate; 3.8 mM EDTA) was added/well. The solution was kept on ice for 5–10 minutes or until the cells were lysed and then neutralized by 200 μl of fresh/ice cold neutralization sol. (7.5% HCL). The lysate was then transferred into 1.5 ml micro-centrifuge tubes and 1 ml of chloroform/methanol (1:2) was added/tube. The solution was vortexed for 15 seconds and the upper phase was applied to a Biorad AG1-X8 anion exchange resin (100–200 mesh). The resin was washed with water and 0.9 ml of the upper phase was loaded onto the column. The column was washed with 10 mls of 5 mM myoinositol and 10 ml of 5 mM Na-borate/60 mM Na-formate. The inositol trisphosphates were eluted into scintillation vials containing 10 ml of scintillation cocktail with 2 ml of 0.1 M formic acid/1 M ammonium formate. The columns were regenerated by washing with 10 ml of 0.1 M formic acid/3M ammonium formate and rinsed twice with dd $H_2O$ and stored at room temperature in water.

Following this round of assaying, candidate compounds having an $IC_{50}$ value of less than 10 μM were considered as potential leads for the development of pharmaceutical compositions.

SCREENING CANDIDATE COMPOUNDS

Following the protocols set forth above, one compound, 103487 (Example 8, supra) evidenced the following results:

| Figure Number | GTPγS AP-1 Percent Inhibition Relative To Positive Control (Primary) | GTPγS AP-1 Percent Inhibition Relative To Positive Control (Reconfirm) | Competitive Binding AP-1 ([$^3$H]mesulergine) $IC_{50}$ Value (nM) | Competitive Binding WT 5HT2A ([$^3$H]LSD) $IC_{50}$ Value (nM) | Inositol Phosphate Accumulation AP-3 $IC_{50}$ Value (nM) |
|---|---|---|---|---|---|
| 15A (103487) | −1% | 31% | 2100 850 | 46 | 52 90 |

Based upon these results, structure activity analysis of the 103487 compound suggested that a series of derivatives of 3-(4-bromo-1-methylpyrazole-3-yl)phenylamine would exhibit similar 5-HT$_{2A}$ activity and selectivity. A series of derivatives of 3-(4-bromo-1-methylpyrazole-3-yl) phenylamine have now been synthesized. These "directed" library compounds (Tripos, Inc.) were then analyzed in accordance with the protocols of Examples 9c(1), 9c(2) and 9d.

This series of compounds exhibits highly selective 5-HT$_{2A}$ activity. Accordingly, in the first aspect of the invention, a series of compounds possessing 5-HT$_{2A}$ receptor activity that are useful as inverse agonists at such receptors is designated by the general formula (A):

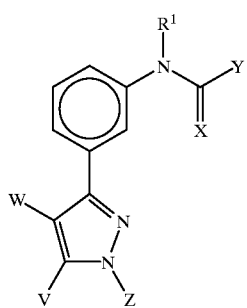

(A)

Wherein:
W is lower alkyl (C$_{1-6}$), or halogen;
V is lower alkyl (C$_{1-6}$), or halogen;
X is either Oxygen or Sulfur;
Y is NR$^2$R$^3$, or (CH$_2$)$_m$R$^4$, or O(CH$_2$)$_n$R$^4$;
Z is lower alkyl (C$_{1-6}$);
m=0–4
n=0–4
R$^1$ is H or lower alkyl (C$_{1-4}$);
R$^2$ is H or lower alkyl(C$_{1-4}$);
R$^3$ and R$^4$ are independently a C$_{1-6}$ alkyl, or C$_{2-6}$ alkenyl, or cycloalkyl, or aryl group and each said group may be optionally substituted by up to four substituents in any position independently selected from CF$_3$, CCl$_3$, Me, NO$_2$, OH, OMe, OEt, CONR$^5$R$^6$, NR$^5$R$^6$, OCF$_3$, SMe, COOR$^7$, SO$_2$NR$^5$R$^6$, SO$_3$R$^7$, COMe, COEt, CO-lower alkyl, SCF$_3$CN, C$_{2-6}$ alkenyl, H, halogens, C$_{1-4}$ alkoxy, C$_{3-6}$ cycloalkyl, C$_{1-6}$ alkyl, aryl, and aryloxy wherein each of the C$_{3-6}$ cycloalkyl, C$_{1-6}$ alkyl, aryl, or aryloxy groups may be further optionally substituted by up to four substituents in any position independently selected from CF$_3$, CCl$_3$, Me, NO$_2$, OH, OMe, OEt, CONR$^5$R$^6$, NR$^5$R$^6$, NHCOCH$_3$, OCF3, SMe, COOR$^7$, SO$_3$R$^7$, SO$_2$NR$^5$R$^6$, COMe, COEt, CO-lower alkyl, SCF$_3$, CN, C$_{2-6}$ alkenyl, H, halogens, C$_{1-4}$ alkoxy, C$_{3-6}$ cycloalkyl, C$_{1-6}$ alkyl, and aryl;

R$^5$ and R$^6$ are independently a H, or C$_{1-6}$ alkyl, or C$_{2-6}$ alkenyl, or cycloalkyl, or aryl, or CH$_2$ aryl group and each said group may be optionally substituted by up to four substituents in any position independently selected from CF$_3$, CCl$_3$, Me, NO$_2$, OH, OMe, OEt, CONR$^7$R$^8$, NR$^7$R$^8$, NHCOCH$_3$, OCF$_3$, SMe, COOR$^9$, SO$_3$R$^7$, SO$_2$NR$^8$R$^8$, COMe, COEt, CO-lower alkyl, SCF$_3$, CN, C$_{2-6}$ alkenyl, H, halogens, C$_{1-4}$ alkoxy, C$_{3-6}$ cycloalkyl, C$_{1-6}$ alkyl, and aryl wherein each of the C$_{3-6}$ cycloalkyl, C$_{1-6}$ alkyl, oraryl groups may be further optionally substituted by up to four substituents in any position independently selected from CF$_3$, CCl$_3$, Me, NO$_2$, OH, OMe, OEt, CONR$^8$R$^8$, NR$^8$R$^9$, NHCOCH$_3$, OCF$_3$, SMe, COOR$^7$, SO$_2$NR$^8$R$^9$, SO$_3$R$^7$, COMe, COEt, CO-lower alkyl, SCF$_3$, CN, C$_{2-6}$ alkenyl, H, halogens, C$_{1-4}$ alkoxy, C$_{3-4}$ cycloalkyl, C$_{1-4}$ alkyl, and aryl, or R$^5$ and R$^6$ may form part of a 5, 6 or 7 membered cyclic structure which may be either saturated or unsaturated and that may contain up to four heteroatoms selected from O, N or S and said cyclic structure may be optionally substituted by up to four substituents in any position independently selected from CF$_3$, CCl$_3$, Me, NO$_2$, OH, OMe, OEt, OCF$_3$, SMe, COOR$^7$, SO$_2$NR$^8$R$^9$, SO$_3$R$^7$, NHCOCH$_3$, COEt, COMe, or halogen;

R$^7$ may be independently selected from H or C$_{1-6}$ alkyl;
R$^8$ and R$^9$ are independently a H, or C$_{1-6}$ alkyl, or C$_{2-6}$ alkenyl, or cycloalkyl, or aryl, or CH$_2$aryl group and each said group may be optionally substituted by up to four substituents in any position independently selected from halogen, CF$_3$, OCF3, OEt, CCl$_3$, Me, NO$_2$, OH, OMe, SMe, COMe, CN, COOR$^7$, SO$_3$R$^7$, COEt, NHCOCH$_3$, or aryl;

an aryl moiety can be a 5 or 6 membered aromatic heterocyclic ring (containing up to 4 hetero atoms independently selected from N, O, or S) or a 6 membered aromatic non-heterocyclic ring or a polycycle;

C$_{1-6}$ alkyl moieties can be straight chain or branched;
optionally substituted C$_{1-6}$ alkyl moieties can be straight chain or branched;
C$_{2-6}$ alkenyl moieties can be straight chain or branched; and
optionally substituted C$_{2-6}$ alkenyl moieties can be straight chain or branched.

Examples of suitable C$_{1-4}$ alkyl groups include but art not limited to methyl, ethyl, n-propyl, i-propyl, n-butyl, and t-butyl.

Halogens are typically F, Cl, Br, and I.

Examples of 5 or 6 membered ring moieties include, but are not restricted to, phenyl, firanyl, thienyl, imidazolyl, pyridyl, pyrrolyl, oxazolyl, isoxazolyl, triazolyl, pyrazolyl, tetrazolyl, thiazolyl and isothiazolyl. Examples of polycycle moieties include, but are not restricted to, naphthyl, benzothiazolyl, benzofuranyl, benzimidazolyl, quinolyl, isoquinolyl, indolyl, quinoxalinyl, quinazolinyl and benzothienyl.

A more preferred series of compounds possessing 5-HT$_{2A}$ receptor activity that are useful as inverse agonists at such receptors is designated by the general formula (B):

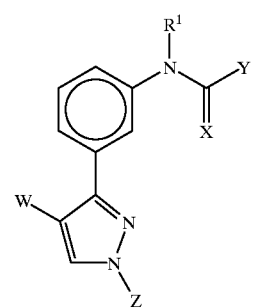

(B)

Wherein:
W is Me, or Et, or halogen;
X is either Oxygen or Sulfur;
Y is NR$^2$R$^3$, or (CH$_2$)$_m$R$^4$, or O(CH$_2$)$_n$R$^4$;
Z is lower alkyl (C$_{1-6}$);
m=0–4
n=0–4
R$^1$ is H or lower alkyl (C$_{1-4}$);
R$^2$ is H or lower alkyl(C$_{1-4}$);

R³ and R⁴ are independently a $C_{1-6}$ alkyl, or $C_{2-6}$ alkenyl, or cycloalkyl, or aryl group and each said group may be optionally substituted by up to four substituents in any position independently selected from $CF_3$, $CCl_3$, Me, $NO_2$, OH, OMe, OEt, $CONR^5R^6$, $NR^5R^6$, $OCF_3$, SMe, $COOR^7$, $SO_2NR^5R^6$, $SO_3R^7$, COMe, COEt, CO-lower alkyl, $SCF_3CN$, $C_{2-6}$ alkenyl, H, halogens, $C_{1-4}$ alkoxy, $C_{3-6}$ cycloalkyl, $C_{1-6}$ alkyl, aryl, and aryloxy wherein each of the $C_{3-6}$ cycloalkyl, $C_{1-6}$ alkyl, aryl, or aryloxy groups may be further optionally substituted by up to four substituents in any position independently selected from $CF_3$, $CCl_3$, Me, $NO_2$, OH, OMe, OEt, $CONR^5R^6$, $NR^5R^6$, $NHCOCH_3$, OCF3, SMe, $COOR^7$, $SO_3R^7$, $SO_2NR^5R^6$, COMe, COEt, CO-lower alkyl, $SCF_3$, CN, $C_{2-6}$ alkenyl, H, halogens, $C_{1-4}$ alkoxy, $C_{3-6}$ cycloalkyl, $C_{1-6}$ alkyl, and aryl;

R⁵ and R⁶ are independently a H, or $C_{1-6}$ alkyl, or $C_{2-6}$ alkenyl, or cycloalkyl, or aryl, or $CH_2$ aryl group and each said group may be optionally substituted by up to four substituents in any position independently selected from $CF_3$, $CCl_3$, Me, $NO_2$, OH, OMe, OEt, $CONR^7R^8$, $NR^7R^8$, $NHCOCH_3$, $OCF_3$, SMe, $COOR^9$, $SO_3R^7$, $SO_2NR^7R^8$, COMe, COEt, CO-lower alkyl, $SCF_3$, CN, $C_{2-6}$ alkenyl, H, halogens, $C_{1-4}$ alkoxy, $C_{3-6}$ cycloalkyl, $C_{1-6}$ alkyl, and aryl wherein each of the $C_{3-6}$ cycloalkyl, $C_{1-6}$ alkyl, oraryl groups may be further optionally substituted by up to four substituents in any position independently selected from $CF_3$, $CCl_3$, Me, $NO_2$, OH, OMe, OEt, $CONR^8R^9$, $NR^8R^9$, $NHCOCH_3$, $OCF_3$, SMe, $COOR^7$, $SO_2NR^8R^9$, $SO_3R^7$, COMe, COEt, CO-lower alkyl, $SCF_3$, CN, $C_{2-6}$ alkenyl, H, halogens, $C_{1-4}$ alkoxy, $C_{3-6}$ cycloalkyl, $C_{1-6}$ alkyl, and aryl, or R⁵ and R⁶ may form part of a 5, 6 or 7 membered cyclic structure which may be either saturated or unsaturated and that may contain up to four heteroatoms selected from O, N or S and said cyclic structure may be optionally substituted by up to four substituents in any position independently selected from $CF_3$, $CCl_3$, Me, $NO_2$, OH, OMe, OEt, $OCF_3$, SMe, $COOR^7$, $SO_2NR^8R^9$, $SO_3R^7$, $NHCOCH_3$, COEt, COMe, or halogen;

R⁷ may be independently selected from H or $C_{1-6}$ alkyl;

R⁸ and R⁹ are independently a H, or $C_{1-4}$ alkyl, or $C_{2-6}$ alkenyl, or cycloalkyl, or aryl, or $CH_2$aryl group and each said group may be optionally substituted by up to four substituents in any position independently selected from halogen, $CF_3$, OCF3, OEt, $CCl_3$, Me, $NO_2$, OH, OMe, SMe, COMe, CN, $COOR^7$, $SO_3R^7$, COEt, $NHCOCH_3$, or aryl;

an aryl moiety can be a 5 or 6 membered aromatic heterocyclic ring (containing up to 4 hetero atoms independently selected from N, O, or S) or a 6 membered aromatic non-heterocyclic ring or a polycycle;

$C_{1-6}$ alkyl moieties can be straight chain or branched;

optionally substituted $C_{1-6}$ alkyl moieties can be straight chain or branched;

$C_{2-6}$ alkenyl moieties can be straight chain or branched; and optionally substituted $C_{2-4}$ alkenyl moieties can be straight chain or branched.

Examples of suitable $C_{1-4}$ alkyl groups include but art not limited to methyl, ethyl, n-propyl, i-propyl, n-butyl, and t-butyl.

Halogens are typically F, Cl, Br, and I.

Examples of 5 or 6 membered ring moieties include, but are not restricted to, phenyl, furanyl, thienyl, imidazolyl, pyridyl, pyrrolyl, oxazolyl, isoxazolyl, triazolyl, pyrazolyl, tetrazolyl, thiazolyl and isothiazolyl. Examples of polycycle moieties include, but are not restricted to, naphthyl, benzothiazolyl, benzofuranyl, benzimidazolyl, quinolyl, isoquinolyl, indolyl, quinoxalinyl, quinazolinyl and benzothienyl.

A first series of compounds having 5-$HT_{2A}$ receptor activity is represented by a class (I) of compounds of formula (B) wherein Y=$NR^2R^3$:

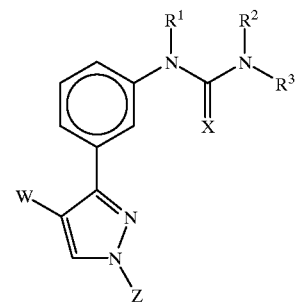

(I)

Wherein:

Preferably R¹ and R² are H.

Preferably W is Br.

Preferably X is O.

Preferably Z is Me.

Preferably R3 is 4-trifluoromethoxyphenyl or 4-trifluoromethoxybenzyl.

Preferred compounds are:

103487

N-[3-(4-bromo-1-methylpyrazol-3-yl)phenyl][{(4-trifluoromethoxy)phenyl}amino]carboxamide

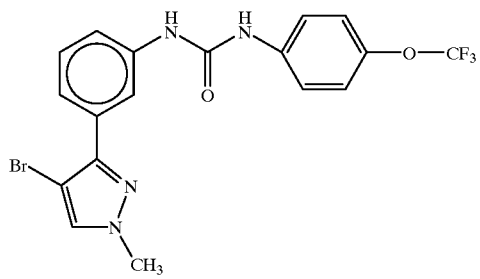

116115

N-[3-(4-bromo-1-methylpyrazol-3-yl)phenyl][{(4-trifluoromethoxy)phenyl)methyl}amino]carboxamide

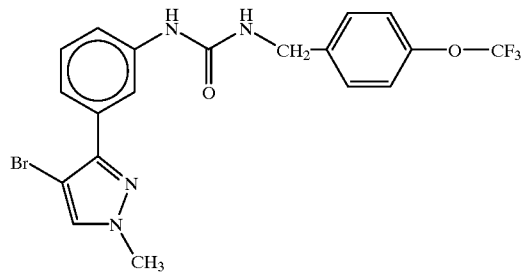

These two compounds demonstrated the following activities using the assay protocols defined in the Examples above:

| Compound Number | Competitive Binding AP-1 ([$^3$H]mesulergine) IC$_{50}$ Value ($\mu$M) | Competitive Binding WT 5HT$_{2A}$ ([$^3$H]LSD) IC$_{50}$ Value ($\mu$M) | Inositol Phosphate Accumulation AP-3 IC$_{50}$ Value ($\mu$M) |
|---|---|---|---|
| 103487 | 2.1 | .046 | .052 |
| 116115 | 1.2 | .45 | .0171 |

Additional compounds of formula (B) wherein Y=NR$^2$R$^3$ are set forth below. Inositol phosphate accumulation assays evidence the activity of test compounds. Both single concentration percentages of control values and IC$_{50}$ determinations indicate activity. In the tables below the column legends have the following meanings:

IP$_3$ % Contol: The values in this column reflect an IP Accumulation Assay where the test compounds were evaluated at one concentration of 10 $\mu$M. For these assays, the compound was diluted into inositol-free Dulbecco's Eagle Media containing 10 $\mu$M pargyline and 10 mM LiCl and tested at a final assay concentration of 10 $\mu$M, in triplicate. The percent control value was calculated based on the control in which no test compound was added.

IP$_3$ AP-3 IC$_{50}$ nM: The values in this column reflect an IP accumulation assay in which the test compound was evaluated at several different concentrations whereby an IC$_{50}$ could be determined. This column corresponds to the column appearing in the tables above which is labeled: Inositol Phosphate Accumulation, AP-3, IC$_{50}$ Value ($\mu$M).

WT 5HT$_{2A}$ LSD IC$_{50}$ nM: The values in this column reflect a competitive binding assay using LSD. This column corresponds to the column appearing in the tables above which is labeled: Competitive Binding, WT 5HT$_{2A}$, ([$^3$H] LSD), IC$_{50}$ Value ($\mu$M).

Compounds listed in each of the following tables reference the structures immediately preceding the table. A "dash" in the table indicates that no value was determined.

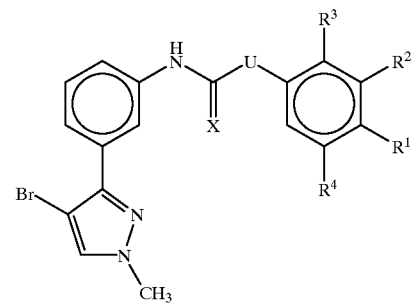

| Compound No. | R$^1$ | R$^2$ | R$^3$ | R$^4$ | X | U | IP$_3$ % of Control | IP$_3$ AP-3 IC$_{50}$ nM | WT 5HT$_{2A}$ LSD IC$_{50}$ nM |
|---|---|---|---|---|---|---|---|---|---|
| N-(3-(4-bromo-1-methylpyrazol-3-yl)phenyl][(4-methylthiophenyl)amino]carboxamide | | | | | | | | | |
| 116079 | SCH$_3$ | H | H | H | O | NH | 16 | 17 | 4 |
| N-[3-(4-bromo-1-methylpyrazol-3-yl)phenyl][(4-chlorophenyl)amino]carboxamide | | | | | | | | | |
| 116081 | Cl | H | H | H | O | NH | 10 | 3.2 | 11 |
| {[3-(4-bromo-1-methylpyrazol-3-yl)phenyl]amino}N-(4-fluorophenyl)carboxamide | | | | | | | | | |
| 116082 | F | H | H | H | O | NH | 11 | — | 7 |
| {[3-(4-bromo-1-methylpyrazol-3-yl)phenyl]amino}-N-[2-(trifluoromethoxy)phenyl]carboxamide | | | | | | | | | |
| 116087 | H | H | CF$_3$O | H | O | NH | 11 | — | 200 |
| {[3-(4-bromo-1-methylpyrazol-3-yl)phenyl]amino}-N-(2-nitrophenyl)carboxamide | | | | | | | | | |
| 116089 | H | H | NO$_2$ | H | O | NH | 27 | — | 238 |
| {[3-(4-bromo-1-methylpyrazol-3-yl)phenyl]amino}-N-(4-methoxyphenyl)carboxamide | | | | | | | | | |
| 116091 | MeO | H | H | H | O | NH | 12 | — | 19 |
| {[3-(4-bromo-1-methylpyrazol-3-yl)phenyl]amino}-N-(2-methylphenyl)carboxamide | | | | | | | | | |
| 116092 | H | H | Me | H | O | NH | 32 | — | 131 |
| {[3-(4-bromo-1-methylpyrazol-3-yl)phenyl]amino}-N-[4-(trifluoromethyl)phenyl]carboxamide | | | | | | | | | |
| 116097 | CF$_3$ | H | H | H | O | NH | 11 | — | 65 |
| {[3-(4-bromo-1-methylpyrazol-3-yl)phenyl]amino}-N-(3-chlorophenyl)carboxamide | | | | | | | | | |
| 116105 | H | Cl | H | H | O | NH | 11 | — | 39 |
| {[3-(4-bromo-1-methylpyrazol-3-yl)phenyl]amino}-N-(2-chlorophenyl)carboxamide | | | | | | | | | |
| 116108 | H | H | Cl | H | O | NH | 6 | — | 249 |
| {[3-(4-bromo-1-methylpyrazol-3-yl)phenyl]amino}-N-[4-(methylethyl)phenyl]carboxamide | | | | | | | | | |
| 116110 | isopropyl | H | H | H | O | NH | 7 | — | 338 |

-continued

{[3-(4-bromo-1-methylpyrazol-3-yl)phenyl]amino}-N-(3-methoxyphenyl)carboxamide
| 116111 | H | MeO | H | H | O | NH | 7 | — | 106 |

{[3-(4-bromo-1-methylpyrazol-3-yl)phenyl]amino}-N-(3-methylphenyl)carboxamide
| 116112 | H | Me | H | H | O | NH | 14 | — | 57 |

[{3-(4-bromo-1-methylpyrazol-3-yl)phenyl}amino]-N-methyl-N-[4-(trifluoromethoxy)phenyl]carboxamide
| 116113 | $CF_3O$ | H | H | H | O | $NCH_3$ | — | 193 | 2 |

N-[4-(tert-butyl)phenyl]{[3-(4-bromo-1-methylpyrazol-3-yl)phenyl]amino}carboxamide
| 116119 | t-butyl | H | H | H | O | NH | 17 | — | 476 |

N-[4-(dimethylamino)phenyl]{[3-(4-bromo-1-methylpyrazol-3-yl)phenyl]amino}carboxamide
| 116122 | $NMe_2$ | H | H | H | O | NH | 9 | — | 309 |

N-(3,5-dichloro-4-methylphenyl){[3-(4-bromo-1-methylpyrazol-3-yl)phenyl]amino}carboxamide
| 116138 | Me | Cl | H | Cl | O | NH | 23 | — | 122 |

{[3-(4-bromo-1-methylpyrazol-3-yl)phenyl]amino}-N-[4-(trifluoromethylthio)phenyl]carboxamide
| 116139 | $CF_3S$ | H | H | H | O | NH | 12 | — | 56 |

{[3-(4-bromo-1-methylpyrazol-3-yl)phenyl]amino}-N-(2-fluorophenyl)carboxamide
| 116144 | H | H | F | H | O | NH | 12 | — | 37 |

2-({[3-(4-bromo-1-methylpyrazol-3-yl)phenyl]amino}carbonylamino)benzamide
| 116145 | H | H | $CONH_2$ | H | O | NH | 31 | — | 7473 |

{[3-(4-bromo-1-methylpyrazol-3-yl)phenyl]amino}-N-(4-cyanophenyl)carboxamide
| 116147 | CN | H | H | H | O | NH | 12 | — | 2 |

{[3-(4-bromo-1-methylpyrazol-3-yl)phenyl]amino}-N-(2-cyanophenyl)carboxamide
| 116148 | H | H | CN | H | O | NH | 30 | — | 348 |

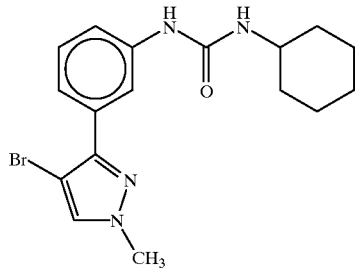

| Compound No. | N-[3-(4-bromo-1-methylpyrazol-3-yl)phenyl][cyclohexylamino]carboxamide | $IP_3$ AP-3 $IC_{50}$ nM | WT $5HT_{2A}$ LSD $IC_{50}$ nM |
|---|---|---|---|
| 116141 | | 114 | 81 |

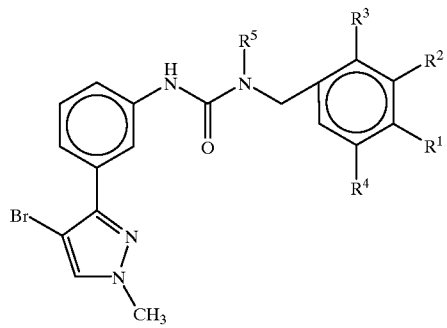

| Compound No. | $R^1$ | $R^2$ | $R^3$ | $R^4$ | $R^5$ | $IP_3$ AP-3 $IC_{50}$ nM | WT $5HTA_{2A}$ LSD $IC_{50}$ nM |
|---|---|---|---|---|---|---|---|
| N-[3-(4-bromo-1-methylpyrazol-3-yl)phenyl][phenylmethylamino]carboxamide | | | | | | | |
| 116143 | H | H | H | H | H | 120 | 47 |

-continued

| Compound No. | R¹ | R² | R³ | R⁴ | R⁵ | IP$_3$ AP-3 IC$_{50}$ nM | WT 5HT$_{2A}$ LSD IC$_{50}$ nM |
|---|---|---|---|---|---|---|---|
| N-[3-(4-bromo-1-methylpyrazol-3-yl)phenyl][{(4-fluorophenyl)methyl}amino]carboxamide | | | | | | | |
| 116182 | F | H | H | H | H | 89 | 132 |
| N-[3-(4-bromo-1-methylpyrazol-3-yl)phenyl][{(3,4-dimethoxyphenyl)methyl}amino]carboxamide | | | | | | | |
| 116183 | OMe | OMe | H | H | H | — | 1010 |
| N-[3-(4-bromo-1-methylpyrazol-3-yl)phenyl][{(3,4,5-trimethoxyphenyl)methyl}amino]carboxamide | | | | | | | |
| 116184 | OMe | OMe | H | OMe | H | — | 2960 |
| N-[3-(4-bromo-1-methylpyrazol-3-yl)phenyl][{(2-methylphenyl)methyl}amino]carboxamide | | | | | | | |
| 116185 | H | H | Me | H | H | — | 769 |
| N-[3-(4-bromo-1-methylpyrazol-3-yl)phenyl][{(4-methoxyphenyl)methyl}amino]carboxamide | | | | | | | |
| 116189 | OMe | H | H | H | H | — | 102 |

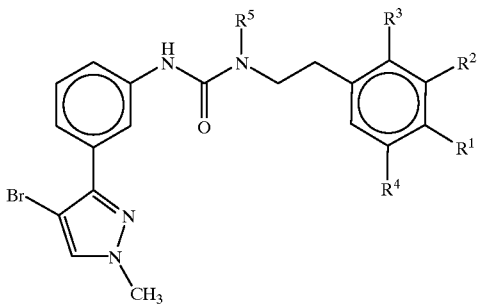

| Compound No. | R¹ | R² | R³ | R⁴ | R⁵ | IP$_3$ AP-3 IC$_{50}$ nM | WT 5HT$_{2A}$ LSD IC$_{50}$ nM |
|---|---|---|---|---|---|---|---|
| N-[3-(4-bromo-1-methylpyrazol-3-yl)phenyl][{2-(4-methoxyphenyl)ethyl}amino]carboxamide | | | | | | | |
| 116194 | OMe | H | H | H | H | 32 | 61 |

A second series of compounds having 5-HT$_{2A}$ receptor activity is represented by a class (II) of compounds of formula (B) wherein Y=O(CH$_2$)$_n$R4:

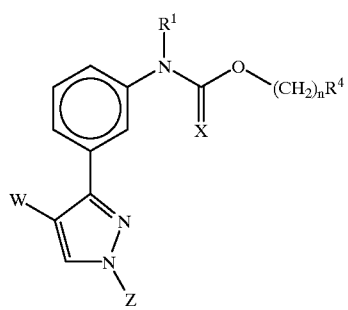

(II)

Wherein:
Preferably R¹ is H.
Preferably W is Br.
Preferably X is O.
Preferably Z is Me.
Preferably when n=0, R⁴ is 4-methoxyphenyl or tertiary butyl.
Preferred compounds are:
116100
N-[3-(4-bromo-1-methylpyrazol-3-yl)phenyl][4-methoxyphenoxy]carboxamide

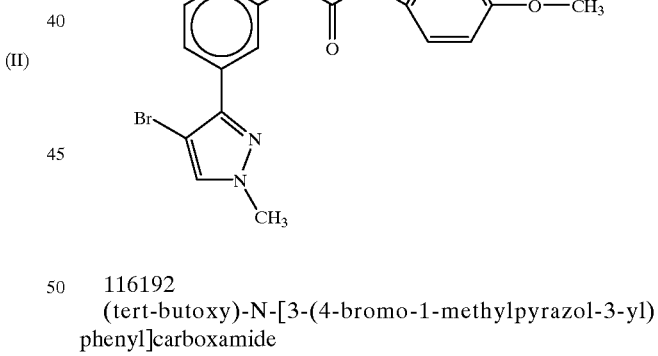

116192
(tert-butoxy)-N-[3-(4-bromo-1-methylpyrazol-3-yl)phenyl]carboxamide

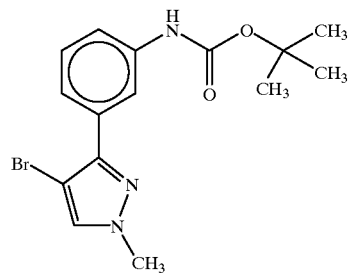

These two compounds demonstrated the following activity:

| Compound No. | Competitive Binding AP-1 ([³H]mesulergine) IC₅₀ Value (μM) | Competitive Binding WT 5HT₂ₐ ([³H]LSD) IC₅₀ Value (μM) | Inositol Phosphate Accumulation AP-3 IC₅₀ Value (μM) |
|---|---|---|---|
| 116100 | 1.8 | <0.001 | 0.0003 |
| 116192 | — | 0.014 | 0.057 |

In addition to the assays discussed above, the specific activity of 116100 at the 5HT₂ₐ receptor was further confirmed by the following.

In Vitro Binding of 5HT₂ₐ Receptor

Animals:

Animals (Sprague-Dawley rats) were sacrificed and brains were rapidly dissected and frozen in isopentane maintained at −42° C. Horizontal sections were prepared on a cryostat and maintained at −20° C.

LSD Displacement Protocol:

Lysergic acid diethylamide (LSD) is a potent 5HT2A receptor and dopamine D2 receptor ligand. An indication of the selectivity of compounds for either or both of these receptors involves displacement of radiolabeled-bound LSD from pre-treated brain sections. For these studies, radiolabeled $I^{125}$-LSD (NEN Life Sciences, Boston, Mass., Catalogue number NEX-199) was utilized; spiperone (RBI, Natick, Mass. Catalogue number s-128), a 5HT2A receptor and dopamine D2 receptor antagonist, was also utilized. Buffer consisted of 50 nanomolar TRIS-HCl, pH 7.4

Brain sections were incubated in (a) Buffer plus 1 nanomolar $I^{125}$-LSD; (b) Buffer plus 1 nanomolar $I^{125}$-LSD and 1 micromolar spiperone; or Buffer plus 1 nanomolar $I^{125}$-LSD and 1 micromolar 116100 for 30 minutes at room temperature. Sections were then washed 2×10 minutes at 4° C. in Buffer, followed by 20 seconds in distilled H₂O. Slides were then air-dried.

After drying, sections were apposed to x-ray film (Kodak Hyperfilm) and exposed for 4 days.

Figure 16A:
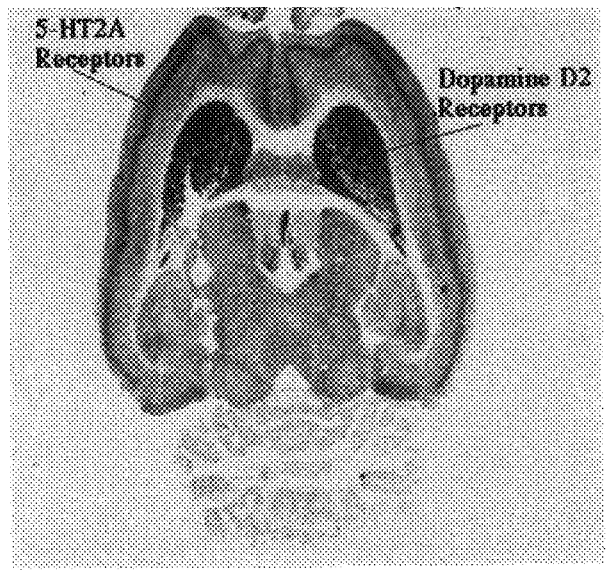
FIGS. 16A–C provides representative auoradiograms showing displacement of I$^{125}$-LSD from brain sections by spiperone and compound 116100.
Figure 16B:
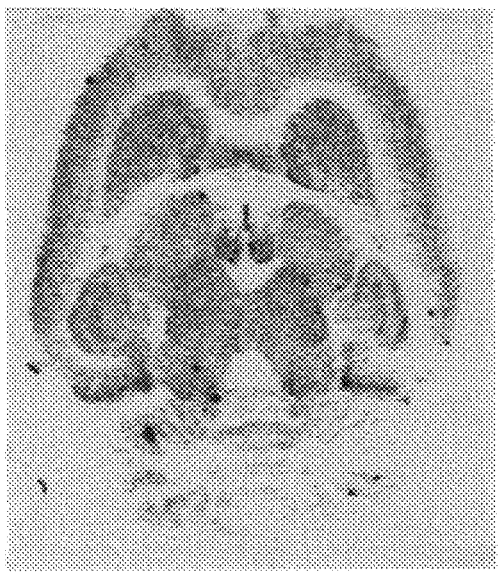
Figure 16C:

Analysis:

FIGS. 16A–C provide representative autoradiographic sections from this study. FIG. 16A evidences darker bands (derived from $I^{125}$-LSD binding) primarily in both the fourth layer of the cerebral cortex (primarily 5HT₂ₐ receptors), and the caudate nucleus (primarily dopamine D2 receptors and some 5HT₂ₐ receptors). As can be seen from FIG. 16B, spiperone, which is a 5HT₂ₐ and dopamine D2 antagonist, displaces the $I^{125}$-LSD from these receptors on both the cortex and the caudate. As can be further seen from FIG. 16C, 116100 appears to selectively displace the $I^{125}$-LSD from the cortex (5HT₂ₐ) and not the caudate (dopamine D2).

A third series of compounds having 5-HT₂ₐ receptor activity is represented by a class (III) of compounds of formula (B) wherein Y=(CH₂)ₘR⁴:

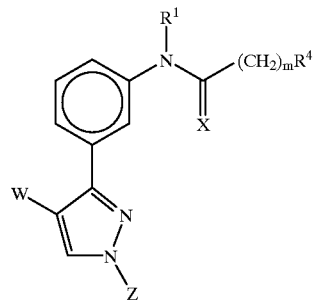

(III)

Wherein:
Preferably W is Br.
Preferably X is O.
Preferably Z is Me.
Preferably R¹ is H.
m=0, R⁴ is preferably 4-trifluoromethoxyphenyl, or thiophene, or 4-chloropheny.
Preferred compounds are:
116101
Preferably when m=0, R¹=H, R⁴=4-trifluoromethoxyphenyl
N-[3-(4-bromo-1-methylpyrazol-3-yl)phenyl][4-trifluoromethoxyphenyl]carboxamide

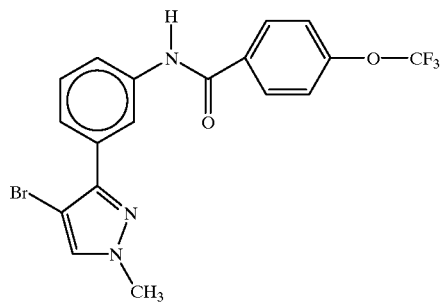

116102
m=0, R¹=H, R⁴=thiophene
N-[3-(4-bromo-1-methylpyrazol-3-yl)phenyl][2-thienyl]carboxamide

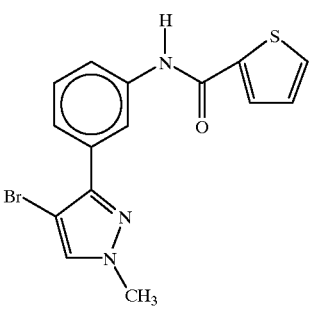

116120
m=0, R¹=H, R⁴=4-chlorophenyl
N-[3-(4-bromo-1-methylpyrazol-3-yl)phenyl][4-chlorophenyl]carboxamide

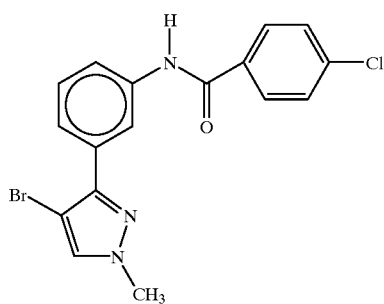

These three compounds demonstrated the following activities:

| Compound Number | Competitive Binding AP-1 ([³H]mesulergine) IC$_{50}$ Value ($\mu$M) | Competitive Binding WT 5HT$_{2A}$ ([³H]LSD) IC$_{50}$ Value ($\mu$M) | Inositol Phosphate Accumulation AP-3 IC$_{50}$ Value ($\mu$M) |
|---|---|---|---|
| 116101 | 6.1 | .46 | 0.0213 |
| 116102 | 2.8 | .17 | 0.080 |
| 116120 | 1.2 | .21 | 0.0315 |

In Vivo Analysis of Compound 116102

In addition to the in vitro assays shown in the above table, the in vivo response of animals to the 116102 compound is demonstrated by the following.

A 5HT$_{2A}$ receptor antagonist or inverse agonist is expected to decrease amphetamine-stimulated locomotion without affecting baseline locomotion. See, for example, Soresnon, et al, 266(2) J. Pharmacol. Exp. Ther. 684 (1993). Based upon the foregoing information, Compound 116102 is a potent inverse agonist at the human 5HT2A receptor. For the following study, the following parameters and protocol were utilized:

Animals, Vehicle

Adult male Sprague-Dawley rats were utilized for these studies. Animals were housed in groups of 2–3 in hanging plastic cages with food and water available at all times. Animals were weighed and handled for at least one day prior to surgery and throughout the studies. For these studies, Vehicle consisted of 90% ethanol (100%) and 10% water.

Amphetamine-stimulated locomotor activity: Assessment and Apparatus

A San Diego Instruments Flex Field apparatus was used to quantify baseline and amphetamine-stimulated locomotor activity. This apparatus consists of four 16"×16" clear plastic open fields. Photocell arrays (16 in each dimension) interfaced with a personal computer to automatically quantify activity. Several measures of activity can be assessed with the apparatus, including total photocell beam breaks. Animals (vehicle control and Compound treated) were injected s.c. 30 minutes prior to initiation of analysis. Following this 30 minute period, animals were placed individually into an open field and baseline activity was assessed for 30 minutes (habituation phase). Following baseline, animals were removed, injected with d-amphetamine sulfate (1.0 mg/kg) and immediately returned to the open field for 150 minutes, in order to follow the time course (10 minute intervals) of amphetamine-stimulated locomotor activity.

Dosing

| Vehicle Control | Compound 116102 | Dose (mg/kg) |
|---|---|---|
| 6 animals | 6 animals | 0.1 |
|  | 6 animals | 1.0 |
|  | 6 animals | 5.0 |
|  | 6 animals | 10.0 |

Analysis

Figure 17A:
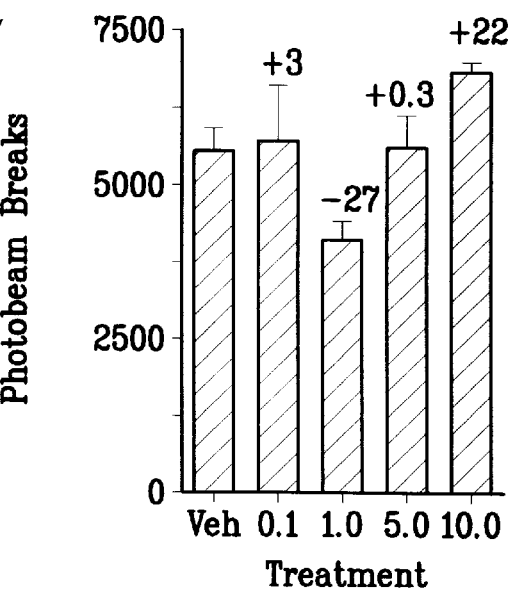
FIG. 17 shows in vivo response of animals to 116102 exposure.
Figure 17B:
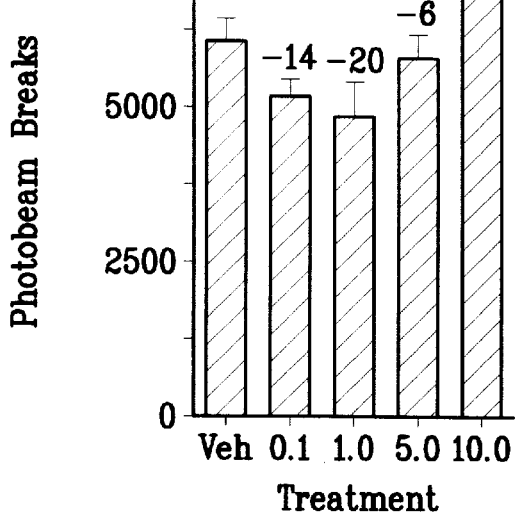
Figure 17C:
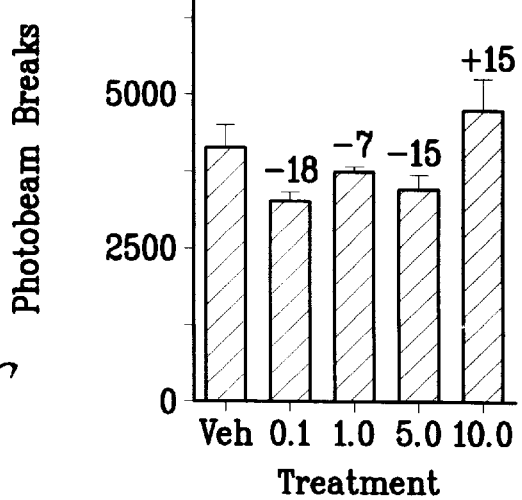

Results, based upon the number of recorded photobeam breaks (mean +/− sem), are presented in FIG. 17A–C. As supported by FIGS. 17A,B and C, a general "inverted U" shaped pattern was observed (see, generally, Sahgal, A. "Practical behavioural neuroscience: problems, pitfalls and suggestions" pp 1–8, 5 in *Behavioral Neuroscience: A Practical Approach*, Volume 1 A. Sahgal (Ed.) 1993, IRL Press, New York). As FIG. 17 also indicates, with exception of the highest dose (10 mg/kg), in vivo, the tested doses of Compound 116102 evidenced a decrease in the amphetamine-stimulated locomotion, consistent with a 5HT2A receptor antagonist or inverse agonist.

Additional compounds of formula (B) wherein Y=(CH$_2$)$_m$ R$^4$ are set forth below.

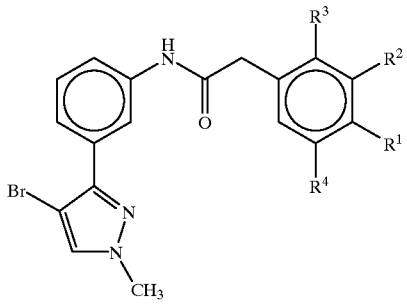

| Compound No. | R$^1$ | R$^2$ | R$^3$ | R$^4$ | IP$_3$ IC$_{50}$ nM | LSD IC$_{50}$ nM |
|---|---|---|---|---|---|---|
| N-[3-(4-bromo-1-methylpyrazol-3-yl)phenyl]-2-[4-(trifluoromethoxy)phenyl]acetamide | | | | | | |
| 116137 | OCF$_3$ | H | H | H | — | 106 |
| N-[3-(4-bromo-1-methylpyrazol-3-yl)phenyl]-2-(3-fluorophenyl)acetamide | | | | | | |
| 116174 | H | F | H | H | 153 | 318 |
| N-[3-(4-bromo-1-methylpyrazol-3-yl)phenyl]-2-(3-methoxyphenyl)acetamide | | | | | | |
| 116175 | H | OMe | H | H | 108 | 625 |
| N-[3-(4-bromo-1-methylpyrazol-3-yl)phenyl]-2-(2-fluorophenyl)acetamide | | | | | | |
| 116176 | H | H | F | H | 129 | 662 |
| N-[3-(4-bromo-1-methylpyrazol-3-yl)phenyl]-2-(4-nitrophenyl)acetamide | | | | | | |
| 116177 | NO$_2$ | H | H | H | 61 | 108 |
| N-[3-(4-bromo-1-methylpyrazol-3-yl)phenyl]-2-(2-methoxyphenyl)acetamide | | | | | | |
| 116178 | H | H | OMe | H | 165 | 2300 | compound names not provided

Based upon the discovery of the specific inverse agonist activity of the above identified compounds at the 5HT$_{2A}$ receptor, a novel class of compounds has been identified which exhibits said activity. Accordingly, in the second aspect of the invention, there is provided a novel compound of formula (C):

(C)

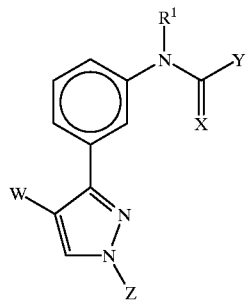

Wherein:
W is Me, or Et, or halogen;
X is either Oxygen or Sulfur;
Y is $NR^2R^3$, or $(CH_2)_m R^4$, or $O(CH_2)_n R^4$;
Z is lower alkyl $(C_{1-6})$;
m=0–4;
n=0–4;
$R^1$ is H or lower alkyl $(C_{1-4})$;
$R^2$ is H or lower alkyl$(C_{1-4})$;
$R^3$ is a $C_{1-6}$ alkyl, or $C_{2-6}$ alkenyl, or cycloalkyl, or $(CH_2)_k$aryl group (k=1–4), preferably k=1, and each said group may be optionally substituted by up to four substituents in any position independently selected from $CF_3$, $CCl_3$, Me, $NO_2$, OH, OMe, OEt, $CONR^5R^6$, $NR^5R^6$, $OCF_3$, SMe, $COOR^7$, $SO_2NR^5R^6$, $SO_3R^7$, COMe, COEt, CO-lower alkyl, $SCF_3$CN, $C_{2-6}$ alkenyl, H, halogens, $C_{14}$ alkoxy, $C_{3-6}$ cycloalkyl, $C_{1-6}$ alkyl, aryl, and aryloxy wherein each of the $C_{3-6}$ cycloalkyl, $C_{1-6}$ alkyl, aryl, or aryloxy groups may be further optionally substituted by up to four substituents in any position independently selected from $CF_3$, $CCl_3$, Me, $NO_2$, OH, OMe, OEt, $CONR^5R^6$, $NR^5R^6$, $NHCOCH_3$, OCF3, SMe, $COOR^7$, $SO_3R^7$, $SO_2NR^5R^6$, COMe, COEt, CO-lower alkyl, $SCF_3$, CN, $C_{2-6}$ alkenyl, H, halogens, $C_{1-4}$ alkoxy, $C_{3-6}$ cycloalkyl, $C_{1-6}$ alkyl, and aryl;

$R^4$ is a $C_{1-6}$ alkyl, or $C_{2-6}$ alkenyl, or cycloalkyl, or aryl group and each said group may be optionally substituted by up to four substituents in any position independently selected from $CF_3$, $CCl_3$, Me, $NO_2$, OH, OMe, OEt, $CONR^5R^6$, $NR^5R^6$, $OCF_3$, SMe, $COOR^7$, $SO_2NR^5R^6$, $SO_3R^7$, COMe, COEt, CO-lower alkyl, $SCF_3$CN, $C_{2-6}$ alkenyl, H, halogens, $C_{1-4}$ alkoxy, $C_{3-6}$ cycloalkyl, $C_{1-6}$ alkyl, aryl, and aryloxy wherein each of the $C_{3-6}$ cycloalkyl, $C_{1-6}$ alkyl, aryl, or aryloxy groups may be further optionally substituted by up to four substituents in any position independently selected from $CF_3$, $CCl_3$, Me, $NO_2$, OH, OMe, OEt, $CONR^5R^6$, $NR^5R^6$, $NHCOCH_3$, OCF3, SMe, $COOR^7$, $SO_3R^7$, $SO_2NR^5R^6$, COMe, COEt, CO-lower alkyl, $SCF_3$, CN, $C_{2-6}$ alkenyl, H, halogens, $C_{1-4}$ alkoxy, $C_{3-6}$ cycloalkyl, $C_{1-6}$ alkyl, and aryl;

$R^5$ and $R^6$ are independently a H, or $C_{1-6}$ alkyl, or $C_{2-6}$ alkenyl, or cycloalkyl, or aryl, or $CH_2$ aryl group and each said group may be optionally substituted by up to four substituents in any position independently selected from $CF_3$, $CCl_3$, Me, $NO_2$, OH, OMe, OEt, $CONR^7R^8$, $NR^7R^8$, $NHCOCH_3$, $OCF_3$, SMe, $COOR^9$, $SO_3R^7$, $SO_2NR^7R^8$, COMe, COEt, CO-lower alkyl, $SCF_3$, CN, $C_{2-6}$ alkenyl, H, halogens, $C_{1-4}$ alkoxy, $C_{3-6}$ cycloalkyl, $C_{1-6}$ alkyl, and aryl wherein each of the $C_{3-6}$ cycloalkyl, $C_{1-6}$ alkyl, or aryl groups may be further optionally substituted by up to four substituents in any position independently selected from $CF_3$, $CCl_3$, Me, $NO_2$, OH, OMe, OEt, $CONR^8R^9$, $NR^8R^9$, $NHCOCH_3$, $OCF_3$, SMe, $COOR^7$, $SO_2NR^8R^9$, $SO_3R^7$, COMe, COEt, CO-lower alkyl, $SCF_3$, CN, $C_{2-6}$ alkenyl, H, halogens, $C_{1-4}$ alkoxy, $C_{3-6}$ cycloalkyl, $C_{1-6}$ alkyl, and aryl, or $R^5$ and $R^6$ may form part of a 5, 6 or 7 membered cyclic structure which may be either saturated or unsaturated and that may contain up to four heteroatoms selected from O, N or S and said cyclic structure may be optionally substituted by up to four substituents in any position independently selected from $CF_3$, $CCl_3$, Me, $NO_2$, OH, OMe, OEt, $OCF_3$, SMe, $COOR^7$, $SO_2NR^8R^9$, $SO_3R^7$, $NHCOCH_3$, COEt, COMe, or halogen;

$R^7$ may be independently selected from H or $C_{1-6}$ alkyl;

$R^8$ and $R^9$ are independently a H, or $C_{1-6}$ alkyl, or $C_{2-6}$ alkenyl, or cycloalkyl, or aryl, or $CH_2$aryl group and each said group may be optionally substituted by up to four substituents in any position independently selected from halogen, $CF_3$, OCF3, OEt, $CCl_3$, Me, $NO_2$, OH, OMe, SMe, COMe, CN, $COOR^7$, $SO_3R^7$, COEt, $NHCOCH_3$, or aryl;

an aryl moiety can be a 5 or 6 membered aromatic heterocyclic ring (containing up to 4 hetero atoms independently selected from N, O, or S) or a 6 membered aromatic non-heterocyclic ring or a polycycle;

$C_{1-6}$ alkyl moieties can be straight chain or branched;

optionally substituted $C_{1-6}$ alkyl moieties can be straight chain or branched;

$C_{2-4}$ alkenyl moieties can be straight chain or branched; and optionally substituted $C_{2-6}$ alkenyl moieties can be straight chain or branched;

with the proviso that said compound is not:
N-[3-(4-bromo-1-methylpyrazol-3-yl)phenyl][methylamino]carboxamide, or
N-[3-(4-bromo-1-methylpyrazol-3-yl)phenyl][{(4-trifluoromethoxy)phenyl}amino]carboxamide, or
N-[3(4-bromo-1-methylpyrazol-3-yl)phenyl][2-chlorophenyl]carboxamide, or
N-[3-(4-bromo-1-methylpyrazol-3-yl)phenyl][2-chloro-3-pyridyl]carboxamide, or
N-[3-(4-bromo-1-methylpyrazol-3-yl)phenyl][trichloromethyl]carboxamide.

Examples of suitable $C_{1-6}$ alkyl groups include but art not limited to methyl, ethyl, n-propyl, i-propyl, n-butyl, and t-butyl.

Halogens are typically F, Cl, Br, and I.

Examples of 5 or 6 membered ring moieties include, but are not restricted to, phenyl, furanyl, thienyl, imidazolyl, pyridyl, pyrrolyl, oxazolyl, isoxazolyl, triazolyl, pyrazolyl, tetrazolyl, thiazolyl and isothiazolyl. Examples of polycycle moieties include, but are not restricted to, naphthyl, benzothiazolyl, benzofuranyl, benzimidazolyl, quinolyl, isoquinolyl, indolyl, quinoxalinyl, quinazolinyl and benzothienyl.

Synthetic Approaches

The compounds disclosed in this invention may be readily prepared according to a variety of synthetic manipulations, all of which would be familiar to one skilled in the art. In the general syntheses set forth below, the labeled substituents have the same identifications as set out in the definitions of the compounds above.

Compounds of general formula (I) can be obtained via a variety of synthetic routes all of which would be familiar to one skilled in the art. The reaction of isocyanates with amines is a commonly practised method for the formation of ureas (see Org. Syn. Coll. Vol. V, (I 973), 555). Amine (IV), 3-(4-bromo-1-methylpyrazole-3-yl)phenylamine, commercially available from Maybridge Chermical Company, Catalog No. KM01978, CAS No. 175201-77-1] reacts readily with isocyanates (V) in inert solvents such as halocarbons to yield the desired ureas of general formula (I) wherein $R^1=R^2=H$:

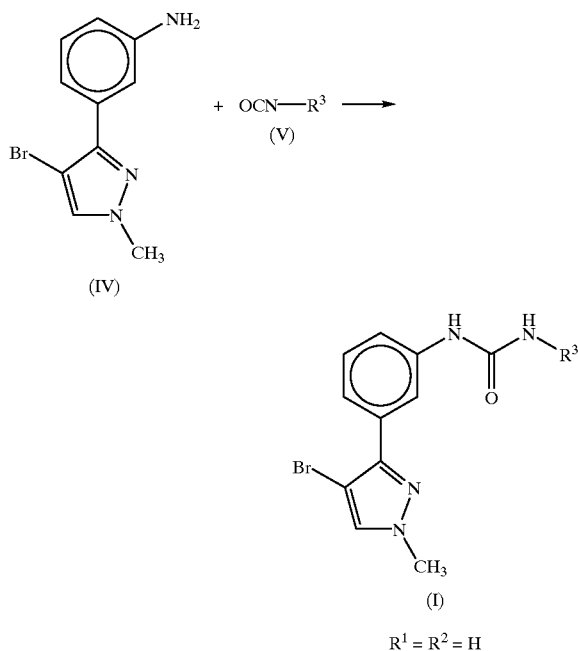

Alternatively the amine (IV) can be converted to the corresponding isocyanate (VI) by the action of phosgene or a suitable phosgene equivalent, e.g. triphosgene, in an inert solvent such as a halocarbon in the presence of an organic base such as triethylamine or ethyldiisopropylamine. Isocyanate (VI) reacts with amines of general formula (VII), in an analogous fashion to that described above for the reaction of (IV) with (V), yielding the desired ureas of general formula (I) wherein $R^1=H$:

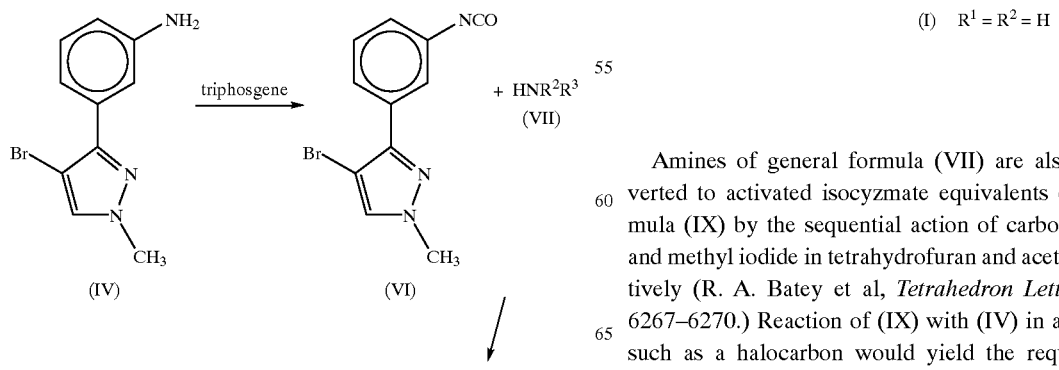

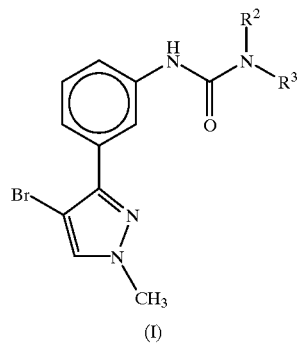

Alternatively wherein the isocyanate of general formula (V) is not commercially available it can be prepared from the corresponding amine of general formula (VHI) in an analogous procedure to that described above for the preparation of (VI). Reaction of these isocyanates with (IV) mould again yield the requisite ureas of general formula (I) wherein $R^1=R^2=H$:

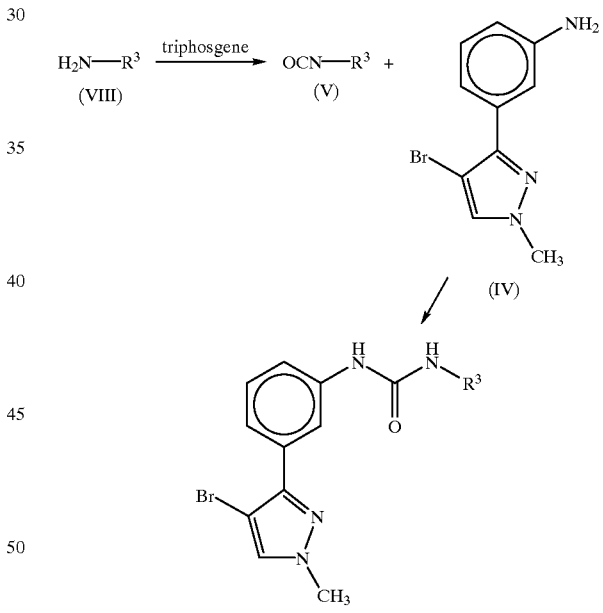

Amines of general formula (VII) are also readily converted to activated isocyzmate equivalents of general formula (IX) by the sequential action of carbonyldiimidazole and methyl iodide in tetrahydrofuran and acetonitrile respectively (R. A. Batey et al, *Tetrahedron Lett.*, (19)98), 39, 6267–6270.) Reaction of (IX) with (IV) in an inert solvent such as a halocarbon would yield the requisite ureas of general formula (I) wherein $R^1=H$:

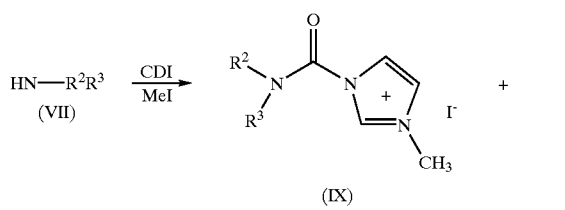

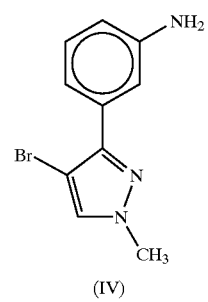

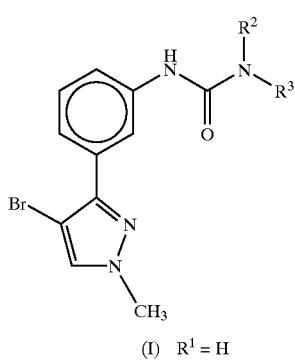

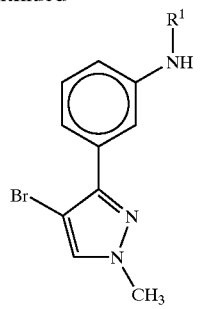

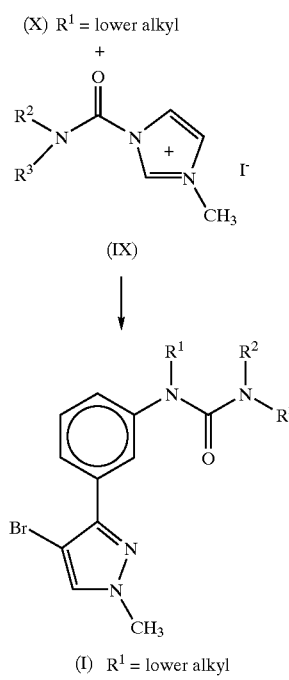

Amine (IV) may be monomethylated according to the procedure of J. Barluenga et al, *J. Chem. Soc., Chem. Commun.*, (1984), 20, 1334–1335, or alkylated according to the procedure of P. Marchini et al, *J. Org. Chem.*, (1975), 40(23) 3453–3456, to yield compounds of general formula (X) wherein $R^1$=lower alkyl. These materials may be reacted as above with reagents of general formula (V) and (IX) as depicted below:

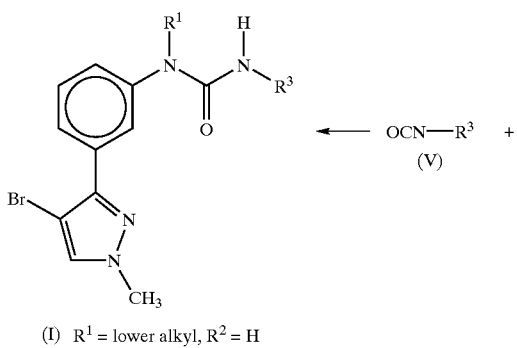

Compounds of general formula (II) can similarly be obtained via a variety of synthetic manipulations, all of which would be familiar to one skilled in the art. The reaction of amine (IV)) with chloroformates (see Org. Syn. Coll. Vol. IV, (1963), 780) of general formula (XI) in an inert solvent such as ether or halocarbon in the presence of a tertiary base such as triethylamine or ethyldiisopropylamine readily yields the requisite carbamates of general formula (II) wherein $R^1$=H. Analogously amines of general formula (X) react similarly with chloroformates (XI) to yield the requisite carbamates of general formula (II) wherein $R^1$=lower alkyl:

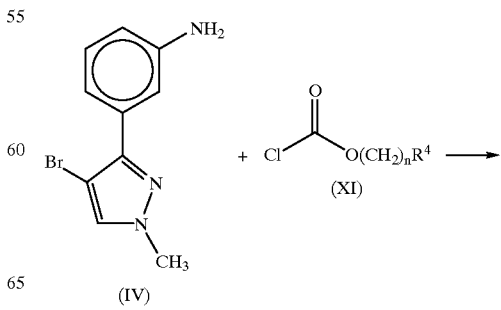

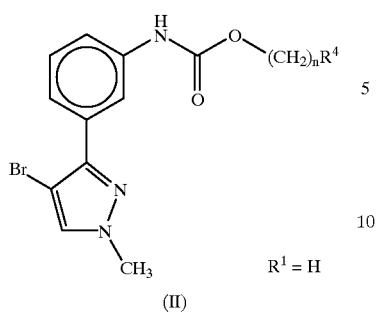
(II) R¹ = H

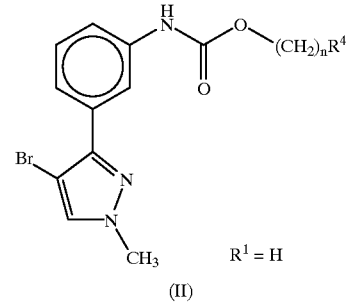
(II) R¹ = H

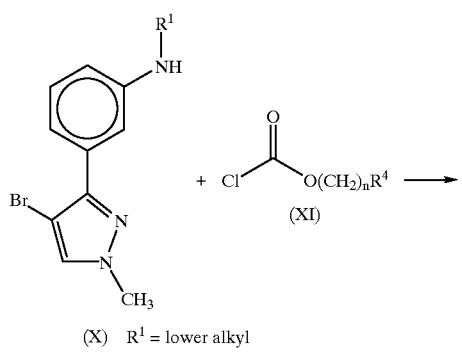
(X) R¹ = lower alkyl

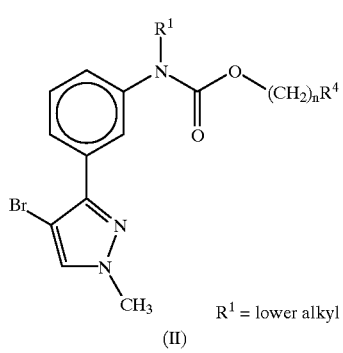
(II) R¹ = lower alkyl

An alternative route employs the ready reaction of an alcohol with an isocyanate. Thus isocyanate (VI) described previously reacts readily with alcohols (XII) in an aprotic solvent such as ether or chlorocarbon to yield the desired carbamates of general formula (II) wherein R¹=H:

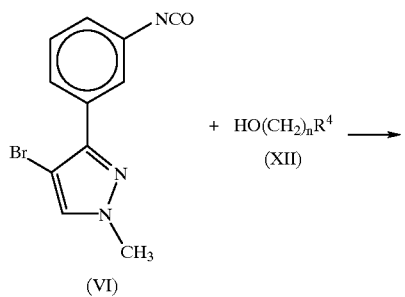
(VI)

Chloroformates of general formula (XI) not commercially available may be readily prepared from the corresponding alcohol (XII) in an inert solvent such as toluene, chlorocarbon or ether by the action of excess phosgene (see Org. Syn. Coll. Vol. III, (1955), 167):

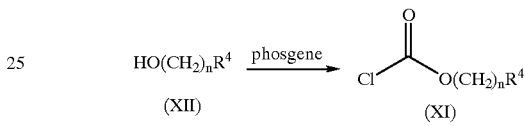

Compounds of general formula (III) can be obtained via a variety of synthetic manipulations, all of which would be familiar to one skilled in the art. The reaction of amine (IV) with acid chlorides (see Org. Syn. Coll. Vol. V, (1973), 336) of general formula (XIII) to yield the desired amides (III) wherein R¹=H is readily achieved in an inert solvent such as chloroform or dichloromethane in the presence of an organic base such as triethylamine or ethyldiisopropylamine. In an identical fashion amines of general formula (X) would react with acid chlorides (XIII) to yield the desired amides (III) wherein R¹=lower alkyl:

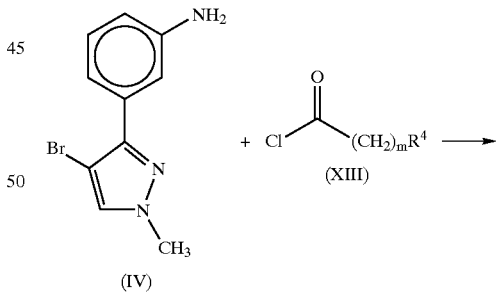
(IV)            (XIII)

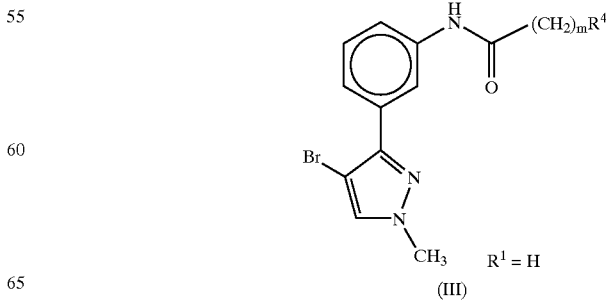
(III) R¹ = H

-continued

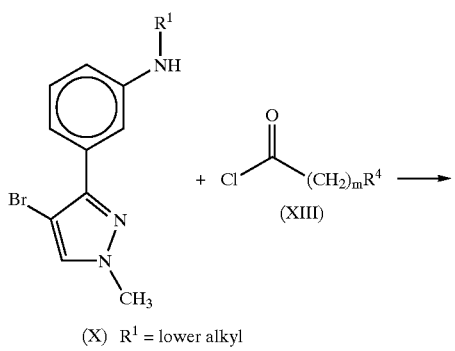

(X)  R¹ = lower alkyl

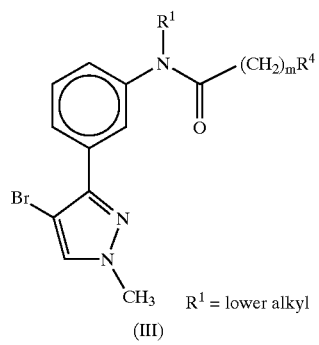

Alternatively the corresponding acids of general formula (XIV) may be coupled with dicyclohexylcarbodiimide (DCC)/hydroxybenzotriazole (HOBT) (see W. Konig et al, *Chem. Ber.*, (1970), 103, 788) or hydroxybenzotriazole (HOBT)/2-(1H-benzotriazole-1-yl)-1,1,3,3-tetramethyluronium hexafluorophosphate (HBTU) (see M. Bernatowicz et al., *Tetrahedron Lett.*, (1989), 30, 4645) as condensing agents in dimethylformamide or chloroform to amines (IV) and (X) respectively yielding products identical to those described in the previous scheme:

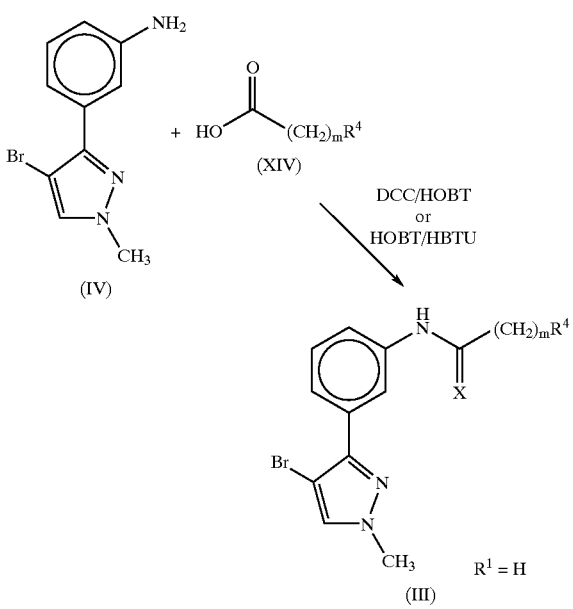

-continued

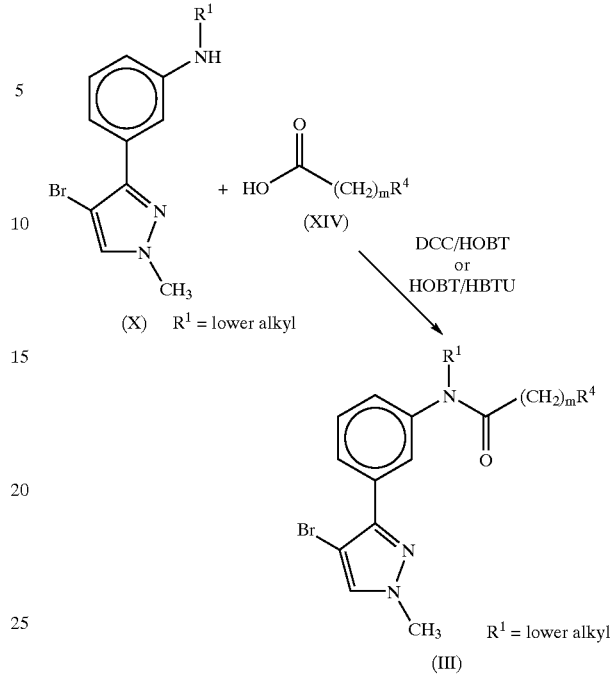

The acids of general formula (XIV) are readily converted to the corresponding acid chlorides (XIII) by the action of thionyl chloride or oxalyl chloride in the presence of catalytic dimethylformamide:

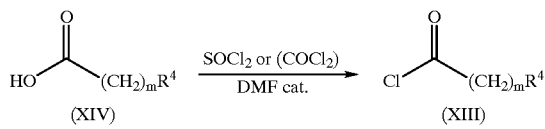

A third aspect of the present invention provides a compound of formula (A) or a solvate or physiologically functional derivative thereof for use as a therapeutic agent, specifically as a modifier of the activity of the serotonin 5-HT$_{2A}$ receptor. Modifiers of the activity of the serotonin 5-HT$_{2A}$ receptor are believed to be of potential use for the treatment or prophylaxis of CNS, gastrointestinal, cardiovascular, and inflammatory disorders. Compounds of the formula (A) may be administered by oral, sublingual, parenteral, rectal, or topical administration. In addition to the neutral forms of compounds of formula (A) by appropriate addition of an ionizable substituent, which does not alter the receptor specificity of the compound, physiologically acceptable salts of the compounds may also be formed and used as therapeutic agents. Different amounts of the compounds of formula (A) will be required to achieve the desired biological effect. The amount will depend on factors such as the specific compound, the use for which it is intended, the means of administration, and the condition of the treated individual. A typical dose may be expected to fall in the range of 0.001 to 200 mg per kilogram of body weight of the treated individual. Unit does may contain from 1 to 200 mg of the compounds of formula (A) and may be administered one or more times a day, individually or in multiples. In the case of the salt or solvate of a compound of formulas (A), the dose is based on the cation (for salts) or the unsolvated compound.

A fourth aspect of the present invention provides pharmaceutical compositions comprising at least one compound of formula (A) and/or a pharmacologically acceptable salt or solvate thereof as an active ingredient combined with at least one pharmaceutical carrier or excipient. Such pharmaceutical compositions may be used in the treatment of clinical conditions for which a modifier of the activity of the serotonin 5-$HT_{2A}$ receptor is indicated. At least one compound of formula (A) may be combined with the carrier in either solid or liquid form in a unit dose formulation. The pharmaceutical carrier must be compatible with the other ingredients in the composition and must be tolerated by the individual recipient. Other physiologically active ingredients may be incorporated into the pharmaceutical composition of the invention if desired, and if such ingredients are compatible with the other ingredients in the composition. Formulations may be prepared by any suitable method, typically by uniformly mixing the active compound(s) with liquids or finely divided solid carriers, or both, in the required proportions, and then, if necessary, forming the resulting mixture into a desired shape.

Conventional excipients, such as binding agents, fillers, acceptable wetting agents, tabletting lubricants, and disintegrants may be used in tablets and capsules for oral administration. Liquid preparations for oral administration may be in the form of solutions, emulsions, aqueous or oily suspensions, and syrups. Alternatively, the oral preparations may be in the form of dry powder which can be reconstituted with water or another suitable liquid vehicle before use. Additional additives such as suspending or emulsifying agents, non-aqueous vehicles (including edible oils), preservatives, and flavorings and colorants may be added to the liquid preparations. Parenteral dosage forms may be prepared by dissolving the compound of the invention in a suitable liquid vehicle and filter sterilizing the solution before filling and sealing an appropriate vial or ampoule. These are just a few examples of the many appropriate methods well known in the art for preparing dosage forms.

The fifth aspect of the present invention provides for the use of a compound of formula (A) in the preparation of a medicament for the treatment of a medical condition for which a modifier of the activity of the serotonin 5-$HT_{2A}$ receptor is indicated.

A sixth aspect of the present invention provides for a method of treatment of a clinical condition of a mammal, such as a human, for which a modifier of the activity of the serotonin 5-$HT_{2A}$ receptor is indicated, which comprises the administration to the mammal of a therapeutically effective amount of a compound of formula (A) or a physiologically acceptable salt, solvate, or physiologically functional derivative thereof.

Experimental Data

Mass spectra were recorded on a Micromass Platform LC with Gilson HPLC. Infrared spectra were recorded on a Nicolet Avatar 360 FT-IR. Melting points were recorded on a Electrothermal IA9200 apparatus and are uncorrected. Proton nuclear magnetic resonance spectra were recorded on a Bruker 300 MHz machine. Chemical shifts are given with respect to tetramethylsilane. In the text the following abbreviations are used; s (singlet), d (doublet), t (triplet), m (multiplet) or combinations thereof. Chemical shifts are quoted in parts per million (ppm) and with coupling constants in Hertz.

Thin layer chromatography was carried out using aluminium backed silica plates (250 µL; $GF_{254}$). HPLC was recorded either on a HP Chemstation 1100 HPLC using a Hichrom 3.5 C18 reverse phase column (50 mm×2.1 mm i.d.). Linear gradient elution over 5 minutes—95% water (+0.1% TFA)/5% acetonitrile (+0.05% TFA) down to 5% water/95% acetonitrile. Flow rate 0.8 mL/min [Method A]; or on a Hichrom 3.5 C18 reverse phase column (100 mm×3.2 mm i.d.). Linear gradient elution over 11 minutes— 95% water (+0.1% TFA)/5% acetonitrile (+0.05% TFA) down to 5% water/95% acetonitrile. Flow rate 1 mL/min [Method B]. Samples were routinely monitored at 254 nM unless otherwise stated.

All reagents were purchased from commercial sources.

Experiment 1

Preparation and Analysis of 103487

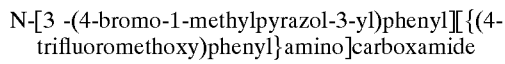
N-[3 -(4-bromo-1-methylpyrazol-3-yl)phenyl][{(4-trifluoromethoxy)phenyl}amino]carboxamide This compound is commercially available from Maybridge Chemical Company, Catalog No. KM04515.

Experiment 2

Preparation and Analysis of 116100

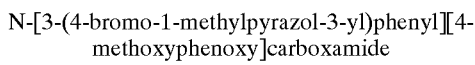
N-[3-(4-bromo-1-methylpyrazol-3-yl)phenyl][4-methoxyphenoxy]carboxamide To 4-methoxyphenylchloroformate (19 mg, 0.10 mmol) in $CH_2Cl_2$ (0.5 mL) was added dropwise a solution of 3-(3-aminophenyl)-4-bromo-1-methylpyrazole (25 mg, 0.10 mmol) and triethylamine (14 µL, 0.10 mmol) in $CH_2Cl_2$ (0.5 mL). The mixture was stirred for 16 h and concentrated. Chromatography on flash silica (40% EtOAc/hexane) gave the title compound as a colourless solid (24 mg, 526), m.p. 140.3–141.8° C. (EtOAc/hexane).

IR: $\lambda_{max}$=1748, 1592, 1504, 1412, 1190, 835, 764, 676 $cm^{-1}$. MS (ES+): m/z (%)=404 (M+H $^{81}$Br, 100), 402 (M+H $^{79}$Br, 90).

$^1$H-NMR ($CD_3OD$): δ=3.80 (3H, s, $CH_3$), 3.81 (3H, s, $CH_3$), 6.91–6.98 (2H, m, ArH), 7.07–7.18 (3H, m, ArH), 7.42–7.53 (4H, m, ArH). HPLC: retention time 3.28 mins [Method A]. Tlc : Rf 0.4 (EtOAc/hexane).

Experiment 3

Preparation and Analysis of 116101

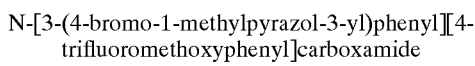
N-[3-(4-bromo-1-methylpyrazol-3-yl)phenyl][4-trifluoromethoxyphenyl]carboxamide To 4-(trifluoromethoxy)benzoyl chloride (19 µL, 0.12 mmol) in $CH_2Cl_2$ (1 mL) was added dropwise a solution of 3-(3-aminophenyl)-4-bromo-1-methylpyrazole (30 mg, 0.12 mmol) and triethylamine (17 µL, 0.12 mmol) in $CH_2Cl_2$ (0.5 mL). The reaction mixture was stirred for 16 h and concentrated. Chromatography on flash silica (50% EtOAc/hexane) gave the title compound as a colourless solid (40 mg, 76%), m.p. 138.6–139.6° C. (EtOAc/hexane).

MS (ES+): m/z (%)=442 (M+H $^{81}$Br, 93), 440 (M+H $^{79}$Br, 100).

$^1$H-NMR (DMSO $d_6$): δ=3.79 (3H, s, $CH_3$), 7.27 (1H, m, ArH), 7.45–7.60 (3H, m, ArH), 7.65 (1H, s, ArH), 7.87 (2H, m, ArH), 8.09 (2H, m, ArH), 10.51 (1H, s, NH).

HPLC: retention time 3.60 min [Method A]. TLC: Rf 0.40 (50% EtOAc/hexane).

Experiment 4

Preparation and Analysis of 1116102

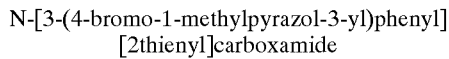
N-[3-(4-bromo-1-methylpyrazol-3-yl)phenyl] [2thienyl]carboxamide

To thiophene-2-carbonyl chloride (11 µL, 0.09 mmol) in $CH_2Cl_2$ (1 mL) was added dropwise a solution of 3-(3- amninophenyl)-4-bromo-1-methylpyrazole (25 mg, 0.09 mmol) and triethylamine (14 μL, 0.09 mmol) in CH$_2$Cl$_2$ (0.5 mL). The reaction mixture was stirred for 16 h and concentrated. Chromatography on flash silica (50% EtOAc/hexane) gave the title compound as a colourless solid (24 mg, 68%), m.p. 127.8–128.6° C. (EtOAc/hexane).

MS (ES+): m/z (%)=364 (M+H $^{81}$Br, 96), 362 (M+H $^{79}$Br, 100).

$^1$H-NMR (CD$_3$OD): δ=3.81 (3H, s, CH$_3$), 7.19 (2H, m, ArH), 7.48–7.58 (2H, m, ArH), 7.68–7.83 (3H, m, ArH), 7.93 (1H, dd, J=1.0, 3.8, ArH).

HPLC: retention time 3.12 min [Method A]. TLC: Rf 0.30 (30% EtOAc/hexane).

Experiment 5

Preparation and Analysis of 116115

N-[3-(4-bromo-1-methylpyrazol-3-yl)phenyl][{(4-trifluoromethoxyphenyl)methyl}amino]carboxamide To a stirred solution of triphosgene (12 mg, 0.04 mmol) in CH$_2$Cl$_2$ (0.5 mL) was added dropwise a solution of 3-(3-aminophenyl)4-bromo-1-methylpyrazole (30 mg, 0.12 mmol) and triethylamine (33 μL, 0.24 mmol) in CH$_2$Cl$_2$ (0.5 mL). After 1 h, 4-(trifluoromethoxy)benzylamine (23 mg, 0.12 mmol) was added. The reaction mixture was stirred for 16 h and concentrated. Chromatography on flash silica (75% EtOAc/hexane) gave the title compound as a colourless solid (38 mg, 68%), m.p. 144.6–145.8° C. (EtOAc/hexane).

IR: λ$_{max}$=1626, 1558, 1278, 1160, 969, 871, 789, 703 cm$^{-1}$. MS (ES+): m/z (%)=471 (M+H $^{81}$Br, 91), 469 (M+H $^{79}$Br, 100).

$^1$H-NMR (CD$_3$OD): δ=3.81 (3H, s, CH$_3$), 4.42 (2H, s, CH$_2$), 7.06 (1H, d, J=7.1, ArH), 7.24 (2H, d, J=8.4, ArH), 7.37–7.52 (6H, m, ArH). HPLC: retention time 3.06 mins [Method A]. Tlc: Rf 0.5 (EtOAc).

Experiment 6

Preparation and Analysis of 116120

N-[3-(4-bromo-1-methylpyrazol-3-yl)phenyl][4-chlorophenyl]carboxamide

To 4-chlorobenzoyl chloride (15 mg, 0.08 mmol) in CH$_2$Cl$_2$ (1 mL) was added dropwise a solution of 3-(3-aminophenyl)-4-bromo-1-methylpyrazole (21 mg, 0.08 mmol) and triethylamine (12 μL, 0.08 mmol) in CH$_2$Cl$_2$ (0.5 mL). The mixture was stirred for 16 h and concentrated. Chromatography on flash silica (50% EtOAc/hexane) gave the title compound as a colourless solid (23 mg, 72%), m.p. 184.4–184.8° C. (EtOAc/hexane).

MS (ES+): m/z (%)=394 (M+H $^{81}$Br $^{37}$Cl, 34), 392 (M+H $^{79}$Br $^{37}$Cl ($^{81}$Br $^{35}$Cl), 100), 390 (M+H $^{79}$Br $^{35}$Cl, 67).

$^1$H-NMR (DMSO d$_6$): δ=3.79 (3H, s, CH$_3$), 7.25 (1H, d, J=7.9, ArH), 7.51–7.65 (3H, m, ArH), 7.69 (1H, s, ArH), 7.90 (2H, m, ArH), 8.00 (2H, m, ArH), 10.51 (1H, s, NH).

HPLC: retention time 3.40 min [Method A]. TLC: Rf 0.35 (50%/ EtOAc/hexane).

Experiment 7

Preparation and Analysis of 116137

N-[3-(4-bromo-1-methylpyrazol-3-yl)phenyl]-2-[4-(trifluoromethoxy)phenyl]acetamide A solution of 3-(3-aminophenyl)-4-bromo-1-methylpyrazole (35 mg, 0.14 mmol) and triethylamine (23 μL, 0.17 mmol) in DMF (0.5 mL) was added in one portion to a stirred solution of 4-trifluoromethoxyphenylacetic acid (31 mg, 0.14 mmol), HBTU (53 mg, 0.14 mmol) and HOBT (19 mg, 0.14 mmol) in DMF (1 mL). The mixture was heated at 70° C. for 24 h and then quenched with aqueous sodium bicarbonate solution. Ethyl acetate was added and the organic phase separated, washed with water (×3), brine, dried (MgSO$_4$) and evaporated. Chromatography on flash silica (50% EtOAc/hexane) gave the title compound as a colourless solid (43 mg, 68%), m.p. 141.2–142.5° C. (EtOAc/hexane).

IR: λ$_{max}$=1684, 1592, 1510, 1253, 1217, 1157, 987, 798, 700 cm$^{-1}$.

MS (ES+) m/z (%)=456 (M+H $^{81}$Br, 100), 454 (M+H $^{79}$Br, 94).

$^1$H-NMR (DMSO d$_6$): δ=3.72 (2H, s, CH$_2$), 3.75 (3H, s, CH$_3$), 7.17 (1H, d, J=7.7, ArH), 7.33 (2H, d, J=8.7, ArH), 7.38–7.51 (3H, m, ArH), 7.62–7.73 (3H, m, ArH), 10.44 (1H, s, NH).

HPLC: retention time 3.52 min [Method A].

Experiment 8

Preparation and Analysis of 116174

N-[3-(4-bromo-1-methylpyrazol-3-yl)phenyl]-2-(3-fluorophenyl)acetamide

A mixture of 3-(3-aminophenyl)-4-bromo-1-methylpyrazole (30 mg, 0.12 mmol), 3-fluorophenylacetic acid (18 mg, 0.12 mmol), 1-hydroxybenzotriazole hydrate (16 mg, 0.12 mmol) and 2-(1H-benzotriazole-1-yl)-1,1,3,3-tetramethyluronium hexafluoro-phosphate (46 mg, 0.12 mmol) were dissolved in chloroform (1.5 ml). N, N-Diisopropylethylamine (0.02 ml, 0.13 mmol) was added and the mixture stirred at room temperature for 16 h. The reaction mixture was then poured into brine and the organic layer washed with further brine, dried over magnesium sulphate and then concentrated in vacuo. The crude product was purified by column chromatography (ethyl acetate-toluene, 1:1), giving the title compound (12 mg, 26%). Rf 0.41 (ethyl acetate-toluene, 1:1).

HPLC (Method B): retention time 7.07 min (100%). δ$_H$ (CDCl$_3$) 3.77 (2H, s), 3.83 (3H, s), 7.02–7.20 (4H, m), 7.54 (1H, s), 7.60–7.63 (1H, m). MS (AP+): m/z (%)=390 (M+H $^{81}$Br, 100), 388 (M +H $^{79}$Br, 100).

Experiment 9

Preparation and Analysis of 116175

N-[3-(4-bromo-1-methylpyrazol-3-yl)phenyl]-2-(3-methoxyphenyl)acetamide

A solution of 3-methoxyphenylacetyl chloride (0.02 ml, 0.12 mmol) in dichloromethane (0.75 ml) was added dropwise at 0° C. to a solution of 3-(3-aminophenyl)-4-bromo-1-methylpyrazole (30 mg, 0.12 mmol) and triethylamine (0.02 ml, 0.13 mmol) in dichloromethane (0.75 ml). The resulting mixture was stirred at room temperature for 16 h and then poured into brine. The organic layer was washed with more brine then dried over magnesium sulphate and concentrated in vacuo. The crude product was purified by column chromatography (ethyl acetate-toluene, 1:1), giving the title compound (9 mg, 19%). Rf 0.30 (ethyl acetate-toluene, 1:1).

HPLC (Method B): retention time 8.62 min (97.09%). δ$_H$ (CDCl$_3$) 3.76 (2H, s), 3.82 (3H, s), 3.85 (3H, s), 6.84–6.90

(3H, m), 7.07–7.44 (5H, m), 7.53 (1H, s), 7.60 (1H, br s). MS (AP+): m/z (%)=402 (M+H $^{81}$Br, 100), 400 (M+H $^{79}$Br, 95).

Experiment 10

Preparation and Analysis of 116176

N-[3-(4-bromo-1-methylpyrazol-3-yl)phenyl]-2-(2-fluorophenyl)acetamide

A mixture of 3-(3-aminophenyl)-4-bromo-1-methylpyrazole (30 mg, 0.12 mmol), 2-fluorophenylacetic acid (18 mg, 0.12 mmol), 1-hydroxybenzotriazole hydrate (16 mg, 0.12 mmol) and 2-(1H-benzotriazole-1-yl)-1,1,3,3-tetramethyluronium hexafluoro-phosphate (46 mg, 0.12 mmol) were dissolved in chloroform (1.5 ml). N, N-Diisopropylethylamine (0.02 ml, 0.13 mmol) was added and the mixture stirred at room temperature for 16 h. The reaction mixture was then poured into brine and the organic layer washed with further brine, dried over magnesium sulphate and then concentrated in vacuo. The crude product was purified by column chromatography (ethyl acetate-toluene, 1:1), giving the title compound (15 mg, 32%). Rf 0.52 (ethyl acetate-toluene, 1:1).

HPLC (Method B): retention time 7.28 min (100%). $\delta_H$ (CDCl$_3$) 3.79 (2H, s), 3.83 (3H, s), 7.11–7.23 (3H, m), 7.30–7.55 (6H, m), 7.61–7.64 (1H, m). MS (AP+): m/z (%)=390 (M+H $^{81}$Br, 100), 388 (M+H $^{79}$Br, 100).

Experiment 11

Preparation and Analysis of 116177

N-[3-(4-bromo-1-methylpyrazol-3-yl)phenyl]-2-(4-nitrophenyl)acetamide

A mixture of 3-(3-aminophenyl)-4-bromo-1-methylpyrazole (30 mg, 0.12 mmol), 4-nitrophenylacetic acid (22 mg, 0.12 mmol), 1-hydroxybenzotriazole hydrate (16 mg, 0.12 mmol) and 2-(1H-benzotriazole-1-yl)-1,1,3,3-tetramethyluronium hexafluorophosphate (46 mg, 0.12 mmol) were dissolved in chloroform (1.5 ml). N, N-Diisopropylethylamine (0.02 ml, 0.13 mmol) was added and the mixture stirred at room temperature for 16 h. The reaction mixture was then poured into brine and the organic layer washed with further brine, dried over magnesium sulphate and then concentrated in vacuo. The crude product was purified by column chromatography (ethyl acetate-toluene, 1:1), giving the title compound (9 mg, 18%). Rf 0.19 (ethyl acetate-toluene, 1:1).

HPLC (Method B): retention time 7.22 min (94.30%). $\delta_H$ (CDCl$_3$) 3.83 (3H, s), 3.87 (2H, s), 7.18–7.23 (1H, m), 7.42–7.65 (7H, m), 8.22–8.30 (2H, m). MS (AP+): m/z (%)=417 (M+H $^{81}$Br, 100), 415 (M+H $^{79}$Br, 100).

Experiment 12

Preparation and Analysis of 116178

N-[3-(4-bromo-1-methylpyrazol-3-yl)phenyl]-2-(2-methoxyphenyl)acetamide

A mixture of 3-(3-aminophenyl)-4-bromo-1-methylpyrazole (30 mg, 0.12 mmol), 2-methoxyphenylacetic acid (20 mg, 0.12 mmol), 1-hydroxybenzotriazole hydrate (16 mg, 0.12 mmol) and 2-(1H-benzotriazole-1-yl)-1,1,3,3-tetramethyluronium hexafluoro-phosphate (46 mg, 0.12 mmol) were dissolved in chloroform (1.5 ml). N, N-Diisopropyl-ethylamine (0.02 ml, 0.13 mmol) was added and the mixture stirred at room temperature for 16 h. The reaction mixture was then poured into brine and the organic layer washed with further brine, dried over magnesium sulphate and then concentrated in vacuo. The crude product was purified by column chromatography (chloroform-methanol, 99:1), giving the title compound (18 mg, 38%) as a colourless solid. Rf 0.65 (chloroform-methanol, 98:2).

HPLC (Method B): retention time 7.16 min (100%). $\delta_H$ (CDCl$_3$) 3.76 (2H, s), 3.83 (3H, s), 3.98 (3H, s), 6.97–7.06 (2H, m), 7.11–7.16 (1H, m), 7.31–7.50 (4H, m), 7.53 (1H, s), 7.57–7.60 (1H, m), 7.91 (1H, br s). MS (AP-): m/z (%) 400 (M-H $^{81}$Br, 90), 398 (M-H $^{79}$Br, 100).

Experiment 13

Preparation and Analysis of 116192

{[3-(4-bromo-1-methylpyrazol-3-yl)phenyl]amino}-N-(1,1-dimethylethoxy)carboxamide To di-tert-butyl dicarbonate (36 mg, 0.17 mmol) in methanol (1 mL) was added dropwise a solution of 3-(3-aminophenyl)-4-bromo-1-methylpyrazole (42 mg, 0.17 mmol) in methanol (1 mL). The mixture was stirred for 16 h and concentrated. Chromatography on flash silica (40% EtOAc/heaxne) gave the title compound as a colourless solid (29 mg, 49%) (EtOAc/hexane).

MS (CI-): m/z (%)=352 (M-H $^{81}$Br, 100), 350 (M-H $^{79}$Br, 96).

$^1$H-NMR (DMSO d$_6$): $\delta$32 1.46 (9H, s, 3xCH$_3$), 3.73 (3H, s, CH$_3$), 7.07 (1H, m, ArH), 7.42 (1H, t, J=7.7, ArH), 7.53–7.60 (2H, m, ArH), 7.64 (1H, s, ArH), 9.57 (1H, s, NH).

HPLC: retention time 7.15 min [Method B].

One or the other (as indicated) of the two following synthetic protocols was used to generate each of the compounds below:

Protocol A:

To an isocyanate (1 mmol) in CH$_2$Cl$_2$ (4 mL) was added dropwise a solution of 3-(3-aminophenyl)-4-bromo-1-methylpyrazole (1 mmol) in CH$_2$Cl$_2$ (4 mL). The mixture was stirred for 16 hours and concentrated. Chromatography on flash silica (20%–80% EtOAc/hexane) followed by recrystallisation gave the pure urea.

Protocol B:

To a stirred solution of triphosgene (0.33 mmol) in CH$_2$Cl$_2$ (4 mL) was added dropwise a solution of 3-(3-aminophenyl)4-bromo-1-methylpyrazole (1 mmol) and triethylamine (2 mmol) in CH$_2$Cl$_2$ (4 mL). After 1 hour, an aniline was added (1 mmol). The reaction mixture was stirred for 16 hours and concentrated. Chromatography on flash silica (20%–80% EtOAc/hexane) followed by recrystallisation gave the pure urea.

Experiment 14

Preparation and Analysis of 116079

N-[3-(4-bromo-1-methylpyrazol-3-yl)phenyl][(4-methylthiophenyl)amino]carboxamide

[Protocol A]-4-(methylthio)phenyl isocyanate
colourless solid (EtOAc/hexane)
MS (ES+): m/z (%)=419 (M+H $^{81}$Br, 100), 417 (M+H $^{79}$Br, 94).

$^1$H-NMR (MeOH d$_4$): δ=2.42 (3H, s, SCH$_3$), 3.81 (3H, s, NCH$_3$), 7.06 (1H, m, ArH), 7.22 (2H, m, ArH), 7.37 (2H, m, ArH), 7.42–7.61 (4H, m, ArH).

HPLC: retention time 3.35 min [Method A].

Experiment 15

Preparation and Analysis of 116081

N-[3-(4-bromo-1-methylpyrazol-3-yl)phenyl][(4-chlorophenyl)amino]carboxamide

[Protocol A]-4-chlorophenyl isocyanate
colourless solid (EtOAc/hexane)
MS (ES+): m/z (%)=409 (M+H $^{81}$Br $^{37}$Cl, 19), 407 (M+H $^{79}$Br $^{37}$Cl ($^{81}$Br $^{35}$Cl), 100), 405 (M+H $^{79}$Br $^{35}$Cl, 81).
$^1$H-NMR (MeOH d$_4$): δ=3.81 (3H, s, CH$_3$), 7.07 (1H, m, ArH), 7.23 (2H, m, ArH), 7.36–7.60 (6H, m, ArH).

HPLC: retention time 3.42 min [Method A].

Experiment 16

Preparation and Analysis of 116082

{[3-(4-bromo-1-methylpyrazol-3-yl)phenyl]amino}-N-(4-fluorophenyl)carboxamide

[Protocol A]-4-fluorophenyl isocyanate
colourless solid (EtOAc/hexane)
MS (ES+): m/z (%)=391 (M+H $^{81}$Br, 96), 389 (M+H $^{79}$Br, 100).
$^1$H-NMR (MeOH d$_4$): δ=3.81 (3H, s, CH$_3$), 6.93–7.11 (3H, m, ArH), 7.37–7.61 (6H, m, ArH).

HPLC: retention time 3.11 min.

Experiment 17

Preparation and Analysis of 116087

{[3-(4-bromo-1-methylpyrazol-3-yl)phenyl]amino}-N-[2-(trifluoromethoxy)phenyl]carboxamide

[Protocol A]-2-(trifluoromethoxy)phenyl isocyanate
colourless solid (EtOAc/hexane)
MS (ES+): m/z (%)=457 (M+H $^{81}$Br, 100), 455 (M+H $^{79}$Br, 95).
$^1$H-NMR (DMSO d$_6$): δ=3.79 (3H, s, CH$_3$), 7.06–7.18 (2H, m, ArH), 7.38–7.49 (2H, m, ArH), 7.51–7.62 (2H, m, ArH), 7.65 (1H, m, ArH), 7.71 (1H, s, ArH), 8.24 (1H, dd, J=1.1, 8.2, ArH), 8.56 (1H, s, NH), 9.49 (1H, s, NH).

HPLC: retention time 3.40 min.

Experiment 18

Preparation and Analysis of 116089

{[3-(4-bromo-1-methylpyrazol-3-yl)phenyl]amino}-N-(2-nitrophenyl)carboxamide

[Protocol A]-2-nitrophenyl isocyanate
yellow solid (EtOAc/hexane)
MS (ES+): m/z (%)=418 (M+H $^{81}$Br, 98), 416 (M+H $^{79}$Br, 100).
$^1$H-NMR (DMSO d$_6$): δ=$^1$H-NMR (DMSO d$_6$): □=3.79 (3H, s, NCH$_3$), 7.14 (1H, m, ArH), 7.24 (1H, m, ArH), 7.50 (1H, t, J=7.7, ArH), 7.60 (2H, m, ArH), 7.67 (1H, s, ArH), 7.71 (1H, s, ArH), 8.10 (1H, m, ArH), 8.29 (1H, m, ArH), 9.65 (1H, s, NH), 10.09 (1H, s, NH).

HPLC: retention time 3.10 min [Method A].

Experiment 19

Preparation and Analysis of 116091

{[3-(4-bromo-1-methylpyrazol-3-yl)phenyl]amino}-N(4-methoxyphenyl)carboxamide

[Protocol A]-4-methoxyphenyl isocyanate
colourless solid (EtOAc/hexane)
MS (ES+): m/z (%)=403 (M+H $^{81}$Br, 100), 401 (M+H $^{79}$Br, 96).
$^1$H-NMR (DMSO d$_6$): δ=3.71 (3H, s, OCH$_3$), 3.79 (3H, s, NCH$_3$), 6.87 (2H, d, J=8.9, ArH), 7.06 (1H, d, J=7.5, ArH), 7.39 (2H, d, J=8.9, ArH), 7.45–7.61 (3H, m, ArH), 7.65 (1H, s, ArH), 8.52 (1H, s, NH), 8.84 (1H, s, NH).

HPLC: retention time 3.08 min.

Experiment 20

Preparation and Analysis of 116092

{[3-(4-bromo-1-methylpyrazol-3-yl)phenyl]amino}-N-(2-methylphenyl)carboxamide

[Protocol A]-o-tolyl isocyanate
colourless solid (EtOAc/hexane)
MS (ES+): m/z (%)=387 (M+H $^{81}$Br, 94), 385 (M+H $^{79}$Br, 100).
$^1$H-NMR (MeOH d$_4$): δ=2.29 (3H, s, CH$_3$), 3.81 (3H, s, NCH$_3$), 7.03 (1H, dt, J=1.1,7.5, ArH), 7.09 (1H, dt, J=1.1, 7.5, ArH), 7.13–7.22 (2H, m, ArH), 7.45 (1H, t, J=7.9, ArH), 7.49–7.57 (2H, m, ArH), 7.60–7.68 (2H, m, ArH).

HPLC: retention time 2.96 min.

Experiment 21

Preparation and Analysis of 116097

{[3-(4-bromo-1-methylpyrazol-3-yl)phenyl]amino}-N-[4-(trifluoromethyl)phenyl]carboxamide

[Protocol A]-4-(trifluoromethyl)phenyl isocyanate
colourless solid (EtOAc/hexane)
MS (ES+): m/z (%)=441 (M+H $^{81}$Br, 94), 439 (M+H $^{79}$Br, 100).
$^1$H-NMR (MeOH d$_4$): δ=3.82 (3H, s, CH$_3$), 7.04–7.16 (3H, m, ArH), 7.20–7.47 (6H, m, ArH).

HPLC: retention time 3.56 min.

Experiment 22

Preparation and Analysis of 116105

{[3-(4-bromo-1-methylpyrazol-3-yl)phenyl]amino}-N-(3-chlorophenyl)carboxamide

[Protocol A]-3-chlorophenyl isocyanate
colourless solid (EtOAc/hexane)
MS (ES+): m/z (%)=409 (M+H $^{81}$Br $^{37}$Cl, 26), 407 (M+H $^{79}$Br $^{37}$Cl ($^{81}$Br $^{35}$Cl), 100), 405 (M+H $^{79}$Br $^{35}$Cl, 70).
$^1$H-NMR (MeOH d$_4$): δ=3.81 (3H, s, NCH$_3$), 7.04 (1H, m, ArH), 7.10 (1H, m, ArH), 7.28 (2H, m, ArH), 7.47 (1H, t, J=7.8, ArH), 7.55 (1H, m, ArH), 7.63 (1H, m, ArH), 7.68 (1H, s, ArH), 7.73 (1H, m, ArH), 9.04 (2H, s, NH).
HPLC: retention time 3.20 min [Method A].

Experiment 23

Preparation and Analysis of 116108

{[3-(4-bromo-1-methylpyrazol-3-yl)phenyl]amino}-N-(2-chlorophenyl)carboxamide

[Protocol A]-2-chlorophenyl isocyanate
colourless solid (EtOAc/hexane)
MS (ES+): m/z (%)=409 (M+H $^{81}$Br $^{37}$Cl, 24), 407 (M+H $^{79}$Br $^{37}$Cl ($^{81}$Br $^{35}$Cl), 100), 405 (M+H $^{79}$Br $^{35}$Cl, 72).
$^1$H-NMR (MeOH d$_4$): δ=3.81 (3H, s, NCH$_3$), 7.03 (1H, m, ArH), 7.11 (1H, m, ArH), 7.28 (1H, m, ArH), 7.35–7.53 (3H, m, ArH), 7.55 (1H, s, ArH), 7.62 (1H, m, ArH), 8.11 (1H, m, ArH).
HPLC: retention time 3.13 min.

Experiment 24

Preparation and Analysis of 116110

{[3-(4-bromo-1-methylpyrazol-3yl)phenyl]amino}-N-[4-(methylethyl)phenyl]carboxamide

[Protocol A]-4-isopropylphenyl isocyanate
colourless solid (THF/hexane)
MS (ES+): m/z (%)=415 (M+H $^{81}$Br, 100), 413 (M+H $^{79}$Br, 92).
$^1$H-NMR (MeOH d$_4$): δ=1.23 (6H, d, J=6.8, 2xCH$_3$), 2.86 (1H, septet, J=6.8, CH), 3.82 (3H, s, NCH$_3$), 7.09 (1H, m, ArH), 7.16 (2H, d, J=7.6, ArH), 7.31 (2H, d, J=7.6, ArH), 7.42–7.51 (2H, m, ArH), 7.54 (1H, s, ArH), 7.59 (1H, m, ArH).
HPLC: retention time 3.66 min.

Experiment 25

Preparation and Analysis of 116111

{[3-(4-bromo-1-methylpyrazol-3-yl)phenyl]amino}-N-(3-methoxyphenyl)carboxamide

[Protocol A]-3-methoxyphenyl isocyanate
colourless solid (EtOAc/hexane)
MS (ES+): m/z (%)=403 (M+H $^{81}$Br, 100), 401 (M+H $^{79}$Br, 96).
$^1$H-NMR (MeOH d$_4$): δ=3.73 (3H, s, OCH$_3$), 3.81 (3H, s, NCH$_3$), 6.59 (1H, m, ArH), 6.91 (1H, m, ArH), 7.08 (1H, m, ArH), 7.14 (2H, m, ArH), 7.39–7.61 (4H, m, ArH).
HPLC: retention time 2.90 min.

Experiment 26

Preparation and Analysis of 116112

{[3-(4-bromo-1-methylpyrazol-3-yl)phenyl]amino}-N-(3-methylphenyl)carboxamide

[Protocol A]-m-tolyl isocyanate
colourless solid (EtOAc/hexane)
MS (ES+): m/z (%)=387 (M+H $^{81}$Br, 100), 385 (M+H $^{79}$Br, 96).
$^1$H-NMR (DMSO d$_6$): δ=2.26 (3H, s, CH$_3$), 3.76 (3H, s, NCH$_3$), 6.79 (1H, m, ArH), 7.06–7.22 (3H, m, ArH), 7.29 (1H, m, ArH), 7.43–7.62 (3H, m, ArH), 7.68 (1H, s, ArH), 8.65 (1H, s, NH), 8.89 (1H, s, NH).
HPLC: retention time 3.05 min [Method A].

Experiment 27

Preparation and Analysis of 116113

{[3-(4-bromo-1-methylpyrazol-3-yl)phenyl]amino}-N-methyl-N-[4-(trifluoromethoxy)phenyl]carboxamide

[Protocol B]-N-methyl4-(trifluoromethoxy)aniline
pale yellow solid (EtOAc/hexane)
MS (ES+): m/z (%)=471 (M+H $^{81}$Br, 88), 469 (M+H $^{79}$Br, 100).
$^1$H-NMR (MeOH d$_4$): δ=3.35 (3H, s, NCH$_3$), 3.81 (3H, s, NCH$_3$), 7.09 (1H, m, ArH), 7.25–7.51 (8H, m, ArH).
HPLC: retention time 3.56 min [Method A].

Experiment 28

Preparation and Analysis of 116119

N-[4-(tert-butyl)phenyl]{[3-(4-bromo-1-methylpyrazol-3-yl)phenyl]amino}carboxamide

[Protocol B]-4-tert-butylaniline
colourless solid (EtOAc/hexane)
MS (ES+): m/z (%)=429 (M+H $^{81}$Br, 98), 427 (M+H $^{79}$Br, 100).
$^1$H-NMR (DMSO d$_6$): δ=1.27 (9H, s, 3xCH$_3$), 3.79 (3H, s, NCH$_3$), 7.07 (1H, d, J=7.5, ArH), 7.29 (2H, d, J=8.7, ArH), 7.37 (2H, d, J=8.7, ArH), 7.45 (1H, t, J=7.5, ArH), 7.51–7.60 (2H, m, ArH), 7.66 (1H, s, ArH), 8.65 (1H, s, NH), 8.83 (1H, s, NH).
HPLC: retention time 3.77 min.

Experiment 29

Preparation and Analysis of 116122

N-[4-(dimethylamino)phenyl]{[3-(4-bromo-1-methylpyrazol-3-yl)phenyl]amino}carboxamide

[Protocol B]-N,N-dimethyl-p-phenylenediamine
colourless solid (EtOAc/hexane)
MS (ES+): m/z (%)=416 (M+H $^{81}$Br, 96), 414 (M+H $^{79}$Br, 100).
$^1$H-NMR (DMSO d$_6$): δ=2.86 (6H, s, NCH$_3$), 3.80 (3H, s, NCH$_3$), 6.80 (2H, m, ArH), 7.09 (1H, d, J=7.7, ArH), 7.28 (2H, m, ArH), 7.42 (1H, t, J=7.8, ArH), 7.52 (1H, m, ArH), 7.59 (1H, s, ArH), 7.67 (1H, s, ArH), 8.45 (1H, s, NH), 8.75 (1H, s, NH).
HPLC: retention time 2.07 min [Method A].

Experiment 30

Preparation and Analysis of 116138

N-(3,5-dichloro-4-methylphenyl){[3-(4bromo-1-methylpyrazol-3-yl)phenyl]amino}carboxamide

[Protocol B]-3,5-dichloro-4-methylphenylamine
colourless solid (EtOAc/hexane)
MS (ES+): m/z (%)=457 (M+H, 35), 455 (M+H, 100), 453 (M+H, 65).

¹H-NMR (DMSO d₆): δ=2.32 (3H, s, CH₃), 3.79 (3H, s, NCH₃), 7.11 (1H, d, J=7.4, ArH), 7.46 (1H, t, J=7.8, ArH), 7.50–7.64 (4H, m, ArH), 7.68 (1H, s, ArH), 9.02 (1H, s, NH), 9.09 (1H, s, NH).
HPLC: retention time 3.66 min.

Experiment 31

Preparation and Analysis of 116139

{[3-(4-bromo-1-methylpyrazol-3-yl)phenyl]amino}-N-[4-(trifluoromethylthio)phenyl]carboxamide

[Protocol B]-4-(trifluoromethylthio)aniline
colourless solid (EtOAc/hexane)
MS (ES+): m/z (%)=473 (M+H $^{81}$Br, 100), 471 (M+H $^{79}$Br, 94).
¹H-NMR (DMSO d₆): δ=3.81 (3H, s, NCH₃), 7.11 (1H, d, J=7.5, ArH), 7.47 (1H, t, J=7.9, ArH), 7.51–7.63 (6H, m, ArH), 7.66 (1H, s, ArH), 9.03 (1H, s, NH), 9.16 (1H, s, NH).
HPLC: retention time 3.76 min.

Experiment 32

Preparation and Analysis of 116141

{[3-(4-bromo-1-methylpyrazol-3-yl)phenyl]amino}-N-(cyclohexyl)carboxamide

[Protocol B]-cyclohexylamine
colourless solid, m.p. 155.5–156.3° C. (EtOAc/hexane).
MS (ES+): m/z (%)=379 (M+H $^{81}$Br, 93), 377 (M+H $^{79}$Br, 100).
¹H-NMR (DMSO d₆): δ=1.07–1.34 (5H, m, 5xCH), 1.52 (1H, m, CH), 1.63 (2H, m, 2xCH), 1.76 (2H, m, 2xCH), 3.48 (1H, m, NCH), 3.74 (3H, s, CH₃), 6.15 (1H, d, J=7.8, ArH), 6.98 (1H, d, J=7.5, ArH), 7.32–7.43 (2H, m, ArH), 7.51 (1H, m, NH), 7.62 (1H, s, ArH), 8.50 (1H, s, NH).
HPLC: retention time 3.16 min [Method A].
TLC: retention factor 0.35 (50% EtOAc/hexane).

Experiment 33

Preparation and Analysis of 116143

{[3-(4-bromo-1-methylpyrazol-3-yl)phenyl]amino}-N-(phenylmethyl)carboxamide

[Protocol B]-benzylamine
colourless solid, m.p. 144.5–146.2° C. (EtOAc/hexane).
IR: $\square_{max}$=1622, 1565, 1467, 1374, 1239, 973, 802, 752, 695 cm$^{-1}$.
MS (ES+): m/z (%)=387 (M+H $^{81}$Br, 89), 385 (M+H $^{79}$Br, 100).
¹H-NMR (CD₃OD): δ=3.81 (3H, s, CH₃), 4.40 (2H, s, CH₂), 7.05 (1H, m, ArH), 7.19–7.51 (9H, m, ArH).
HPLC: retention time 3.06 min [Method A].a Experiment 34

Preparation and Analysis of 116144

{[3-(4-bromo-1-methylpyrazol-3-yl)phenyl]amino}-N-(2-fluropheny)carbooxamide

[Protocol A]-2-fluorophenyl isocyanate
colourless solid (DCM/hexane)
MS (ES+): m/z (%)=391 (M+H $^{81}$Br, 100), 389 (M+H $^{79}$Br, 90).

¹H-NMR (MeOH d₄): δ=3.79 (3H, s, NCH₃), 7.00–7.11 (4H, m, ArH), 7.40–7.56 (3H, m, ArH), 7.61 (5H, m, ArH), 8.09 (1H, m, ArH).
HPLC: retention time 3.01 min.

Experiment 35

Preparation and Analysis of 116145

2-({[3-(4-bromo-1-methylpyrazol-3-yl)phenyl]amino}cabonylamino)benzamide

[Protocol B]-2-aminobenzamide
colourless solid (EtOAc/hexane)
MS (ES+): m/z (%)=399 (M+H-17 $^{81}$Br, 100), 397 (M+H -17 $^{79}$Br,94).
¹H-NMR (DMSO d₆): δ=3.79 (3H, s, NCH₃), 6.93–7.10 (2H, m, ArH), 7.45 (2H, t, J=7.8, ArH), 7.59–7.72 (5H, m, ArH), 8.22 (2H, m), 9.92 (1H, s,NH), 10.69 (1H, s, NH).
HPLC: retention time 2.88 min.

Experiment 36

Preparation and Analysis of 116147

{[3-(4-bromo-1-methylpyrazol-3-yl)phenyl]amino}-N-(4-cyanophenyl)carboxamide

[Protocol B]-4-aminobenzonitrile
colourless solid (EtOAc/hexane)
MS (ES+): m/z (%)=398 (M+H $^{81}$Br, 100), 396 (M+H $^{79}$Br, 96).
¹H-NMR (MeOH d₄): δ=3.81 (3H, s, NCH₃), 7.12 (1H, m, ArH), 7.46–7.57 (3H, m, ArH), 7.62–7.69 (5H, m, ArH).
HPLC: retention time 3.12 min.

Experiment 37

Preparation and Analysis of AR116148

{[3-(4-bromo-1methylpyrazol-3-yl)phenyl]amino}-N-(2-cyanophenyl)carboxamide

[Protocol B]-2-aminobenzonitrile
colourless solid (EtOAc/hexane)
MS (ES+): m/z (%)=398 (M+H $^{81}$Br, 95), 396 (M+H $^{79}$Br, 100).
¹H-NMR (CDCl₃): δ=3.79 (3H, s, CH₃), 7.13–7.28 (2H, m, ArH), 7.49 (1H, t, J=7.8, ArH), 7.57 (1H, m, ArH), 7.62 (1H, m, ArH), 7.65–7.71 (2H, m, ArH), 7.78 (1H, m, ArH), 8.07 (1H, d, J=8.6, ArH), 8.83 (1H, s, NH), 9.62 (1H, s, NH).
HPLC: retention time 3.05 min [Method A].

Experiment 38

Preparation and Analysis of 116182

{[3-(4-bromo-1-methylpyrazol-3-yl)phenyl]amino}-N-(4-fluorophenylmethyl)carboxamide

[Protocol B]-4-fluorobenzylamine
colourless solid, m.p. 185.5–186.6° C. (EtOAc/hexane).
MS (ES+): m/z (%)=405 (M+H $^{81}$Br, 97), 403 (M+H $^{79}$Br, 100).
¹H-NMR (DMSO d₆): δ=3.75 (3H, s, CH₃), 4.28 (2H, d, J=6.0, CH₂), 6.73 (1H, t, J=5.9, NH), 7.01 (1H, d, J=7.5, ArH), 7.10–7.18 (2H, m, ArH), 7.27–7.41 (4H, m, ArH), 7.56 (1H, s, ArH), 7.62 (1H, s, ArH), 8.82 (1H, s, NH).
HPLC: retention time 3.10 min [Method A].
TLC: retention factor 0.25 (50% EtOAc/hexane).

Experiment 39

Preparation and Analysis of 116183

{[3-(4-bromo-1-methylpyrazol-3-yl)phenyl]amino}-N-(3,4-dimethoxyphenylmethyl)carboxamide

[Protocol B]-3,4-dimethoxybenzylamine
colourless solid, m.p. 174.9–175.5° C. (EtOAc/hexane).
MS (CI+): m/z (%)=447 (M+H $^{81}$Br, 100), 445 (M+H $^{79}$Br, 92).
$^1$H-NMR (DMSO d$_6$): δ=3.71 (3H, s, CH$_3$), 3.73 (3H, s, CH$_3$), 3.76 (3H, s, CH$_3$), 4.22 (2H, d, J=5.8, CH$_2$), 6.62 (1H, t, J=5.7, NH), 6.80 (1H, m, ArH), 6.89 (2H, m, ArH), 6.98 (1H, m, ArH), 7.36–7.51 (3H, m, ArH), 7.63 (1H, s, ArH), 8.76 (1H, s, NH).
HPLC: retention time 2.86 min [Method A].
TLC: retention factor 0.20 (50% EtOAc/hexane).

Experiment 40

Preparation and Analysis of 116184

{[3-(4-bromo-1-methylpyrazol-3-yl)phenyl]amino}-N-(3,4,5-trimethoxyphenylmethyl)carboxamide

[Protocol B]-3,4,5-trimethoxybenzylamine
colourless solid (EtOAc/hexane).
MS (CI+): m/z (%)=477 (M+H $^{81}$Br, 100), 475 (M+H $^{79}$Br, 95).
$^1$H-NMR (DMSO d$_6$): δ=3.63 (3H, s, OCH$_3$), 3.75 (9H, s, 3×CH$_3$), 4.21 (1H, d, J=5.9, CH$_2$), 6.61 (2H, s, ArH), 6.65 (1H, t, J=5.9, NH), 6.99 (1H, m, ArH), 7.40 (1H, t, J=7.7, ArH), 7.45 (1H, m, ArH), 7.56 (1H, m, ArH), 7.64 (1H, s, ArH), 8.77 (1H, s, NH).
HPLC: retention time 5.91 min [Method B].
TLC: retention factor 0.50 (50% EtOAc/hexane).

Experiment 41

Preparation and Analysis of 116185

{[3-(4-bromo-1-methylpyrazol-3-yl)phenyl]amino}-N-(2-methylphenylmethyl)carboxamide

[Protocol B]-2-methylbenzylamine
colourless solid (EtOAc/hexane).
MS (CI+): m/z (%)=401 (M+H $^{81}$Br, 96), 399 (M+H $^{79}$Br, 100).
$^1$H-NMR (DMSO d$_6$): δ=2.28 (3H, s, CH$_3$), 3.76 (3H, s, NCH$_3$), 4.28 (1H, d, J=5.8, CH$_2$), 6.60 (1H, t, J=5.8, NH), 7.01 (1H, m, ArH), 7.15 (3H, m, ArH), 7.24 (1H, m, ArH), 7.38–7.50 (2H, m, ArH), 7.57 (1H, m, ArH), 7.65 (1H, s, ArH), 8.77 (1H, s, NH).
HPLC: retention time 2.74 min [Method A].
TLC: retention factor 0.20 (50% EtOAc/hexane).

Experiment 42

Preparation and Analysis of 116189

{[3-(4-bromo-1-methylpyrazol-3-yl)phenyl]amino}-N-(4-methoxyphenylmethyl)carboxamide

[Protocol B]-4-methoxybenzylamine
colourless solid (EtOAc/hexane).
MS (CI+): m/z (%)=417 (M+H $^{81}$Br, 94), 415 (M+H $^{79}$Br, 100).
$^1$H-NMR (DMSO d$_6$): δ=3.72 (3H, s, CH$_3$), 3.77 (3H, s, NCH$_3$), 4.22 (1H, d, J=5.9, CH$_2$), 6.62 (1H, t, J=5.9, NH), 6.90 (2H, d, J=8.8, ArH), 7.00 (1H, m, ArH), 7.23 (2H, d, J=8.8, ArH), 7.39 (1H, t, J=7.8, ArH), 7.43 (1H, m, ArH), 7.56 (11H, m, ArH), 7.64 (1H, S, ArH), 8.73 (1H, s, NH).
HPLC: retention time 6.41 min [Method B].
TLC: retention factor 0.25 (50% EtOAc/hexane).

Experiment 43

Preparation and Analysis of 116194

{[3-(4-bromo-1-methylpyrazol-3-yl)phenyl]amino}-N-[2-(4-methoxy)phenylethyl]carboxamide

[Protocol B]-2-(4-methoxyphenyl)ethylamine
colourless solid (EtOAc/hexane).
MS (ES+): m/z (%)=431 (M+H $^{81}$Br, 95), 429 (M+H $^{79}$Br, 100).
$^1$H-NMR (DMSO d$_6$): δ=2.68 (2H, t, J=7.1, CH$_2$), 3.31 (2H, m, CH$_2$), 3.71 (3H, s, CH$_3$), 3.77 (3H, s, CH$_3$), 6.16 (1I, t, J=5.8, NH), 6.87 (2H, d, J=8.6, ArH), 6.99 (1H, dt, J=1.4, 7.3, ArH), 7.16 (2H, d, J=8.6, ArH), 7.33–7.48 (2H, m, ArH), 7.52 (1H, m, ArH), 7.63 (1H, s, ArH), 8.71 (1H, s, NH).
HPLC: retention time 6.62 min [Method B].

An important point that can be derived from the foregoing data is that by using a constitutively activated form of the receptor in the direct identification of candidate compounds, the selectivity of the compounds is exceptional: as those in the art appreciate, the homology between the human 5HT2A and 5HT2C receptors is about 95%, and even with such homology, certain of the directly identified compounds evidence a 4-order-of-magnitude (10,000-fold) selectivity separation (116100). This is important for pharmaceutical compositions in that such selectivity can help to reduce side-effects associated with interaction of a drug with a non-target receptor.

Different embodiments of the invention will consist of different constitutively activated receptors, different expression systems, different assays, and different compounds. Those skilled in the art will understand which receptors to use with which expression systems and assay methods. All are considered within the scope of the teaching of this invention. In addition, those skilled in the art will recognize that various modifications, additions, substitutions, and variations to the illustrative examples set forth herein can be made without departing from the spirit of the invention and are, therefore, considered within the scope of the invention.

We claim:

1. A method of identifying whether a candidate compound is an inverse agonist to a non-endogenous human 5HT2 serotonin receptor comprising the steps of:

a. contacting the candidate compound with a non-endogenous human 5HT2 serotonin receptor, said receptor comprising the amino acid sequence of SEQ.ID.NO.:31; and b. determining, by measurement of the compound efficacy at said contacted receptor whether said compound is an inverse agonist, said compound efficacy measurement being an inhibition of a second messenger response relative to a second messenger response of said receptor in the absence of said compound, said second messenger response being selected from the group consisting of levels of inositol triphosphate ($IP_3$) and levels of diacycglycerol (DAG).

* * * * *

SEQUENCE LISTING

<160> NUMBER OF SEQ ID NOS: 33

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 1
gacctcgagg ttgcttaaga ctgaagc                                       27

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 2
atttctagac atatgtagct tgtaccg                                       27

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 3 ctagggcac catgcaggct atcaacaatg aaagaaaagc taagaaagtc               50

<210> SEQ ID NO 4
<211> LENGTH: 50
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 4
caaggacttt cttagctttt ctttcattgt tgatagcctg catggtgccc              50

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 5
gacctcgagt ccttctacac ctcatc                                        26

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 6
tgctctagat tccagatagg tgaaaacttg                              30

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 7
caaagaaagt actgggcatc gtcttcttcc t                            31

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 8
ccgctcgagt actgcgccga caagctttga t                            31

<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 9
cgatgcccag cactttcgaa gcttttcttt cattgttg                     38

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 10
aaaagcttcg aaagtgctgg gcatcgtctt cttcct                       36

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 11
tgctctagat tccagatagg tgaaaacttg                              30

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 12
cgtgtctctc cttacttca                                          19

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 13
tcggcgcagt actttgatag ttagaaagta ggtgat                       36

<210> SEQ ID NO 14
<211> LENGTH: 38
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 14
ttctaactat caaagtactg cgccgacaag ctttgatg                     38

<210> SEQ ID NO 15
<211> LENGTH: 43
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 15
ttcagcagtc aacccactag tctatactct gttcaacaaa att               43

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 16
atttctagac atatgtagct tgtaccgt                                28

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 17
atcacctact ttctaacta                                          19

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Novel
      Sequence

```
<400> SEQUENCE: 18
ccataatcgt cagggaatg aaaaatgaca caa                                    33

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 19
atttttcatt ccctgacga ttatggtgat tac                                    33

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 20
tgatgaagaa agggcaccac atgatcagaa aca                                   33

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 21
gatcatgtgg tgccctttct tcatcacaaa cat                                   33

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 22
gagacatatt atctgccacg gagg                                             24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 23
ttggcataga aaccggaccc aagg                                             24

<210> SEQ ID NO 24
<211> LENGTH: 1416
<212> TYPE: DNA
<213> ORGANISM: Artificial Sequence
<220> FEATURE:
<223> OTHER INFORMATION: Description of Artificial Sequence: Novel
      Sequence
```

-continued

```
<400> SEQUENCE: 24
atggatattc tttgtgaaga aaatacttct ttgagctcaa ctacgaactc cctaatgcaa      60
ttaaatgatg acaacaggct ctacagtaat gactttaact ccggagaagc taacacttct     120
gatgcattta actggacagt cgactctgaa atcgaacca acctttcctg tgaagggtgc      180
ctctcaccgt cgtgtctctc cttacttcat ctccaggaaa aaaactggtc tgctttactg     240
acagccgtag tgattattct aactattgct ggaaacatac tcgtcatcat ggcagtgtcc     300
ctagagaaaa agctgcagaa tgccaccaac tatttcctga tgtcacttgc catagctgat     360
atgctgctgg gtttccttgt catgcccgtg tccatgttaa ccatcctgta tgggtaccgg     420
tggcctctgc cgagcaagct ttgtgcagtc tggatttacc tggacgtgct cttctccacg     480
gcctccatca tgcacctctg cgccatctcg ctggaccgct acgtcgccat ccagaatccc     540
atccaccaca gccgcttcaa ctccagaact aaggcatttc tgaaaatcat tgctgtttgg     600
accatatcag taggtatatc catgccaata ccagtctttg gctacagga cgattcgaag      660
gtctttaagg aggggagttg cttactcgcc gatgataact ttgtcctgat cggctctttt     720
gtgtcatttt tcattccctt aaccatcatg gtgatcacct actttctaac tatcaagtca     780
ctccagaaag aagctacttt tgtgtaagt gatcttggca cacgggccaa attagcttct      840
ttcagcttcc tccctcagag ttctttgtct tcagaaaagc tcttccagcg gtcgatccat     900
agggagccag ggtcctacac aggcaggagg actatgcagt ccatcagcaa tgagcaaaag     960
gcatgcaagg tgctgggcat cgtcttcttc ctgtttgtgg tgatgtggtg ccctttcttc    1020
atcacaaaca tcatggccgt catctgcaaa gagtcctgca atgaggatgt cattggggcc    1080
ctgctcaatg tgtttgtttg gatcggttat ctctcttcag cagtcaaccc actagtctac    1140
acactgttca caagaccta taggtcagcc ttttcacggt atattcagtg tcagtacaag     1200
gaaacaaaa aaccattgca gttaatttta gtgaacacaa taccggcttt ggcctacaag     1260
tctagccaac ttcaaatggg acaaaaaaag aattcaaagc aagatgccaa gacaacagat    1320
aatgactgct caatggttgc tctaggaaag cagtattctg aagaggcttc taaagacaat    1380
agcgacggag tgaatgaaaa ggtgagctgt gtgtga                              1416
```

```
<210> SEQ ID NO 25
<211> LENGTH: 470
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 25

Met Asp Ile Leu Cys Glu Glu Asn Thr Ser Leu Ser Ser Thr Thr Asn
  1               5                  10                  15

Ser Leu Met Gln Leu Asn Asp Asp Asn Arg Leu Tyr Ser Asn Asp Phe
                 20                  25                  30

Asn Ser Gly Glu Ala Asn Thr Ser Asp Ala Phe Asn Trp Thr Val Asp
             35                  40                  45

Ser Glu Asn Arg Thr Asn Leu Ser Cys Glu Gly Cys Leu Ser Pro Ser
         50                  55                  60

Cys Ser Leu Leu His Leu Gln Glu Lys Asn Trp Ser Ala Leu Leu Thr
 65                  70                  75                  80

Ala Val Val Ile Ile Leu Thr Ile Ala Gly Asn Ile Leu Val Ile Met
                 85                  90                  95
```

-continued

Ala Val Ser Leu Glu Lys Lys Leu Gln Asn Ala Thr Asn Tyr Phe Leu
            100                 105                 110

Met Ser Leu Ala Ile Ala Asp Met Leu Leu Gly Phe Leu Val Met Pro
        115                 120                 125

Val Ser Met Leu Thr Ile Leu Tyr Gly Tyr Arg Trp Pro Leu Pro Ser
    130                 135                 140

Lys Leu Cys Ala Val Trp Ile Tyr Leu Asp Val Leu Phe Ser Thr Ala
145                 150                 155                 160

Ser Ile Met His Leu Cys Ala Ile Ser Leu Asp Arg Tyr Val Ala Ile
                165                 170                 175

Gln Asn Pro Ile His His Ser Arg Phe Asn Ser Arg Thr Lys Ala Phe
            180                 185                 190

Leu Lys Ile Ile Ala Val Trp Thr Ile Ser Val Gly Ile Ser Met Pro
        195                 200                 205

Ile Pro Val Phe Gly Leu Gln Asp Asp Ser Lys Val Phe Lys Glu Gly
    210                 215                 220

Ser Cys Leu Leu Ala Asp Asp Asn Phe Val Leu Ile Gly Ser Phe Val
225                 230                 235                 240

Ser Phe Phe Ile Pro Leu Thr Ile Met Val Ile Thr Tyr Phe Leu Thr
                245                 250                 255

Ile Lys Ser Leu Gln Lys Glu Ala Thr Leu Cys Val Ser Asp Leu Gly
            260                 265                 270

Thr Arg Ala Lys Leu Ala Ser Phe Ser Phe Leu Pro Gln Ser Ser Leu
        275                 280                 285

Ser Ser Glu Lys Leu Phe Gln Arg Ser Ile His Arg Glu Pro Gly Ser
    290                 295                 300

Tyr Thr Gly Arg Arg Thr Met Gln Ser Ile Ser Asn Glu Gln Lys Ala
305                 310                 315                 320

Cys Lys Val Leu Gly Ile Val Phe Phe Leu Phe Val Val Met Trp Cys
                325                 330                 335

Pro Phe Phe Ile Thr Asn Ile Met Ala Val Ile Cys Lys Glu Ser Cys
            340                 345                 350

Asn Glu Asp Val Ile Gly Ala Leu Leu Asn Val Phe Val Trp Ile Gly
        355                 360                 365

Tyr Leu Ser Ser Ala Val Asn Pro Leu Val Tyr Thr Leu Phe Asn Lys
    370                 375                 380

Thr Tyr Arg Ser Ala Phe Ser Arg Tyr Ile Gln Cys Gln Tyr Lys Glu
385                 390                 395                 400

Asn Lys Lys Pro Leu Gln Leu Ile Leu Val Asn Thr Ile Pro Ala Leu
                405                 410                 415

Ala Tyr Lys Ser Ser Gln Leu Gln Met Gly Gln Lys Lys Asn Ser Lys
            420                 425                 430

Gln Asp Ala Lys Thr Thr Asp Asn Asp Cys Ser Met Val Ala Leu Gly
        435                 440                 445

Lys Gln Tyr Ser Glu Glu Ala Ser Lys Asp Asn Ser Asp Gly Val Asn
    450                 455                 460

Glu Lys Val Ser Cys Val
465                 470

<210> SEQ ID NO 26
<211> LENGTH: 1377
<212> TYPE: DNA

<210> SEQ ID NO 26
<211> LENGTH: 1377
<212> TYPE: DNA
<213> ORGANISM: Artificial Sequence
<220> FEATURE:
<223> OTHER INFORMATION: Description of Artificial Sequence: Novel Sequence

<400> SEQUENCE: 26

| | | | | | |
|---|---|---|---|---|---|
| atggtgaacc tgaggaatgc ggtgcattca ttccttgtgc acctaattgg cctattggtt | 60 |
| tggcaatgtg atatttctgt gagcccagta gcagctatag taactgacat tttcaatacc | 120 |
| tccgatggtg gacgcttcaa attcccagac ggggtacaaa actggccagc actttcaatc | 180 |
| gtcatcataa taatcatgac aataggtggc aacatccttg tgatcatggc agtaagcatg | 240 |
| gaaaagaaac tgcacaatgc caccaattac ttcttaatgt ccctagccat tgctgatatg | 300 |
| ctagtgggac tacttgtcat gccccctgtct ctcctggcaa tccttatga ttatgtctgg | 360 |
| ccactaccta gatatttgtg ccccgtctgg atttctttag atgttttatt ttcaacagcg | 420 |
| tccatcatgc acctctgcgc tatatcgctg atcggtatg tagcaatacg taatcctatt | 480 |
| gagcatagcc gtttcaattc gcggactaag gccatcatga agattgctat tgtttgggca | 540 |
| atttctatag gtgtatcagt tcctatccct gtgattggac tgaggacga agaaaaggtg | 600 |
| ttcgtgaaca acacgacgtg cgtgctcaac gacccaaatt tcgttcttat tgggtccttc | 660 |
| gtagctttct tcataccgct gacgattatg gtgattacgt attgcctgac catctacgtt | 720 |
| ctgcgccgac aagctttgat gttactgcac ggccacaccg aggaaccgcc tggactaagt | 780 |
| ctggatttcc tgaagtgctg caagaggaat acggccgagg aagagaactc tgcaaaccct | 840 |
| aaccaagacc agaacgcacg ccgaagaaag aagaaggaga gacgtcctag gggcaccatg | 900 |
| caggctatca acaatgaaag aaaagcttcg aaagtccttg ggattgtttt ctttgtgttt | 960 |
| ctgatcatgt ggtgcccatt tttcattacc aatattctgt ctgttctttg tgagaagtcc | 1020 |
| tgtaaccaaa agctcatgga aaagcttctg aatgtgtttg tttggattgg ctatgtttgt | 1080 |
| tcaggaatca atcctctggt gtatctctgt ttcaacaaaa tttaccgaag ggcattctcc | 1140 |
| aactatttgc gttgcaatta taggtagag aaaaagcctc ctgtcaggca gattccaaga | 1200 |
| gttgccgcca ctgctttgtc tgggagggag cttaatgtta acatttatcg gcataccaat | 1260 |
| gaaccggtga tcgagaaagc cagtgacaat gagcccggta tagagatgca agttgagaat | 1320 |
| ttagagttac cagtaaatcc ctccagtgtg ttagcgaaa ggattagcag tgtgtga | 1377 |

<210> SEQ ID NO 27
<211> LENGTH: 458
<212> TYPE: PRT
<213> ORGANISM: Artificial Sequence
<220> FEATURE:
<223> OTHER INFORMATION: Description of Artificial Sequence: Novel Sequence

<400> SEQUENCE: 27

Met Val Asn Leu Arg Asn Ala Val His Ser Phe Leu Val His Leu Ile
1               5                   10                  15

Gly Leu Leu Val Trp Gln Cys Asp Ile Ser Val Ser Pro Val Ala Ala
                20                  25                  30

Ile Val Thr Asp Ile Phe Asn Thr Ser Asp Gly Gly Arg Phe Lys Phe
            35                  40                  45

Pro Asp Gly Val Gln Asn Trp Pro Ala Leu Ser Ile Val Ile Ile Ile
        50                  55                  60

Ile Met Thr Ile Gly Gly Asn Ile Leu Val Ile Met Ala Val Ser Met
65                  70                  75                  80

-continued

```
Glu Lys Lys Leu His Asn Ala Thr Asn Tyr Phe Leu Met Ser Leu Ala
                85                  90                  95

Ile Ala Asp Met Leu Val Gly Leu Leu Val Met Pro Leu Ser Leu Leu
            100                 105                 110

Ala Ile Leu Tyr Asp Tyr Val Trp Pro Leu Pro Arg Tyr Leu Cys Pro
        115                 120                 125

Val Trp Ile Ser Leu Asp Val Leu Phe Ser Thr Ala Ser Ile Met His
    130                 135                 140

Leu Cys Ala Ile Ser Leu Asp Arg Tyr Val Ala Ile Arg Asn Pro Ile
145                 150                 155                 160

Glu His Ser Arg Phe Asn Ser Arg Thr Lys Ala Ile Met Lys Ile Ala
                165                 170                 175

Ile Val Trp Ala Ile Ser Ile Gly Val Ser Val Pro Ile Pro Val Ile
            180                 185                 190

Gly Leu Arg Asp Glu Glu Lys Val Phe Val Asn Asn Thr Thr Cys Val
        195                 200                 205

Leu Asn Asp Pro Asn Phe Val Leu Ile Gly Ser Phe Val Ala Phe Phe
    210                 215                 220

Ile Pro Leu Thr Ile Met Val Ile Thr Tyr Cys Leu Thr Ile Tyr Val
225                 230                 235                 240

Leu Arg Arg Gln Ala Leu Met Leu Leu His Gly His Thr Glu Glu Pro
                245                 250                 255

Pro Gly Leu Ser Leu Asp Phe Leu Lys Cys Cys Lys Arg Asn Thr Ala
            260                 265                 270

Glu Glu Glu Asn Ser Ala Asn Pro Asn Gln Asp Gln Asn Ala Arg Arg
        275                 280                 285

Arg Lys Lys Lys Glu Arg Arg Pro Arg Gly Thr Met Gln Ala Ile Asn
    290                 295                 300

Asn Glu Arg Lys Ala Ser Lys Val Leu Gly Ile Val Phe Phe Val Phe
305                 310                 315                 320

Leu Ile Met Trp Cys Pro Phe Phe Ile Thr Asn Ile Leu Ser Val Leu
                325                 330                 335

Cys Glu Lys Ser Cys Asn Gln Lys Leu Met Glu Lys Leu Leu Asn Val
            340                 345                 350

Phe Val Trp Ile Gly Tyr Val Cys Ser Gly Ile Asn Pro Leu Val Tyr
        355                 360                 365

Thr Leu Phe Asn Lys Ile Tyr Arg Arg Ala Phe Ser Asn Tyr Leu Arg
    370                 375                 380

Cys Asn Tyr Lys Val Glu Lys Lys Pro Pro Val Arg Gln Ile Pro Arg
385                 390                 395                 400

Val Ala Ala Thr Ala Leu Ser Gly Arg Glu Leu Asn Val Asn Ile Tyr
                405                 410                 415

Arg His Thr Asn Glu Pro Val Ile Glu Lys Ala Ser Asp Asn Glu Pro
            420                 425                 430

Gly Ile Glu Met Gln Val Glu Asn Leu Glu Leu Pro Val Asn Pro Ser
        435                 440                 445

Ser Val Val Ser Glu Arg Ile Ser Ser Val
    450                 455
```

<210> SEQ ID NO 28
<211> LENGTH: 1377
<212> TYPE: DNA

<213> ORGANISM: Artificial Sequence
<220> FEATURE:
<223> OTHER INFORMATION: Description of Artificial Sequence: Novel
      Sequence

<400> SEQUENCE: 28

| | | | | | |
|---|---|---|---|---|---|
| atggtgaacc | tgaggaatgc | ggtgcattca | ttccttgtgc | acctaattgg | cctattggtt | 60 |
| tggcaatgtg | atatttctgt | gagcccagta | gcagctatag | taactgacat | tttcaatacc | 120 |
| tccgatggtg | gacgcttcaa | attcccagac | ggggtacaaa | actggccagc | actttcaatc | 180 |
| gtcatcataa | taatcatgac | aataggtggc | aacatccttg | tgatcatggc | agtaagcatg | 240 |
| gaaaagaaac | tgcacaatgc | caccaattac | ttcttaatgt | ccctagccat | tgctgatatg | 300 |
| ctagtgggac | tacttgtcat | gcccctgtct | ctcctggcaa | tcctttatga | ttatgtctgg | 360 |
| ccactaccta | gatatttgtg | ccccgtctgg | atttctttag | atgttttatt | ttcaacagcg | 420 |
| tccatcatgc | acctctgcgc | tatatcgctg | atcggtatg | tagcaatacg | taatcctatt | 480 |
| gagcatagcc | gtttcaattc | gcggactaag | gccatcatga | agattgctat | tgtttgggca | 540 |
| atttctatag | gtgtatcagt | tcctatccct | gtgattggac | tgaggacga | agaaaaggtg | 600 |
| ttcgtgaaca | acacgacgtg | cgtgctcaac | gacccaaatt | tcgttcttat | tgggtccttc | 660 |
| gtagctttct | tcataccgct | gacgattatg | gtgattacg | attgcctgac | catctacgtt | 720 |
| ctgcgccgac | aagctttgat | gttactgcac | ggccacaccg | aggaaccgcc | tggactaagt | 780 |
| ctggatttcc | tgaagtgctg | caagaggaat | acggccgagg | aagagaactc | tgcaaaccct | 840 |
| aaccaagacc | agaacgcacg | ccgaagaaag | aagaaggaga | gacgtcctag | ggcaccatg | 900 |
| caggctatca | acaatgaaag | aaaagctaag | aaagtccttg | ggattgtttt | ctttgtgttt | 960 |
| ctgatcatgt | ggtgcccatt | tttcattacc | aatattctgt | ctgttctttg | tgagaagtcc | 1020 |
| tgtaaccaaa | agctcatgga | aaagcttctg | aatgtgtttg | tttggattgg | ctatgtttgt | 1080 |
| tcaggaatca | atcctctggt | gtatactctg | ttcaacaaaa | tttaccgaag | ggcattctcc | 1140 |
| aactatttgc | gttgcaatta | taaggtagag | aaaaagcctc | ctgtcaggca | gattccaaga | 1200 |
| gttgccgcca | ctgctttgtc | tgggagggag | cttaatgtta | acatttatcg | gcataccaat | 1260 |
| gaaccggtga | tcgagaaagc | cagtgacaat | gagcccggta | tagagatgca | agttgagaat | 1320 |
| ttagagttac | cagtaaatcc | ctccagtgtg | gttagcgaaa | ggattagcag | tgtgtga | 1377 |

<210> SEQ ID NO 29
<211> LENGTH: 458
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 29

Met Val Asn Leu Arg Asn Ala Val His Ser Phe Leu Val His Leu Ile
  1               5                  10                  15

Gly Leu Leu Val Trp Gln Cys Asp Ile Ser Val Ser Pro Val Ala Ala
                 20                  25                  30

Ile Val Thr Asp Ile Phe Asn Thr Ser Asp Gly Gly Arg Phe Lys Phe
             35                  40                  45

Pro Asp Gly Val Gln Asn Trp Pro Ala Leu Ser Ile Val Ile Ile Ile
         50                  55                  60

Ile Met Thr Ile Gly Gly Asn Ile Leu Val Ile Met Ala Val Ser Met
 65                  70                  75                  80

-continued

```
Glu Lys Lys Leu His Asn Ala Thr Asn Tyr Phe Leu Met Ser Leu Ala
                 85                  90                  95

Ile Ala Asp Met Leu Val Gly Leu Leu Val Met Pro Leu Ser Leu Leu
            100                 105                 110

Ala Ile Leu Tyr Asp Tyr Val Trp Pro Leu Pro Arg Tyr Leu Cys Pro
        115                 120                 125

Val Trp Ile Ser Leu Asp Val Leu Phe Ser Thr Ala Ser Ile Met His
    130                 135                 140

Leu Cys Ala Ile Ser Leu Asp Arg Tyr Val Ala Ile Arg Asn Pro Ile
145                 150                 155                 160

Glu His Ser Arg Phe Asn Ser Arg Thr Lys Ala Ile Met Lys Ile Ala
                165                 170                 175

Ile Val Trp Ala Ile Ser Ile Gly Val Ser Val Pro Ile Pro Val Ile
            180                 185                 190

Gly Leu Arg Asp Glu Glu Lys Val Phe Val Asn Asn Thr Thr Cys Val
        195                 200                 205

Leu Asn Asp Pro Asn Phe Val Leu Ile Gly Ser Phe Val Ala Phe Phe
    210                 215                 220

Ile Pro Leu Thr Ile Met Val Ile Thr Tyr Cys Leu Thr Ile Tyr Val
225                 230                 235                 240

Leu Arg Arg Gln Ala Leu Met Leu Leu His Gly His Thr Glu Glu Pro
                245                 250                 255

Pro Gly Leu Ser Leu Asp Phe Leu Lys Cys Cys Lys Arg Asn Thr Ala
            260                 265                 270

Glu Glu Glu Asn Ser Ala Asn Pro Asn Gln Asp Gln Asn Ala Arg Arg
        275                 280                 285

Arg Lys Lys Lys Glu Arg Arg Pro Arg Gly Thr Met Gln Ala Ile Asn
    290                 295                 300

Asn Glu Arg Lys Ala Lys Lys Val Leu Gly Ile Val Phe Phe Val Phe
305                 310                 315                 320

Leu Ile Met Trp Cys Pro Phe Phe Ile Thr Asn Ile Leu Ser Val Leu
                325                 330                 335

Cys Glu Lys Ser Cys Asn Gln Lys Leu Met Glu Lys Leu Leu Asn Val
            340                 345                 350

Phe Val Trp Ile Gly Tyr Val Cys Ser Gly Ile Asn Pro Leu Val Tyr
        355                 360                 365

Thr Leu Phe Asn Lys Ile Tyr Arg Arg Ala Phe Ser Asn Tyr Leu Arg
    370                 375                 380

Cys Asn Tyr Lys Val Glu Lys Lys Pro Pro Val Arg Gln Ile Pro Arg
385                 390                 395                 400

Val Ala Ala Thr Ala Leu Ser Gly Arg Glu Leu Asn Val Asn Ile Tyr
                405                 410                 415

Arg His Thr Asn Glu Pro Val Ile Glu Lys Ala Ser Asp Asn Glu Pro
            420                 425                 430

Gly Ile Glu Met Gln Val Glu Asn Leu Glu Leu Pro Val Asn Pro Ser
        435                 440                 445

Ser Val Val Ser Glu Arg Ile Ser Ser Val
    450                 455

<210> SEQ ID NO 30
<211> LENGTH: 1437
<212> TYPE: DNA
```

<213> ORGANISM: Artificial Sequence
<220> FEATURE:
<223> OTHER INFORMATION: Description of Artificial Sequence: Novel Sequence

<400> SEQUENCE: 30

```
atggatattc tttgtgaaga aatacttct ttgagctcaa ctacgaactc cctaatgcaa      60
ttaaatgatg caacaggct ctacagtaat gactttaact ccggagaagc taacacttct     120
gatgcattta actggacagt cgactctgaa atcgaacca acctttcctg tgaagggtgc     180
ctctcaccgt cgtgtctctc cttacttcat ctccaggaaa aaactggtc tgctttactg     240
acagccgtag tgattattct aactattgct ggaaacatac tcgtcatcat ggcagtgtcc    300
ctagagaaaa agctgcagaa tgccaccaac tatttcctga tgtcacttgc catagctgat    360
atgctgctgg gtttccttgt catgcccgtg tccatgttaa ccatcctgta tgggtaccgg    420
tggcctctgc cgagcaagct ttgtgcagtc tggatttacc tggacgtgct cttctccacg    480
gcctccatca tgcacctctg cgccatctcg ctggaccgct acgtcgccat ccagaatccc    540
atccaccaca gccgcttcaa ctccagaact aaggcatttc tgaaaatcat tgctgtttgg    600
accatatcag taggtatatc catgccaata ccagtctttg gctacagga cgattcgaag    660
gtctttaagg aggggagttg cttactcgcc gatgataact ttgtcctgat cggctctttt    720
gtgtcatttt tcattccctt aaccatcatg gtgatcacct actttctaac tatcaaggtt    780
ctgcgccgac aagctttgat gttactgcac ggccacaccg aggaaccgcc tggactaagt    840
ctggatttcc tgaagtgctg caagaggaat acggccgagg aagagaactc tgcaaaccct    900
aaccaagacc agaacgcacg ccgaagaaag aagaaggaga cgtcctag gggcaccatg     960
caggctatca acaatgaaag aaaagcttcg aaggtactgg gcatcgtctt cttcctgttt   1020
gtggtgatgt ggtgcccttt cttcatcaca aacatcatgg ccgtcatctg caaagagtcc   1080
tgcaatgagg atgtcattgg ggccctgctc aatgtgtttg tttggatcgg ttatctctct   1140
tcagcagtca acccactagt ctatactctg ttcaacaaaa tttaccgaag ggcattctcc   1200
aactatttgc gttgcaatta taggtagag aaaaagcctc ctgtcaggca gattccaaga   1260
gttgccgcca ctgctttgtc tgggagggag cttaatgtta acatttatcg gcataccaat   1320
gaaccggtga tcgagaaagc cagtgacaat gagcccggta tagagatgca agttgagaat   1380
ttagagttac cagtaaatcc ctccagtgtg gttagcgaaa ggattagcag tgtgtga      1437
```

<210> SEQ ID NO 31
<211> LENGTH: 478
<212> TYPE: PRT
<213> ORGANISM: Artificial Sequence
<220> FEATURE:
<223> OTHER INFORMATION: Description of Artificial Sequence: Novel Sequence

<400> SEQUENCE: 31

```
Met Asp Ile Leu Cys Glu Glu Asn Thr Ser Leu Ser Ser Thr Thr Asn
  1               5                  10                  15

Ser Leu Met Gln Leu Asn Asp Asp Asn Arg Leu Tyr Ser Asn Asp Phe
             20                  25                  30

Asn Ser Gly Glu Ala Asn Thr Ser Asp Ala Phe Asn Trp Thr Val Asp
         35                  40                  45

Ser Glu Asn Arg Thr Asn Leu Ser Cys Glu Gly Cys Leu Ser Pro Ser
     50                  55                  60
```

-continued

```
Cys Leu Ser Leu Leu His Leu Gln Glu Lys Asn Trp Ser Ala Leu Leu
 65                  70                  75                  80

Thr Ala Val Val Ile Ile Leu Thr Ile Ala Gly Asn Ile Leu Val Ile
                 85                  90                  95

Met Ala Val Ser Leu Glu Lys Lys Leu Gln Asn Ala Thr Asn Tyr Phe
            100                 105                 110

Leu Met Ser Leu Ala Ile Ala Asp Met Leu Leu Gly Phe Leu Val Met
        115                 120                 125

Pro Val Ser Met Leu Thr Ile Leu Tyr Gly Tyr Arg Trp Pro Leu Pro
    130                 135                 140

Ser Lys Leu Cys Ala Val Trp Ile Tyr Leu Asp Val Leu Phe Ser Thr
145                 150                 155                 160

Ala Ser Ile Met His Leu Cys Ala Ile Ser Leu Asp Arg Tyr Val Ala
                165                 170                 175

Ile Gln Asn Pro Ile His His Ser Arg Phe Asn Ser Arg Thr Lys Ala
            180                 185                 190

Phe Leu Lys Ile Ile Ala Val Trp Thr Ile Ser Val Gly Ile Ser Met
        195                 200                 205

Pro Ile Pro Val Phe Gly Leu Gln Asp Asp Ser Lys Val Phe Lys Glu
    210                 215                 220

Gly Ser Cys Leu Leu Ala Asp Asp Asn Phe Val Leu Ile Gly Ser Phe
225                 230                 235                 240

Val Ser Phe Phe Ile Pro Leu Thr Ile Met Val Ile Thr Tyr Phe Leu
                245                 250                 255

Thr Ile Lys Val Leu Arg Arg Gln Ala Leu Met Leu Leu His Gly His
            260                 265                 270

Thr Glu Glu Pro Pro Gly Leu Ser Leu Asp Phe Leu Lys Cys Cys Lys
        275                 280                 285

Arg Asn Thr Ala Glu Glu Glu Asn Ser Ala Asn Pro Asn Gln Asp Gln
    290                 295                 300

Asn Ala Arg Arg Arg Lys Lys Lys Glu Arg Arg Pro Arg Gly Thr Met
305                 310                 315                 320

Gln Ala Ile Asn Asn Glu Arg Lys Ala Ser Lys Val Leu Gly Ile Val
                325                 330                 335

Phe Phe Leu Phe Val Val Met Trp Cys Pro Phe Phe Ile Thr Asn Ile
            340                 345                 350

Met Ala Val Ile Cys Lys Glu Ser Cys Asn Glu Asp Val Ile Gly Ala
        355                 360                 365

Leu Leu Asn Val Phe Val Trp Ile Gly Tyr Leu Ser Ser Ala Val Asn
    370                 375                 380

Pro Leu Val Tyr Thr Leu Phe Asn Lys Ile Tyr Arg Arg Ala Phe Ser
385                 390                 395                 400

Asn Tyr Leu Arg Cys Asn Tyr Lys Val Glu Lys Lys Pro Pro Val Arg
                405                 410                 415

Gln Ile Pro Arg Val Ala Ala Thr Ala Leu Ser Gly Arg Glu Leu Asn
            420                 425                 430

Val Asn Ile Tyr Arg His Thr Asn Glu Pro Val Ile Glu Lys Ala Ser
        435                 440                 445

Asp Asn Glu Pro Gly Ile Glu Met Gln Val Glu Asn Leu Glu Leu Pro
    450                 455                 460

Val Asn Pro Ser Ser Val Val Ser Glu Arg Ile Ser Ser Val
465                 470                 475
```

<210> SEQ ID NO 32
<211> LENGTH: 1437
<212> TYPE: DNA
<213> ORGANISM: Artificial Sequence
<220> FEATURE:
<223> OTHER INFORMATION: Description of Artificial Sequence: Novel Sequence

<400> SEQUENCE: 32

```
atggatattc tttgtgaaga aaatacttct ttgagctcaa ctacgaactc cctaatgcaa      60
ttaaatgatg acaacaggct ctacagtaat gactttaact ccggagaagc taacacttct     120
gatgcattta actggacagt cgactctgaa atcgaacca acctttcctg tgaagggtgc      180
ctctcaccgt cgtgtctctc cttacttcat ctccaggaaa aaaactggtc tgctttactg     240
acagccgtag tgattattct aactattgct ggaaacatac tcgtcatcat ggcagtgtcc     300
ctagagaaaa agctgcagaa tgccaccaac tatttcctga tgtcacttgc catagctgat     360
atgctgctgg gtttccttgt catgcccgtg tccatgttaa ccatcctgta tgggtaccgg     420
tggcctctgc cgagcaagct ttgtgcagtc tggatttacc tggacgtgct cttctccacg     480
gcctccatca tgcacctctg cgccatctcg ctggaccgct acgtcgccat ccagaatccc     540
atccaccaca gccgcttcaa ctccagaact aaggcatttc tgaaaatcat tgctgtttgg     600
accatatcag taggtatatc catgccaata ccagtctttg gctacaggga cgattcgaag     660
gtctttaagg aggggagttg cttactcgcc gatgataact ttgtcctgat cggctctttt     720
gtgtcatttt tcattcccct gacgattatg gtgattacgt attgcctgac catctacgtt     780
ctgcgccgac aagctttgat gttactgcac ggccacaccg aggaaccgcc tggactaagt     840
ctggatttcc tgaagtgctg caagaggaat acggccgagg aagagaactc tgcaaaccct     900
aaccaagacc agaacgcacg ccgaagaaag aagaaggaga acgtcctag gggcaccatg     960
caggctatca acaatgaaag aaaagctaag aaagtccttg ggattgtttt ctttgtgttt    1020
ctgatcatgt ggtgcccttt cttcatcaca aacatcatgg ccgtcatctg caaagagtcc    1080
tgcaatgagg atgtcattgg ggccctgctc aatgtgtttg tttggatcgg ttatctctct    1140
tcagcagtca acccactagt ctatactctg ttcaacaaaa tttaccgaag ggcattctcc    1200
aactatttgc gttgcaatta aggtagag aaaaagcctc ctgtcaggca gattccaaga     1260
gttgccgcca ctgctttgtc tgggagggag cttaatgtta acatttatcg gcataccaat    1320
gaaccggtga tcgagaaagc cagtgacaat gagcccggta tagagatgca agttgagaat    1380
ttagagttac cagtaaatcc ctccagtgtg gttagcgaaa ggattagcag tgtgtga      1437
```

<210> SEQ ID NO 33
<211> LENGTH: 478
<212> TYPE: PRT
<213> ORGANISM: Artificial Sequence
<220> FEATURE:
<223> OTHER INFORMATION: Description of Artificial Sequence: Novel Sequence

<400> SEQUENCE: 33

```
Met Asp Ile Leu Cys Glu Glu Asn Thr Ser Leu Ser Ser Thr Thr Asn
  1               5                  10                  15

Ser Leu Met Gln Leu Asn Asp Asp Asn Arg Leu Tyr Ser Asn Asp Phe
             20                  25                  30

Asn Ser Gly Glu Ala Asn Thr Ser Asp Ala Phe Asn Trp Thr Val Asp
         35                  40                  45
```

-continued

```
Ser Glu Asn Arg Thr Asn Leu Ser Cys Glu Gly Cys Leu Ser Pro Ser
 50                  55                  60

Cys Leu Ser Leu Leu His Leu Gln Glu Lys Asn Trp Ser Ala Leu Leu
 65                  70                  75                  80

Thr Ala Val Val Ile Ile Leu Thr Ile Ala Gly Asn Ile Leu Val Ile
                     85                  90                  95

Met Ala Val Ser Leu Glu Lys Lys Leu Gln Asn Ala Thr Asn Tyr Phe
                100                 105                 110

Leu Met Ser Leu Ala Ile Ala Asp Met Leu Leu Gly Phe Leu Val Met
                115                 120                 125

Pro Val Ser Met Leu Thr Ile Leu Tyr Gly Tyr Arg Trp Pro Leu Pro
130                 135                 140

Ser Lys Leu Cys Ala Val Trp Ile Tyr Leu Asp Val Leu Phe Ser Thr
145                 150                 155                 160

Ala Ser Ile Met His Leu Cys Ala Ile Ser Leu Asp Arg Tyr Val Ala
                165                 170                 175

Ile Gln Asn Pro Ile His His Ser Arg Phe Asn Ser Arg Thr Lys Ala
                180                 185                 190

Phe Leu Lys Ile Ile Ala Val Trp Thr Ile Ser Val Gly Ile Ser Met
                195                 200                 205

Pro Ile Pro Val Phe Gly Leu Gln Asp Asp Ser Lys Val Phe Lys Glu
                210                 215                 220

Gly Ser Cys Leu Leu Ala Asp Asp Asn Phe Val Leu Ile Gly Ser Phe
225                 230                 235                 240

Val Ser Phe Phe Ile Pro Leu Thr Ile Met Val Ile Thr Tyr Cys Leu
                245                 250                 255

Thr Ile Tyr Val Leu Arg Arg Gln Ala Leu Met Leu Leu His Gly His
                260                 265                 270

Thr Glu Glu Pro Pro Gly Leu Ser Leu Asp Phe Leu Lys Cys Cys Lys
                275                 280                 285

Arg Asn Thr Ala Glu Glu Glu Asn Ser Ala Asn Pro Asn Gln Asp Gln
290                 295                 300

Asn Ala Arg Arg Arg Lys Lys Lys Glu Arg Arg Pro Arg Gly Thr Met
305                 310                 315                 320

Gln Ala Ile Asn Asn Glu Arg Lys Ala Lys Lys Val Leu Gly Ile Val
                325                 330                 335

Phe Phe Val Phe Leu Ile Met Trp Cys Pro Phe Phe Ile Thr Asn Ile
                340                 345                 350

Met Ala Val Ile Cys Lys Glu Ser Cys Asn Glu Asp Val Ile Gly Ala
                355                 360                 365

Leu Leu Asn Val Phe Val Trp Ile Gly Tyr Leu Ser Ser Ala Val Asn
370                 375                 380

Pro Leu Val Tyr Thr Leu Phe Asn Lys Ile Tyr Arg Arg Ala Phe Ser
385                 390                 395                 400

Asn Tyr Leu Arg Cys Asn Tyr Lys Val Glu Lys Lys Pro Pro Val Arg
                405                 410                 415

Gln Ile Pro Arg Val Ala Ala Thr Ala Leu Ser Gly Arg Glu Leu Asn
                420                 425                 430

Val Asn Ile Tyr Arg His Thr Asn Glu Pro Val Ile Glu Lys Ala Ser
                435                 440                 445

Asp Asn Glu Pro Gly Ile Glu Met Gln Val Glu Asn Leu Glu Leu Pro
450                 455                 460
```

```
Val Asn Pro Ser Ser Val Val Ser Glu Arg Ile Ser Ser Val
465             470              475
```